US010953223B2

(12) United States Patent
Sparks et al.

(10) Patent No.: US 10,953,223 B2
(45) Date of Patent: Mar. 23, 2021

(54) DEVICE AND METHOD FOR POSITIONING AN ELECTRODE IN A BODY CAVITY

(71) Applicant: BioTrace Medical, Inc., San Carlos, CA (US)

(72) Inventors: Kurt Sparks, Palo Alto, CA (US); Ellis Garai, Palo Alto, CA (US); Aravind Swaminathan, San Mateo, CA (US); Laura Dietch, Menlo Park, CA (US); Marcel Sicotte, San Francisco, CA (US)

(73) Assignee: BioTrace Medical, Inc., Menlo Park, CA (US)

( * ) Notice: Subject to any disclaimer, the term of this patent is extended or adjusted under 35 U.S.C. 154(b) by 88 days.

(21) Appl. No.: 16/256,473

(22) Filed: Jan. 24, 2019

(65) Prior Publication Data

US 2019/0217084 A1 Jul. 18, 2019

Related U.S. Application Data

(63) Continuation of application No. 15/844,367, filed on Dec. 15, 2017, now Pat. No. 10,232,170, which is a
(Continued)

(51) Int. Cl.
*A61N 1/05* (2006.01)
*A61B 6/12* (2006.01)
(Continued)

(52) U.S. Cl.
CPC ............ *A61N 1/0558* (2013.01); *A61B 5/283* (2021.01); *A61B 6/12* (2013.01); *A61N 1/057* (2013.01);
(Continued)

(58) Field of Classification Search
None
See application file for complete search history.

(56) References Cited

U.S. PATENT DOCUMENTS 4,559,951 A 12/1985 Dahl et al.
4,570,642 A 2/1986 Kane et al.
(Continued)

FOREIGN PATENT DOCUMENTS

JP 2002542891 A 12/2002
JP 2004510507 A 4/2004
(Continued)

OTHER PUBLICATIONS

Co-pending U.S. Appl. No. 15/691,187, filed Aug. 30, 2017.
(Continued)

*Primary Examiner* — Brian T Gedeon
(74) *Attorney, Agent, or Firm* — Wilson Sonsini Goodrich and Rosati, P.C.

(57) ABSTRACT

Electrical sensing/stimulation apparatuses for positioning at least one electrode within body tissue are provided. An electrical sensing/stimulation apparatus may comprise an elongate lead body having at least one internal lumen, at least one sensing/stimulation electrode, a deployable/retractable displacement member that moves or biases at least one electrode towards a prescribed direction by the user, a tissue attachment mechanism for affixing the distal segment of the device to body tissue, and an atraumatic distal lead body termination. In a retracted configuration, the attachment mechanism is positioned substantially within the distal segment of the lead body, and in the deployed configuration, the attachment mechanism extends from the axis of the lead body to engage body tissue.

52 Claims, 41 Drawing Sheets

Related U.S. Application Data continuation of application No. 14/707,246, filed on May 8, 2015, now Pat. No. 9,872,981.

(60) Provisional application No. 61/990,998, filed on May 9, 2014.

(51) Int. Cl.
*A61B 5/042* (2006.01)
*A61B 5/283* (2021.01)
*A61B 5/00* (2006.01)
*A61N 1/36* (2006.01)
*A61B 5/287* (2021.01)
*A61B 90/00* (2016.01)
*A61B 5/0215* (2006.01)
*A61B 5/024* (2006.01)
*A61B 17/22* (2006.01)

(52) U.S. Cl.
CPC ............ *A61N 1/0573* (2013.01); *A61B 5/024* (2013.01); *A61B 5/0215* (2013.01); *A61B 5/287* (2021.01); *A61B 5/686* (2013.01); *A61B 5/6879* (2013.01); *A61B 2017/22071* (2013.01); *A61B 2090/3966* (2016.02); *A61B 2562/0209* (2013.01); *A61N 1/36017* (2013.01); *A61N 2001/058* (2013.01); *A61N 2001/0578* (2013.01)

(56) References Cited

U.S. PATENT DOCUMENTS

| | | | |
|---|---|---|---|
| 5,195,989 A | 3/1993 | Euteneuer |
| 5,255,693 A | 10/1993 | Dutcher et al. |
| 5,336,252 A | 8/1994 | Cohen |
| 5,443,492 A | 8/1995 | Stokes et al. |
| 5,476,500 A | 12/1995 | Fain et al. |
| 5,571,162 A | 11/1996 | Lin |
| 5,645,580 A | 7/1997 | Moaddeb et al. |
| 5,683,447 A | 11/1997 | Bush et al. |
| 5,871,531 A | 2/1999 | Struble |
| 6,055,457 A | 4/2000 | Bonner |
| 6,163,728 A | 12/2000 | Wildon |
| 6,273,886 B1 | 8/2001 | Edwards et al. |
| 6,470,219 B1 | 10/2002 | Edwards et al. |
| 6,544,230 B1 | 4/2003 | Flaherty et al. |
| 6,553,265 B1 | 4/2003 | Fischer, Sr. |
| 6,574,514 B2 | 6/2003 | Partridge et al. |
| 6,697,677 B2 | 2/2004 | Dahl et al. |
| 6,942,613 B2 | 9/2005 | Ewers et al. |
| 7,056,286 B2 | 6/2006 | Ravenscroft et al. |
| 7,092,765 B2 | 8/2006 | Geske et al. |
| 7,099,718 B1 | 8/2006 | Thacker et al. |
| 7,211,063 B2 | 5/2007 | Tom |
| 7,231,260 B2 | 6/2007 | Wallace et al. |
| 7,274,965 B1 | 9/2007 | Karicherla et al. |
| 7,463,932 B2 | 12/2008 | Cawthra, Jr. |
| 7,509,169 B2 | 3/2009 | Eigler et al. |
| 7,526,342 B2 | 4/2009 | Chin et al. |
| 7,546,166 B2 | 6/2009 | Michels et al. |
| 7,601,159 B2 | 10/2009 | Ewers et al. |
| 7,610,104 B2 | 10/2009 | Kaplan et al. |
| 7,662,151 B2 | 2/2010 | Crompton et al. |
| 7,684,873 B2 | 3/2010 | Gerber |
| 7,736,198 B2 | 6/2010 | Bjorklund et al. |
| 7,765,012 B2 | 7/2010 | Gerber |
| 7,765,015 B2 | 7/2010 | Johnson et al. |
| 7,832,406 B2 | 11/2010 | Ellis et al. |
| 7,865,249 B2 | 1/2011 | Reddy |
| 7,991,484 B1 | 8/2011 | Sengupta et al. |
| 8,019,440 B2 | 9/2011 | Kokones et al. |
| 8,019,443 B2 | 9/2011 | Schleicher et al. |
| 8,055,356 B2 | 11/2011 | Wengreen et al. |
| 8,160,710 B2 | 4/2012 | Buysman et al. |
| 8,219,213 B2 | 7/2012 | Sommer et al. |
| 8,340,780 B2 | 12/2012 | Hastings et al. |
| 8,398,672 B2 | 3/2013 | Kleshinski et al. |
| 8,409,239 B2 | 4/2013 | Kleshinski et al. |
| 8,467,875 B2 | 6/2013 | Bennett et al. |
| 9,044,592 B2 | 6/2015 | Imran et al. |
| 9,844,663 B2 | 12/2017 | Swaminathan et al. |
| 9,855,421 B2 | 1/2018 | Garai et al. |
| 9,872,981 B2 | 1/2018 | Sparks et al. |
| 10,124,162 B2 | 11/2018 | Garai et al. |
| 10,232,170 B2 | 3/2019 | Sparks et al. |
| 2001/0031994 A1 | 10/2001 | Mika et al. |
| 2003/0149331 A1 | 8/2003 | Geitz |
| 2003/0212446 A1 | 11/2003 | Kaplan et al. |
| 2004/0158143 A1 | 8/2004 | Flaherty et al. |
| 2005/0251238 A1 | 11/2005 | Wallace et al. |
| 2006/0276749 A1 | 12/2006 | Selmon et al. |
| 2007/0051377 A1 | 3/2007 | Douk et al. |
| 2007/0093780 A1 | 4/2007 | Kugler et al. |
| 2007/0208357 A1 | 9/2007 | Houser et al. |
| 2007/0213798 A1 | 9/2007 | Dreier et al. |
| 2008/0009914 A1 | 1/2008 | Buysman et al. |
| 2008/0051832 A1 | 2/2008 | To et al. |
| 2008/0051847 A1 | 2/2008 | Kelly |
| 2008/0077217 A1 | 3/2008 | Santamore et al. |
| 2008/0103575 A1 | 5/2008 | Gerber |
| 2008/0109054 A1 | 5/2008 | Hastings et al. |
| 2008/0132981 A1 | 6/2008 | Gerber |
| 2009/0012592 A1 | 1/2009 | Buysman et al. |
| 2009/0030331 A1 | 1/2009 | Hochareon et al. |
| 2009/0076476 A1 | 3/2009 | Barbagli et al. |
| 2009/0163822 A1 | 6/2009 | Doan |
| 2009/0248095 A1 | 10/2009 | Schleicher et al. |
| 2009/0259272 A1 | 10/2009 | Reddy et al. |
| 2009/0306549 A1 | 12/2009 | MacAdam et al. |
| 2010/0198041 A1 | 8/2010 | Christian et al. |
| 2010/0204560 A1 | 8/2010 | Salahieh et al. |
| 2011/0004148 A1 | 1/2011 | Ishii |
| 2011/0313427 A1 | 12/2011 | Gindele et al. |
| 2012/0029513 A1 | 2/2012 | Smith et al. |
| 2012/0089215 A1 | 4/2012 | Kaplan et al. |
| 2012/0123531 A1 | 5/2012 | Tsukashima et al. |
| 2012/0190958 A1 | 7/2012 | Annest et al. |
| 2012/0316627 A1 | 12/2012 | Finlay et al. |
| 2012/0323253 A1 | 12/2012 | Garai et al. |
| 2013/0188291 A1 | 7/2013 | Vardiman |
| 2013/0325093 A1 | 12/2013 | Foster |
| 2015/0320330 A1 | 11/2015 | Sparks et al. |
| 2015/0343201 A1 | 12/2015 | Swaminathan et al. |
| 2019/0038893 A1 | 2/2019 | Garai et al. |

FOREIGN PATENT DOCUMENTS

| | | |
|---|---|---|
| JP | 2010516436 A | 5/2010 |
| WO | WO-0066052 A1 | 11/2000 |
| WO | WO-2008134651 A2 | 11/2008 |
| WO | WO-2009135075 A1 | 11/2009 |
| WO | WO-2009135080 A1 | 11/2009 |
| WO | WO-2012028475 A1 | 3/2012 |
| WO | WO-2012047408 A1 | 4/2012 |
| WO | WO-2015172023 A2 | 11/2015 |
| WO | WO-2015172023 A3 | 2/2016 |

OTHER PUBLICATIONS

European search report and search opinion dated Dec. 20, 2017 for EP Application No. 15788891.8.

European search report and written opinion dated Apr. 3, 2014 (completed Mar. 26, 2014) for EP Application No. 11831130.7.

First Examination Report for European Patent Application No. 11831130.7, dated May 2, 2016 (4 pages).

First Office Action issued by the Japanese Patent Office for corresponding Japanese Patent Application No. 2013-530158, Ref. No. P238126WOJP01, dated Jun. 1, 2015, pp. 1-5.

International search report and written opinion dated Jan. 6, 2012 for PCT Application No. US2011/049499.

International search report and written opinion dated Oct. 6, 2015 for PCT Application No. PCT/US2015/029890.

(56) References Cited

OTHER PUBLICATIONS

Japanese Final Rejection issued for Japanese Patent Application No. 2013530158, dated Feb. 10, 2016 (4 pages).
"Notice of Allowance dated Jul. 3, 2018 for U.S. Appl. No. 15/691,187".
Notice of allowance dated Oct. 30, 2017 for U.S. Appl. No. 13/219,874.
Notice of allowance dated Oct. 30, 2017 for U.S. Appl. No. 14/708,792.
Notice of allowance dated Dec. 12, 2017 for U.S. Appl. No. 14/707,246.
Office action dated Jan. 18, 2017 for U.S. Appl. No. 13/219,874.
Office action dated Apr. 3, 2017 for U.S. Appl. No. 14/708,792.
Office action dated Apr. 4, 2017 for U.S. Appl. No. 13/219,874.
Office action dated May 26, 2016 for U.S. Appl. No. 14/708,792.
Office action dated Jun. 6, 2014 for U.S. Appl. No. 13/219,874.
Office action dated Jun. 8, 2016 for U.S. Appl. No. 13/219,874.
Office action dated Aug. 16, 2017 for U.S. Appl. No. 14/707,246.
Office action dated Nov. 25, 2015 for U.S. Appl. No. 14/708,792.
Office action dated Nov. 27, 2015 for U.S. Appl. No. 13/219,874.
Office action dated Dec. 2, 2016 for U.S. Appl. No. 14/708,792.
Office action dated Dec. 29, 2014 for U.S. Appl. No. 13/219,874.
EP15788891.8 Supplementary European Search Report and Search Opinion dated Apr. 23, 2018.
U.S. Appl. No. 15/691,187 Office Action dated Feb. 21, 2018.
U.S. Appl. No. 15/844,367 Notice of Allowance dated Jan. 7, 2019.
U.S. Appl. No. 15/844,367 Office Action dated Sep. 5, 2018.
U.S. Appl. No. 16/148,357 Office Action dated Dec. 22, 2020.

Section 19B-19B

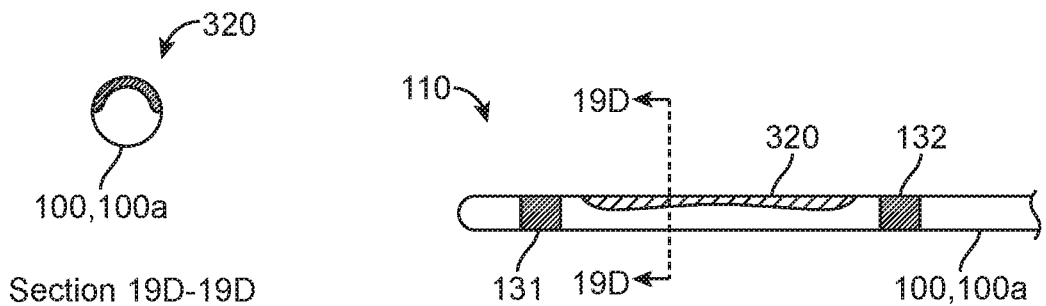
FIG. 19d
FIG. 19e
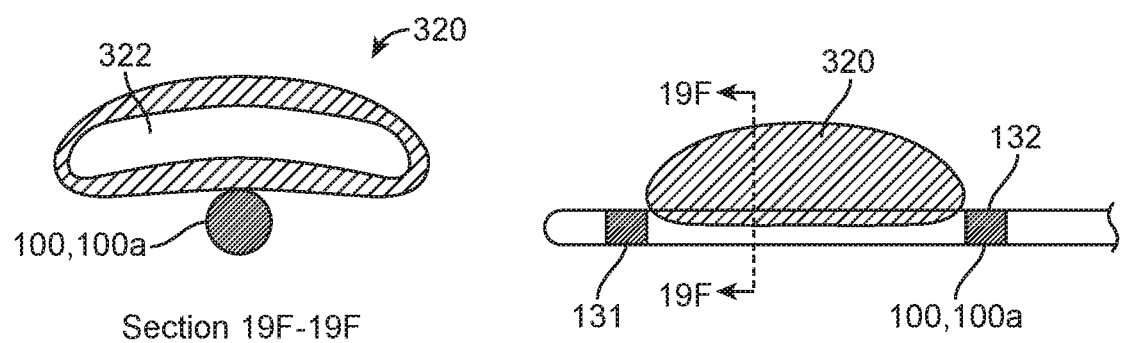
FIG. 19f
FIG. 19g
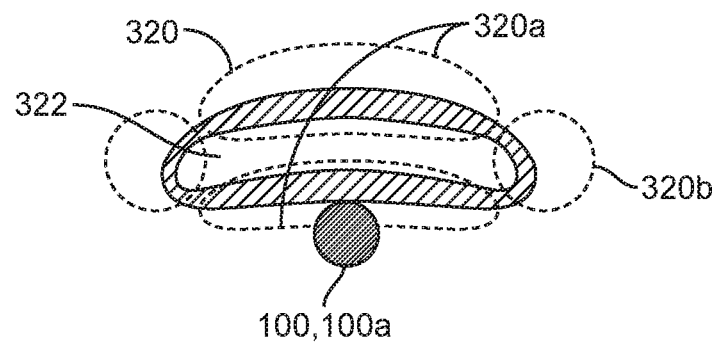
FIG. 19h

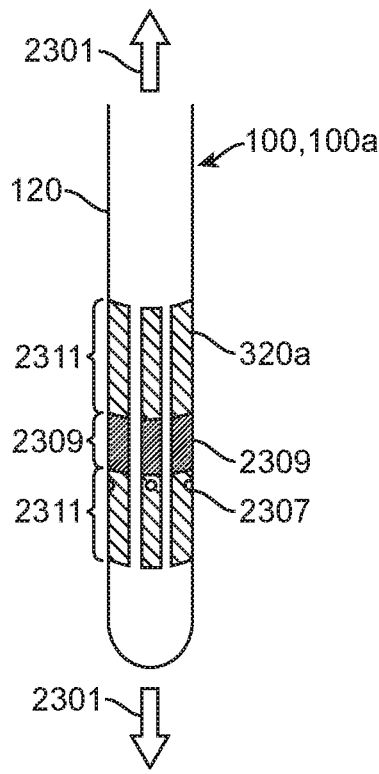
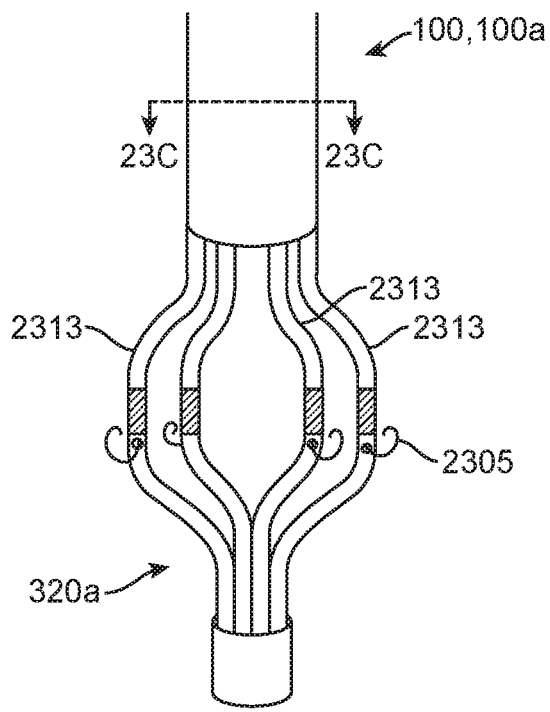
FIG. 23a  FIG. 23b
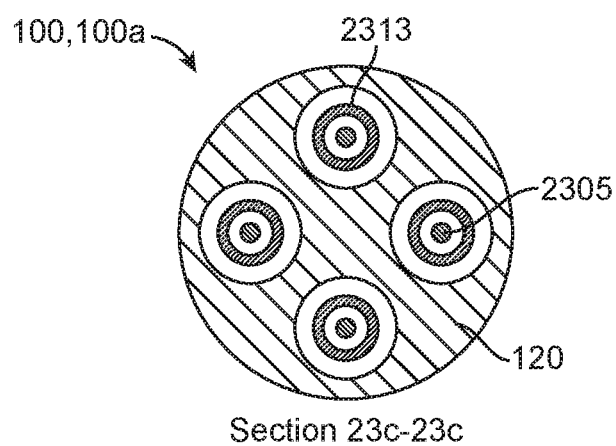
FIG. 23c

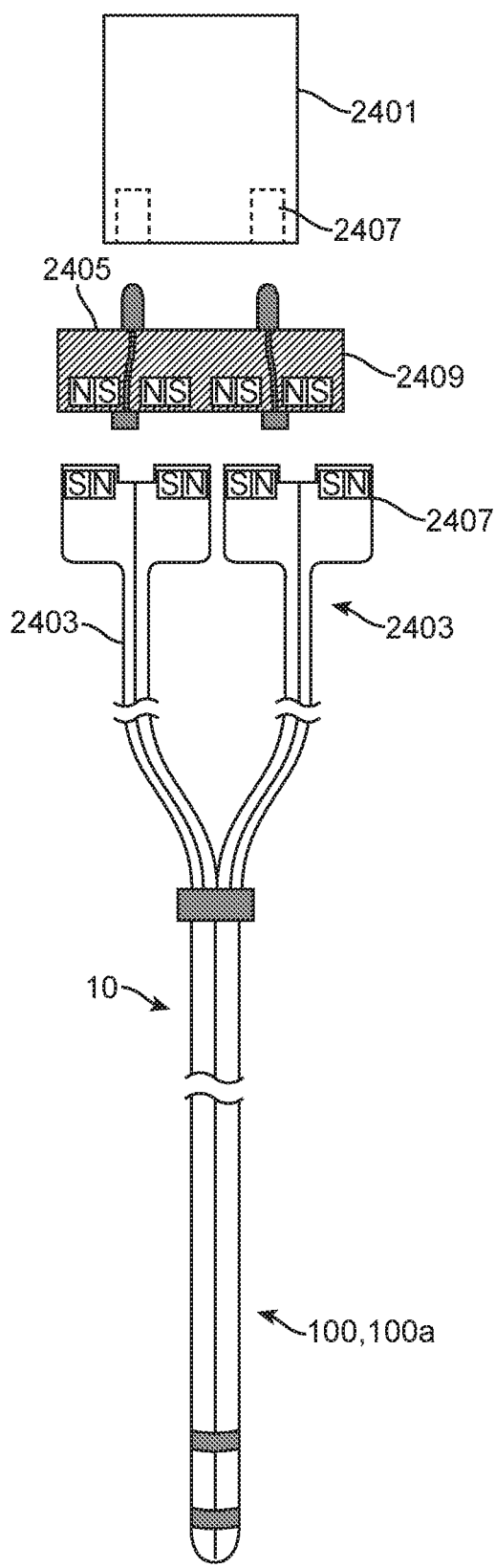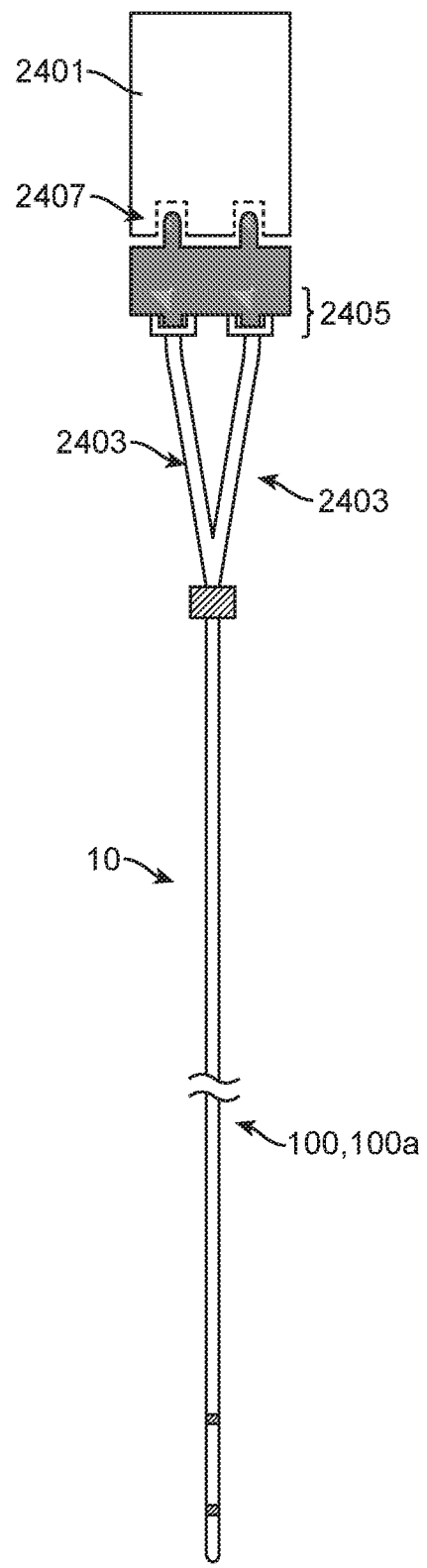
FIG. 24b
FIG. 24c

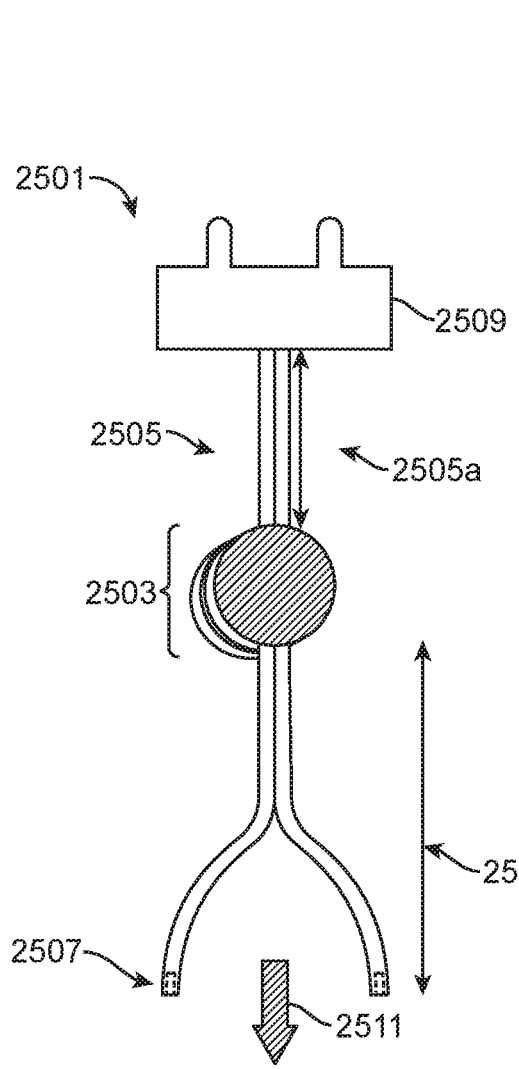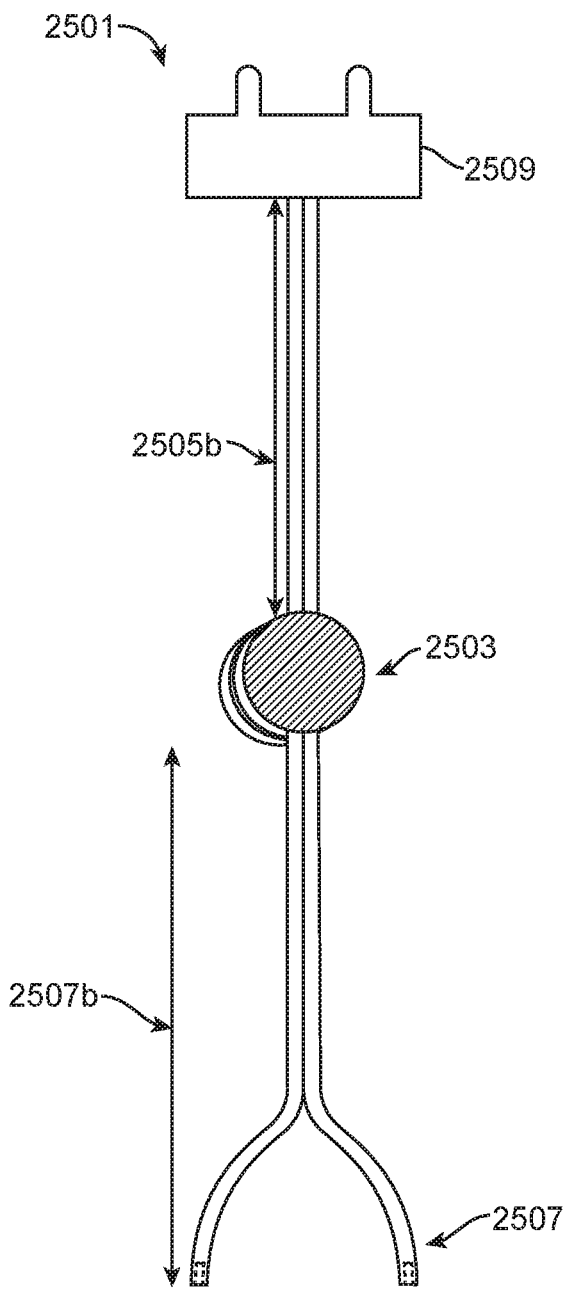
FIG. 25b
FIG. 25c

DEVICE AND METHOD FOR POSITIONING AN ELECTRODE IN A BODY CAVITY

CROSS-REFERENCE TO RELATED APPLICATIONS

This application is a continuation of U.S. patent application Ser. No. 15/844,367, filed Dec. 15, 2017, now U.S. Pat. No. 10,232,170, which is a continuation of U.S. patent application Ser. No. 14/707,246, filed May 8, 2015, now U.S. Pat. No. 9,872,981, which claims the benefit of U.S. Provisional Application No. 61/990,998, filed May 9, 2014, which applications are incorporated herein by reference.

This application is related to U.S. patent application Ser. No. 13/219,874, filed Aug. 29, 2011, entitled "Device and Method for Positioning an Electrode in Tissue" and U.S. Provisional Patent Application Nos. 61/387,185, filed Sep. 28, 2010, entitled "Rhythm Support Device 2"; 61/412,992, filed Nov. 12, 2010, entitled "Pacing Device"; 61/420,060, filed Dec. 6, 2010, entitled, "Pacing Device"; 61/427,306, filed Dec. 27, 2010, entitled "Rhythm Support Device 5"; 61/445,992, filed Feb. 23, 2011, entitled, "Pacing Device"; and 61/501,450, filed Jun. 27, 2011, entitled "Pacing Device". The full disclosures of each of these applications are incorporated by reference herein.

BACKGROUND

Field of the Disclosure.

The present disclosure relates generally to the sensing/stimulation electrode devices and methods for their use, and more specifically to novel devices and methods for more safe and reliable positioning of a sensing/stimulation electrode within body tissue.

Bradycardia (reduced heart rate) is a common condition affecting millions of patients annually. Although many such patients require implantation of permanent pacemaker devices to help regulate heart rate, other patients experience bradycardia with reversible causes that do not require permanent pacemaker implantation and may instead receive temporary bradycardia support, such as over a period of less than one week. A common treatment for temporary bradycardia support involves a system including transvenous electrode pacing leads that are inserted directly into the right ventricle of the heart to stimulate and regulate cardiac function. However, the conventional versions of these systems have several drawbacks.

Thus, there are needs in the electrode stimulation device field for new and useful devices and methods for positioning an electrode in tissue.

SUMMARY

The present disclosure provides new and useful devices and methods for positioning an electrode in tissue.

Embodiments of the present disclosure provide electrical sensing/stimulation apparatuses for positioning at least one electrode within body tissue. An electrical sensing/stimulation apparatus may comprise an elongate lead body having at least one internal lumen; at least one sensing/stimulation electrode; a deployable/retractable displacement member that moves or biases at least one electrode and/or at least one tissue attachment member towards a prescribed direction by the user; a tissue attachment mechanism for affixing the distal segment of the device to body tissue; and an atraumatic distal lead body termination. The tissue attachment mechanism may have a retracted configuration and a deployed configuration. In the retracted configuration, the mechanism may be positioned substantially within the distal segment of the lead body, and in the deployed configuration, the mechanism may extend from the axis of the lead body to engage body tissue.

Embodiments of the present disclosure provide methods for positioning an electrical sensing/stimulation device within body tissue. A method may comprise the steps of navigating an elongate lead body to a target tissue (where the elongate lead body may comprise at least one internal lumen, sensing/stimulation electrode(s), displacement member(s), tissue attachment member(s), tissue attachment deployment port(s), and an atraumatic distal tip); aligning the tissue attachment member(s) to the target tissue by using the lead's bi-directional torque control; deploying and/or expanding the displacement member(s) to bias the lead body and tissue attachment member(s) deployment ports(s) and electrode(s) against the target tissue; actuating the tissue attachment member(s) to extend from the tissue anchor deployment port(s) and into the target tissue, to affix the distal lead body and electrode(s) to the target body tissue; verifying the proper affixation of the device to the target; retracting and/or collapsing the displacement mechanism; and, retracting the tissue attachment member(s) after affixation to the target tissue, so as to release the affixation of the distal lead body and electrode(s) from the target body tissue.

Aspects of the present disclosure provide electrical sensing/stimulation apparatuses for positioning at least one electrode within body tissue. An electrical sensing/stimulation apparatus may comprise an elongate lead body, at least one sensing/stimulation electrode, a deployable/retractable displacement member, and a tissue attachment mechanism. The elongate lead body may have a longitudinal axis. The sensing/stimulation electrode(s) may be coupled to the elongate lead body. The deployable/retractable displacement member may be coupled to the elongate lead body and may be adapted to move or bias the at least one electrode towards a prescribed direction by a user. The tissue attachment mechanism may be adapted to affix a distal segment of the elongate lead body to body tissue. The tissue attachment mechanism may have a retracted configuration and a deployed configuration. In the retracted configuration, the tissue attachment mechanism may be positioned substantially within the at least one internal lumen. In the deployed configuration, the tissue attachment mechanism may extend from the longitudinal axis of the elongate lead body to engage body tissue. The tissue attachment mechanism may comprise a plurality of tissue attachment members adapted to extend from a common port of the elongate lead body. Two or more of the tissue attachment members of the plurality of tissue attachment members may be adapted to diverge from one another when extended from the common port.

The elongate lead body may have one or more ports through which the tissue attachment mechanism is configured to deploy. A proximal portion of the elongate lead body may be configured to couple with an external generator. The proximal portion of the elongate lead body may be configured to couple with the external generator through a magnetic coupling. The proximal portion of the elongate lead body may be configured to couple with the external generator through an extension coupling adapted to axially lengthen or contract.

The sensing/stimulation electrode(s) may be mounted over or embedded within an outer surface of a distal portion of the elongate lead body such that a portion of the electrode(s) can be exposed at the outer surface of the elongate lead body. The at least one sensing/stimulation electrode(s) comprises a first electrode and a second electrode. The first electrode and second electrode may be axially separated from one another. The deployable/retractable displacement member may be disposed between the first and second electrodes.

The deployable/retractable displacement member may comprise an expandable member having a collapsed configuration and an expanded configuration. The expandable member may be adapted to deploy out of a lateral side of the elongate lead body. In some embodiments, the expandable member in the collapsed configuration does not extend from an outer surface of the elongate lead body. The expandable member in the collapsed configuration may have an outer perimeter greater than an outer circumference of the elongate lead body. The expandable member may be at least partially folded onto itself in the collapsed configuration. The expandable member in the collapsed configuration may have a C-shaped, E-shaped, spiral shaped, serpentine shaped, or star shaped cross-section.

The electrical sensing/stimulation apparatus may further comprise a radiopaque marker mounted on an outer surface of the expandable member. The radiopaque marker may be expandable in conjunction with the expandable marker. The expandable member may be inflatable. The elongate lead body may have an inflation lumen to provide an inflation medium to inflate the expandable element.

The expandable member may comprise a malecot or expandable cage.

The expandable member in the expanded configuration may be shaped to match the cavity of a bodily organ or space. The bodily organ or space may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum, but is not limited to such.

In the deployed configuration, the tissue attachment mechanism may extend from the longitudinal axis of the elongate lead body to penetrate into the body tissue.

The plurality of tissue attachment members may be adapted to extend from the longitudinal axis of the elongate lead body. One or more tissue attachment member of the plurality of tissue attachment members may comprise a curved loop. Two or more tissue attachment members of the plurality of tissue attachment members may be configured to extend from different ports of the elongate lead body. Two or more of the tissue attachment members of the plurality of tissue attachment members may be adapted to be co-planar when extended.

The common port may have a length allowing the elongate lead body to translate over a linear portion of one or more of the tissue attachment members. One or more of the tissue attachment members may have a distal wire loop and a straightened distal-most portion distal of the distal wire loop.

Two or more of the tissue attachment members diverge from one another by an angle of less than or equal to 270 degrees, less than or equal to 180 degrees, less than or equal to 90 degrees, to name a few examples.

The tissue attachment member(s) may comprise a hollow needle having an inner lumen through which one or more anchoring elements are advanced from when the at least one tissue attachment member is deployed.

The electrical sensing/stimulation apparatus may further comprise an atraumatic distal lead body termination. A distal end of the elongate lead body may comprise the atraumatic distal lead body termination. The atraumatic distal lead body termination may comprise a sensing/stimulation electrode. The atraumatic distal lead body termination may have a rounded, cobra-head, an elbowed, a bilateral eccentric, or a quad-eccentric tip, to name few examples. The atraumatic distal lead body termination may comprises a plurality of radially extending outward tines.

The electrical sensing/stimulation apparatus may further comprise a proximal handle coupled to the elongate lead body. The proximal handle may comprise one or more controls for one or more of activating the at least one sensing/stimulation electrode, deploying or retracting the deployable/retractable displacement member, or deploying or retracting the tissue attachment mechanism. The proximal handle may comprise one or more displays for indicating one or more of a relative position of the tissue attachment mechanism, a sensed resistance of tissue engaged by the tissue attachment mechanism, or a sensed amount of current through the tissue engaged by the tissue attachment mechanism.

The elongate lead body may have an internal lumen and the electrical sensing/stimulation apparatus may further comprise a torque member within the inner lumen and adapted to torque the elongate lead body. The torque member may be fixedly attached to the elongate lead body. The torque member may comprise a hypotube. The electrical sensing/stimulation apparatus may further comprise a shaping wire configured for placement within the internal lumen of the elongate lead body to provide a predetermined shape to the elongate lead body. The shaping wire may be configured to axially translate and/or rotate within the inner lumen. The shaping wire may be removable from the inner lumen. The shaping wire may be fixed within the inner lumen. The elongate lead body may be rotatable about the shaping wire.

The elongate lead body may comprise an O-ring disposed in a proximal portion thereof. The O-ring may be adapted to prevent fluid from leaking proximally therethrough.

The plurality of tissue attachment members may have elongate proximal portions disposed within the elongate lead body when the tissue attachment mechanism is both retracted and deployed. The elongate proximal portions of the tissue attachment members may be housed within an outer covering having a shape to provide an interference fit within the elongate lead body.

Aspects of the present disclosure also provide methods for positioning an electrical sensing/stimulation device within body tissue. An elongate lead body of the electrical sensing/stimulation device may be advanced to position the elongate lead body at a target site in a bodily cavity. The elongate lead body may be torqued to align at least one tissue attachment member of the electrical sensing/stimulation device with a target tissue in the target site. A displacement member may be deployed to bias the elongate lead body and the at least one tissue attachment member against the target tissue. The tissue attachment member(s) may be actuated to extend from at least one tissue anchor deployment port on the elongate lead body and into the target tissue to affix a distal portion of the elongate lead body and the electrode(s) of the electrical sensing/stimulation device to the target tissue. The tissue attachment member(s) may comprise a plurality of tissue attachment members. The plurality of tissue attachment members may be actuated to extend from a common tissue deployment port. Two or more attachment members may diverge from one another when deployed from the common tissue deployment port.

Proper affixation of the distal portion of the elongate lead body to the target tissue may be verified, such as by fluoroscopically imaging the bodily cavity with the elongate lead body positioned therein. In fluoroscopically imaging the bodily cavity, one or more radiopaque markers coupled to one or more of the elongate lead body, the tissue attachment member(s), or the displacement member may be identified.

A physiological parameter, such as cardiac electrical activity or blood pressure, may be sensed with the electrode(s) affixed to the target tissue and/or the target tissue may be electrically stimulated with the electrode(s).

The displacement member may be collapsed and the tissue attachment member may be retracted after affixation to the target tissue, so as to release the affixation of the distal portion of the elongate lead body and the electrode(s) from the target tissue.

To advance the elongate lead body, an internal shaping wire may be positioned through an internal lumen of the elongate lead body to impart a predetermined shape to the elongate lead body. The predetermined shape may facilitate advancement of the elongate lead body through a bodily lumen.

To torque the elongate lead body, a torque member may be disposed within an internal lumen of the elongate lead body. The displacement member may be deployed from a lateral side of the elongate lead body. The displacement member may be expanded, such as to a shape matching a shape of the bodily cavity. The displacement member may comprise an expandable member and the displacement member may be deployed by inflating the expandable member.

Two or more tissue attachment members of the plurality of tissue attachment members may be deployed from different tissue deployment ports. The two or more attachment members may be coplanar with one another when deployed from the different tissue deployment ports. The two or more tissue attachment members may deploy with an angle between the deployment planes of the tissue attachment members.

The tissue attachment member(s) may extend from a longitudinal axis of the elongate lead body when deployed. A proximal portion of the elongate lead body may be coupled with an external generator. The proximal portion of the elongate lead body may be coupled with the external generator through a magnetic coupling. The proximal portion of the elongate lead body may be coupled with the external generator through an extension coupling adapted to axially lengthen or contract. A movement of the affixed tissue attachment member(s) relative to the elongate lead body may be sensed. The sensed movement may be displayed on a handle coupled to the elongate lead body.

The target bodily cavity may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum.

Aspects of the present disclosure may also provide further electrical sensing/stimulation apparatuses for positioning at least one electrode within body tissue. An electrical sensing/stimulation apparatus may comprise an elongate lead body, at least one sensing/stimulation electrode, an expandable displacement member, and a tissue attachment mechanism. The elongate lead body having a longitudinal axis. The sensing/stimulation electrode may be coupled to the elongate lead body. The expandable displacement member may be coupled to the elongate lead body and adapted to move or bias the at least one electrode towards a prescribed direction by a user. The expandable displacement member may have a shape matching a cavity of a bodily organ or space when expanded. The tissue attachment mechanism may be adapted to affix a distal segment of the elongate lead body to body tissue. The tissue attachment mechanism may have a retracted configuration and a deployed configuration. In the retracted configuration, the tissue attachment mechanism may be positioned substantially within the at least one internal lumen. In the deployed configuration, the tissue attachment mechanism may extend from the longitudinal axis of the elongate lead body to engage body tissue.

The sensing/stimulation electrode(s) may comprise a first electrode and a second electrode, which may be axially separated from one another, such that the expandable displacement member is disposed between the first and second electrodes, for example.

In many embodiments, the expandable member when collapsed does not extend from an outer surface of the elongate lead body. The expandable member when collapsed may have an outer perimeter greater than an outer circumference of the elongate lead body. The expandable displacement member may at least partially fold onto itself in the collapsed configuration. The expandable member in the collapsed configuration may have a C-shaped, E-shaped, spiral shaped, serpentine shaped, or star shaped cross-section. A radiopaque marker may be mounted on an outer surface of the expandable displacement member. The radiopaque marker may be expandable in conjunction with the expandable member. The expandable displacement member may be inflatable. The elongate lead body may have an inflation lumen to provide an inflation medium to inflate the expandable displacement member. Alternatively or in combination, the expandable displacement member may comprise a malecot or expandable cage. The bodily organ or space that matches the shape of the expanded expandable displacement member may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum, to name a few.

The elongate lead body may have one or more ports through which the tissue attachment mechanism is configured to deploy.

A proximal portion of the elongate lead body may be configured to couple with an external generator. The proximal portion of the elongate lead body may be configured to couple with the external generator through a magnetic coupling. The proximal portion of the elongate lead body may be configured to couple with the external generator through an extension coupling adapted to axially lengthen or contract.

In the deployed configuration, the tissue attachment mechanism may extend from the longitudinal axis of the elongate lead body to penetrate into the body tissue. The plurality of tissue attachment members may be adapted to extend from the longitudinal axis of the elongate lead body. One or more tissue attachment member of the plurality of tissue attachment members comprises a curved loop. Two or more tissue attachment members of the plurality of tissue attachment members may be configured to extend from different ports of the elongate lead body. The two or more of the tissue attachment members of the plurality of tissue attachment members may be adapted to be co-planar when extended.

A port through which the tissue attachment mechanism deploys may have a length allowing the elongate lead body to translate over a linear portion of one or more of the tissue attachment members. One or more of the tissue attachment members may have a distal wire loop and a straightened distal-most portion distal of the distal wire loop.

Two or more of the tissue attachment members may diverge from one another by an angle of less than or equal to 270 degrees, less than or equal to 180 degrees, less than or equal to 90 degrees, to name a few examples. The tissue attachment member may comprise a hollow needle having an inner lumen through which one or more anchoring elements are advanced from when the at least one tissue attachment member is deployed.

The electrical sensing/stimulation apparatus may further comprise an atraumatic distal lead body termination. A distal end of the elongate lead body may comprise the atraumatic distal lead body termination. The atraumatic distal lead body termination may comprise a sensing/stimulation electrode. The atraumatic distal lead body termination may have a rounded, cobra-head, an elbowed, a bilateral eccentric, or a quad-eccentric tip, to name a few examples. The atraumatic distal lead body termination may comprise a plurality of radially extending outward tines.

The electrical sensing/stimulation apparatus may further comprise a proximal handle coupled to the elongate lead body. The proximal handle may comprise one or more controls for one or more of activating the at least one sensing/stimulation electrode, deploying or retracting the deployable/retractable displacement member, or deploying or retracting the tissue attachment mechanism. The proximal handle may comprise one or more displays for indicating one or more of a relative position of the tissue attachment mechanism, a sensed resistance of tissue engaged by the tissue attachment mechanism, or a sensed amount of current through the tissue engaged by the tissue attachment mechanism.

The elongate lead body may have an internal lumen, and the electrical sensing/stimulation apparatus may further comprise a torque member within the inner lumen and adapted to torque the elongate lead body. The torque member may be fixedly attached to the elongate lead body. The torque member may comprise a hypotube or tubular braided wire construction laminated with polymer. The electrical sensing/stimulation apparatus may further comprise a shaping wire configured for placement within the internal lumen of the elongate lead body to provide a predetermined shape to the elongate lead body. The shaping wire may be configured to axially translate and/or rotate within the inner lumen. The shaping wire may be removable from the inner lumen. The shaping wire may be fixed within the inner lumen. The elongate lead body may be rotatable about the shaping wire.

The elongate lead body may comprise an O-ring disposed in a proximal portion thereof. The O-ring may be adapted to prevent fluid from leaking proximally therethrough.

The plurality of tissue attachment members may have elongate proximal portions disposed within the elongate lead body when the tissue attachment mechanism is both retracted and deployed. The elongate proximal portions of the tissue attachment members may be housed within an outer covering having a shape to provide an interference fit within the elongate lead body.

Aspects of the present disclosure may provide a method for positioning an electrical sensing/stimulation device within body tissue. An elongate lead body of the electrical sensing/stimulation device may be advanced to position the elongate lead body at a target site in a bodily cavity. The elongate lead body may be torqued to align at least one tissue attachment member of the electrical sensing/stimulation device with a target tissue in the target site. A displacement member may be expanded to bias the elongate lead body and the at least one tissue attachment member against the target tissue, the expanded displacement member having a shape that may match the bodily cavity. At least one tissue attachment member may be actuated to extend from at least one tissue anchor deployment port on the elongate lead body and into the target tissue to affix a distal portion of the elongate lead body and at least one electrode of the electrical sensing/stimulation device to the target tissue.

After affixation to the target tissue, the displacement member may be collapsed and the at least one tissue attachment member may be retracted so as to release the affixation of the distal portion of the elongate lead body and the at least one electrode from the target tissue.

The displacement member may be expanded outwardly from a lateral side of the elongate lead body.

The displacement member may comprise an expandable element and the displacement member may be deployed by inflating the expandable member.

The bodily organ or space that matches the shape of the expanded expandable displacement member may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum, to name a few.

Proper affixation of the distal portion of the elongate lead body to the target tissue may be verified, such as by fluoroscopically imaging the bodily cavity with the elongate lead body positioned therein. In fluoroscopically imaging the bodily cavity, one or more radiopaque markers coupled to one or more of the elongate lead body, the at least one tissue attachment member, or the displacement member may be identified.

A physiological parameter, such as cardiac electrical activity or blood pressure, may be sensed with the electrode(s) affixed to the target tissue and/or the target tissue may be electrically stimulated with the electrode(s).

To advance the elongate lead body, an internal shaping wire may be positioned through an internal lumen of the elongate lead body to impart a predetermined shape to the elongate lead body. The predetermined shape may facilitate advancement of the elongate lead body through a bodily lumen.

To torque the elongate lead body, a torque member may be disposed within an internal lumen of the elongate lead body. The displacement member may be deployed from a lateral side of the elongate lead body. The displacement member may be expanded, such as to a shape matching a shape of the bodily cavity. The displacement member may comprise an expandable member and the displacement member may be deployed by inflating the expandable member.

Two or more tissue attachment members of the plurality of tissue attachment members may be deployed from different tissue deployment ports. The two or more attachment members may be coplanar with one another when deployed from the different tissue deployment ports, or the deployment planes of the loops of the tissue attachment members may be configured with an angle separating them. The two or more tissue attachment members may deploy with an angle between the deployment planes of the tissue attachment members.

The tissue attachment member(s) may extend from a longitudinal axis of the elongate lead body when deployed. A proximal portion of the elongate lead body may be coupled with an external generator. The proximal portion of the elongate lead body may be coupled with the external generator through a magnetic coupling. The proximal portion of the elongate lead body may be coupled with the external generator through an extension coupling adapted to axially lengthen or contract. A movement of the affixed tissue attachment member(s) relative to the elongate lead body may be sensed. The sensed movement may be displayed on a handle coupled to the elongate lead body. The bodily cavity may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum.

Aspects of the present disclosure may also provide an electrical sensing/stimulation apparatus for positioning at least one electrode within body tissue. The electrical sensing/stimulation apparatus may comprise an elongate lead body, at least one sensing/stimulation electrode, a deployable/retractable displacement member, a tissue attachment mechanism, and a shaping wire. The elongate lead body may have a longitudinal axis. The sensing/stimulation electrode(s) may be coupled to the elongate lead body. The deployable/retractable displacement member may be coupled to the elongate lead body and may be adapted to move or bias the electrode(s) towards a prescribed direction by a user. The tissue attachment mechanism may be adapted to affix a distal segment of the elongate lead body to body tissue. The tissue attachment mechanism may have a retracted configuration and a deployed configuration. In the retracted configuration, the tissue attachment mechanism may be positioned substantially within the at least one internal lumen. In the deployed configuration, the tissue attachment mechanism may extend from the longitudinal axis of the elongate lead body to engage body tissue. The shaping wire may be configured for placement within an internal lumen of the elongate lead body to provide a predetermined shape to the elongate lead body.

The shaping wire may be configured to axially translate and/or rotate within the inner lumen. The shaping wire may be removable from the inner lumen. The shaping wire may be fixed within the inner lumen. The elongate lead body may be rotatable about the shaping wire.

The electrical sensing/stimulation apparatus may further comprise a torque member within the inner lumen adapted to torque the elongate lead body. The shaping wire may be configured to be disposed within the torque member. The shaping wire may be selectively curved by the user.

The elongate lead body may have one or more ports through which the tissue attachment mechanism is configured to deploy. A proximal portion of the elongate lead body may be configured to couple with an external generator. The proximal portion of the elongate lead body may be configured to couple with the external generator through a magnetic coupling. The proximal portion of the elongate lead body may be configured to couple with the external generator through an extension coupling adapted to axially lengthen or contract.

The sensing/stimulation electrode(s) may be mounted over or embedded within an outer surface of a distal portion of the elongate lead body such that a portion of the electrode(s) can be exposed at the outer surface of the elongate lead body. The at least one sensing/stimulation electrode(s) comprises a first electrode and a second electrode. The first electrode and second electrode may be axially separated from one another. The deployable/retractable displacement member may be disposed between the first and second electrodes.

The deployable/retractable displacement member may comprise an expandable member having a collapsed configuration and an expanded configuration. The expandable member may be adapted to deploy out of a lateral side of the elongate lead body. In some embodiments, the expandable member in the collapsed configuration does not extend from an outer surface of the elongate lead body. The expandable member in the collapsed configuration may have an outer perimeter greater than an outer circumference of the elongate lead body. The expandable member may be at least partially folded onto itself in the collapsed configuration. The expandable member in the collapsed configuration may have a C-shaped, E-shaped, spiral shaped, serpentine shaped, or star shaped cross-section.

The electrical sensing/stimulation apparatus may further comprise a radiopaque marker mounted on or embedded within an outer surface of the expandable member. The radiopaque marker may be expandable in conjunction with the expandable marker. The expandable member may be inflatable. The elongate lead body may have an inflation lumen to provide an inflation medium to inflate the expandable element.

The expandable member may comprise a malecot or expandable cage

In the deployed configuration, the tissue attachment mechanism may extend from the longitudinal axis of the elongate lead body to penetrate into the body tissue.

The plurality of tissue attachment members may be adapted to extend from the longitudinal axis of the elongate lead body. One or more tissue attachment member of the plurality of tissue attachment members may comprise a curved loop. Two or more tissue attachment members of the plurality of tissue attachment members may be configured to extend from different ports of the elongate lead body. Two or more of the tissue attachment members of the plurality of tissue attachment members may be adapted to be co-planar when extended. Two or more tissue attachment members of the plurality of tissue attachment members may be configured to extend from a common port of the elongate body. Two or more of the tissue attachment members of the plurality of tissue attachment members may be adapted such that the plane of deployment of the tissue attachment members may be at an angle to each other when extended.

A port through which the tissue attachment mechanism deploys may have a length allowing the elongate lead body to translate over a linear portion of one or more of the tissue attachment members. One or more of the tissue attachment members have a distal wire loop and a straightened distal-most portion distal of the distal wire loop.

Two or more of the tissue attachment members diverge from one another by an angle of less than or equal to 270 degrees, less than or equal to 180 degrees, less than or equal to 90 degrees, to name a few examples.

The tissue attachment member(s) may comprise a hollow needle having an inner lumen through which one or more anchoring elements are advanced from when the at least one tissue attachment member is deployed.

The electrical sensing/stimulation apparatus may further comprise an atraumatic distal lead body termination. A distal end of the elongate lead body may comprise the atraumatic distal lead body termination. The atraumatic distal lead body termination may comprise a sensing/stimulation electrode. The atraumatic distal lead body termination may have a rounded, cobra-head, an elbowed, a bilateral eccentric, or a quad-eccentric tip, to name few examples. The atraumatic distal lead body termination may comprises a plurality of radially extending outward tines.

The electrical sensing/stimulation apparatus may further comprise a proximal handle coupled to the elongate lead body. The proximal handle may comprise one or more controls for one or more of activating the at least one sensing/stimulation electrode, deploying or retracting the deployable/retractable displacement member, or deploying or retracting the tissue attachment mechanism. The proximal handle may comprise one or more displays for indicating one or more of a relative position of the tissue attachment mechanism, a sensed resistance of tissue engaged by the tissue attachment mechanism, or a sensed amount of current through the tissue engaged by the tissue attachment mechanism.

The elongate lead body may have an internal lumen and the electrical sensing/stimulation apparatus may further comprise a torque member within an inner lumen of the elongate lead body and adapted to torque the elongate lead body. The torque member may be fixedly attached to the elongate lead body. The torque member may comprise a hypotube or a wire braided tubular structure laminated with polymer. The electrical sensing/stimulation apparatus may further comprise a shaping wire configured for placement within the internal lumen of the elongate lead body to provide a predetermined shape to the elongate lead body. The shaping wire may be configured to axially translate and/or rotate within the inner lumen. The shaping wire may be removable from the inner lumen. The shaping wire may be fixed within the inner lumen. The elongate lead body or torque member may be rotatable about the shaping wire.

The elongate lead body may comprise an O-ring disposed in a proximal portion thereof. The O-ring may be adapted to prevent fluid from leaking proximally therethrough.

The plurality of tissue attachment members may have elongate proximal portions disposed within the elongate lead body when the tissue attachment mechanism is both retracted and deployed. The elongate proximal portions of the tissue attachment members may be housed within an outer covering having a shape to provide an interference fit within the elongate lead body.

Aspects of the present disclosure may also provide methods for positioning an electrical sensing/stimulation device within body tissue. An elongate lead body of the electrical sensing/stimulation device may be advanced to position the elongate lead body at a target site in a bodily cavity. An internal shaping wire may be affixed within or advanced axially and positioned through an internal lumen of the elongate lead body to impart a predetermined shape to the elongate lead body, thereby facilitating advancement of the elongate lead body through a bodily lumen. The elongate lead body may be torqued to align at least one tissue attachment member of the electrical sensing/stimulation device with a target tissue in the target site. A displacement member may be deployed to bias the elongate lead body and the tissue attachment member(s) against the target tissue. The tissue attachment member(s) may be actuated to extend from at least one tissue anchor deployment port on the elongate lead body and into the target tissue to affix a distal portion of the elongate lead body and electrode(s) of the electrical sensing/stimulation device to the target tissue.

Proper affixation of the distal portion of the elongate lead body to the target tissue may be verified, such as by fluoroscopically imaging the bodily cavity with the elongate lead body positioned therein. In fluoroscopically imaging the bodily cavity, one or more radiopaque markers coupled to one or more of the elongate lead body, the tissue attachment member(s), or the displacement member may be identified.

A physiological parameter, such as cardiac electrical activity or blood pressure, may be sensed with the electrode(s) affixed to the target tissue and/or the target tissue may be electrically stimulated with the electrode(s).

The displacement member may be collapsed and the tissue attachment member(s) may be retracted after affixation to the target tissue, so as to release the affixation of the distal portion of the elongate lead body and the electrode(s) from the target tissue.

An internal shaping wire may be positioned through an internal lumen of the elongate lead body to impart a predetermined shape to the elongate lead body, for example, to facilitate advancement of the elongate lead body through a bodily lumen.

To torque the elongate lead body, a torque member may be disposed within an internal lumen of the elongate lead body. The displacement member may be deployed from a lateral side of the elongate lead body. The displacement member may be expanded, such as to a shape matching a shape of the bodily cavity. The displacement member may comprise an expandable member and the displacement member may be deployed by inflating the expandable member.

Two or more tissue attachment members of the plurality of tissue attachment members may be deployed from different tissue deployment ports, or from a common deployment port. The two or more attachment members may be coplanar with one another when deployed from the different tissue deployment ports. The two or more tissue attachment members may deploy with an angle between the deployment planes of the tissue attachment members or the tissue attachment members may be deployed at an angle to each other.

The tissue attachment member(s) may extend from a longitudinal axis of the elongate lead body when deployed. A proximal portion of the elongate lead body may be coupled with an external generator. The proximal portion of the elongate lead body may be coupled with the external generator through a magnetic coupling. The proximal portion of the elongate lead body may be coupled with the external generator through an extension coupling adapted to axially lengthen or contract. A movement of the affixed tissue attachment member(s) relative to the elongate lead body may be sensed. The sensed movement may be displayed on a handle coupled to the elongate lead body.

The target bodily cavity may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum. Aspects of the present disclosure may also provide electrical sensing/stimulation apparatuses for positioning at least one electrode within body tissue. The electrical sensing/stimulation apparatus may comprise an elongate lead body, at least one sensing/stimulation electrode, a deployable/retractable displacement member, a tissue attachment mechanism, and a torque member. The elongate lead body may have a longitudinal axis and an inner lumen. The sensing/stimulation electrode may be coupled to the elongate lead body. The deployable/retractable displacement member may be coupled to the elongate lead body and adapted to move or bias the at least one electrode and/or the at least one attachment member towards a prescribed direction by a user. The tissue attachment mechanism may be adapted to affix a distal segment of the elongate lead body to body tissue. The tissue attachment mechanism may have a retracted configuration and a deployed configuration. In the retracted configuration, the tissue attachment mechanism may be positioned substantially within the at least one internal lumen. In the deployed configuration, the tissue attachment mechanism may extend from the longitudinal axis of the elongate lead body to engage body tissue. The torque member may be positioned within the inner lumen of the elongate lead body adapted to torque the elongate lead body.

The torque member may be fixedly attached to the elongate lead body. The torque member may comprise a hypotube or a braided wire tubular structure laminated with polymer. The elongate lead body may have one or more ports through which the tissue attachment mechanism is configured to deploy. A proximal portion of the elongate lead body may be configured to couple with an external generator. The proximal portion of the elongate lead body may be configured to couple with the external generator through a magnetic coupling. The proximal portion of the elongate lead body may be configured to couple with the external generator through an extension coupling adapted to axially lengthen or contract.

The sensing/stimulation electrode(s) may be mounted over or embedded within an outer surface or embedded within the surface of a distal portion of the elongate lead body such that a portion of the electrode can be exposed at the outer surface of the elongate lead body. The at least one sensing/stimulation electrode(s) comprises a first electrode and a second electrode. The first electrode and second electrode may be axially separated from one another. The deployable/retractable displacement member may be disposed between the first and second electrodes.

The deployable/retractable displacement member may comprise an expandable member having a collapsed configuration and an expanded configuration. The expandable member may be adapted to deploy out of a lateral side of the elongate lead body. In some embodiments, the expandable member in the collapsed configuration does not extend from an outer surface of the elongate lead body. The expandable member in the collapsed configuration may have an outer perimeter greater than an outer circumference of the elongate lead body. The expandable member may be at least partially folded onto itself in the collapsed configuration. The expandable member in the collapsed configuration may have a C-shaped, E-shaped, spiral shaped, serpentine shaped, or star shaped cross-section.

The electrical sensing/stimulation apparatus may further comprise a radiopaque marker mounted on an outer surface of the expandable member. The radiopaque marker may be expandable in conjunction with the expandable marker. The expandable member may be inflatable. The elongate lead body may have an inflation lumen to provide an inflation medium to inflate the expandable member.

The expandable member may comprise a malecot or expandable cage.

In the deployed configuration, the tissue attachment mechanism may extend from the longitudinal axis of the elongate lead body to penetrate into the body tissue.

The plurality of tissue attachment members may be adapted to extend from the longitudinal axis of the elongate lead body. One or more tissue attachment member of the plurality of tissue attachment members may comprise a curved loop. Two or more tissue attachment members of the plurality of tissue attachment members may be to extend from different ports of the elongate lead body. Two or more of the tissue attachment members of the plurality of tissue attachment members may be adapted to be co-planar when extended or their deployment planes may be angled to each other.

The common port may have a length allowing the elongate lead body to translate over a linear portion of one or more of the tissue attachment members. One or more of the tissue attachment members may have a distal wire loop and a straightened distal-most portion distal of the distal wire loop.

Two or more of the tissue attachment members diverge from one another by an angle of less than or equal to 270 degrees, less than or equal to 180 degrees, less than or equal to 90 degrees, to name a few examples.

The tissue attachment member(s) may comprise a hollow needle having an inner lumen through which one or more anchoring elements are advanced from when the at least one tissue attachment member is deployed.

The electrical sensing/stimulation apparatus may further comprise an atraumatic distal lead body termination. A distal end of the elongate lead body may comprise the atraumatic distal lead body termination. The atraumatic distal lead body termination may comprise a sensing/stimulation electrode. The atraumatic distal lead body termination may have a rounded, cobra-head, an elbowed, a bilateral eccentric, or a quad-eccentric tip, to name few examples. The atraumatic distal lead body termination may comprises a plurality of radially extending outward tines.

The electrical sensing/stimulation apparatus may further comprise a proximal handle coupled to the elongate lead body. The proximal handle may comprise one or more controls for one or more of activating the at least one sensing/stimulation electrode, deploying or retracting the deployable/retractable displacement member, or deploying or retracting the tissue attachment mechanism. The proximal handle may comprise one or more displays for indicating one or more of a relative position of the tissue attachment mechanism, a sensed resistance of tissue engaged by the tissue attachment mechanism, or a sensed amount of current through the tissue engaged by the tissue attachment mechanism.

The elongate lead body may comprise an O-ring disposed in a proximal portion thereof. The O-ring may be adapted to prevent fluid from leaking proximally therethrough.

The plurality of tissue attachment members may have elongate proximal portions disposed within the elongate lead body when the tissue attachment mechanism is both retracted and deployed. The elongate proximal portions of the tissue attachment members may be housed within an outer covering having a shape to provide an interference fit within the elongate lead body.

Aspects of the present disclosure may provide methods for positioning an electrical sensing/stimulation device within body tissue. An elongate lead body of the electrical sensing/stimulation device may be advanced to position the elongate lead body at a target site in a bodily cavity. A torque member disposed within an inner lumen of the elongate lead body may be torqued to torque or axially rotate the elongate lead body to align at least one tissue attachment member of the electrical sensing/stimulation device with a target tissue in the target site. A displacement member may be deployed to bias the elongate lead body and the tissue attachment member(s) against the target tissue. The tissue attachment member may be actuated to extend from at least one tissue anchor deployment port on the elongate lead body and into the target tissue to affix a distal portion of the elongate lead body and the electrode(s) of the electrical sensing/stimulation device to the target tissue.

Proper affixation of the distal portion of the elongate lead body to the target tissue may be verified, such as by fluoroscopically imaging the bodily cavity with the elongate lead body positioned therein. In fluoroscopically imaging the bodily cavity, one or more radiopaque markers coupled to one or more of the elongate lead body, the tissue attachment member(s), or the displacement member may be identified.

A physiological parameter, such as cardiac electrical activity or blood pressure, may be sensed with the electrode(s) affixed to the target tissue and/or the target tissue may be electrically stimulated with the electrode(s).

The displacement member may be collapsed and the tissue attachment member may be retracted after affixation to the target tissue, so as to release the affixation of the distal portion of the elongate lead body and the electrode(s) from the target tissue.

The displacement member may be deployed from a lateral side of the elongate lead body, such as by expanding the displacement member. The displacement member may be expanded to a shape matching a shape of the bodily cavity. The displacement member may comprise an expandable member and the displacement member may be deployed by inflating the expandable member. Two or more tissue attachment members of the plurality of tissue attachment members may be deployed from different tissue deployment ports or from a common deployment port. The two or more attachment members may be coplanar with one another when deployed from the different tissue deployment ports or the common delivery port, or the planes of the tissue attachment members may be deployed at an angle to each other. The two or more tissue attachment members may deploy with an angle between the deployment planes of the tissue attachment members.

At least one tissue attachment member may extend from a longitudinal axis of the elongate lead body when deployed. A proximal portion of the elongate lead body may be coupled with an external generator. The proximal portion of the elongate lead body may be coupled with the external generator through a magnetic coupling. The proximal portion of the elongate lead body may be coupled with the external generator through an extension coupling adapted to axially lengthen or contract. A movement of the affixed tissue attachment member(s) relative to the elongate lead body may be sensed. The sensed movement may be displayed on a handle coupled to the elongate lead body.

The target bodily cavity may be at least a part of a right ventricle, a left ventricle, a right atrium, a left atrium, an aorta, a vena cava, an artery, a vein, a bladder, a ureter, a uterus, a nasal cavity, an oral cavity, an esophagus, a stomach, an intestine, a gall bladder, a colon, or a rectum.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles may not be drawn to scale, and some of these elements may be arbitrarily enlarged and positioned to improve drawing legibility. Further, the particular shapes of the elements as drawn, are not intended to convey any information regarding the actual shape of the particular elements, and have been solely selected for ease of recognition in the drawings. A better understanding of the features and advantages of the present disclosure will be obtained by reference to the following detailed description that sets forth illustrative embodiments, in which the principles of the disclosure are utilized, and the accompanying drawings.

FIG. 3a shows a side, perspective view of the Inflatable Element Cartridge.

FIG. 3a' shows a section view of the Inflatable Element Cartridge with the Balloon in a collapsed configuration.

FIG. 3a" shows a section view of the Inflatable Element Cartridge with the Balloon in an expanded configuration.

FIG. 3b show a side view of the Inflatable Element Cartridge separated from the Distal Lead Body.

FIG. 3c shows a side view of the Inflatable Element Cartridge coupled to the Distal Lead Body.

FIG. 4a shows a side view of the Distal Lead Body.

FIG. 4b shows a side view of an Inflatable Displacement Member.

FIG. 4c shows a side view of the Inflatable Displacement Member separated from the Distal Lead Body.

FIG. 4d shows a side view of the Inflatable Displacement Member coupled to the Distal Lead Body.

FIG. 5a shows a side view of the Cartridge.

FIG. 5b shows a side view the Inflatable Displacement Member.

FIG. 5c shows a side view of the Cartridge mounted Inflatable Displacement Member.

FIG. 5d shows a side view of the Cartridge mounted Inflatable Displacement Member separated from the Distal Lead Body.

FIG. 5e shows a side view of the Cartridge Mounted Inflatable Displacement Member coupled to the Distal Lead Body.

FIG. 6a' shows a perspective view of other Tissue Attachment Members, wherein these Tissue Attachment Members may be deployed by retracting an actuation wire.

FIG. 7b' shows a side view of the Distal Lead Segment of FIG. 7a showing the Distal Lead Segment with the Tissue Anchors in their retracted configuration, and various shapes of the electrode to provide radiographic orientation of the Distal Lead Segment.

FIG. 8a shows a perspective view of a Distal Tip.
FIG. 8b shows a perspective view of another Distal Tip.
FIG. 8c shows a perspective view of another Distal Tip.
FIG. 8d shows a perspective view of another Distal Tip.

FIG. 10b shows a magnified view of the rotating face plate of the Lead Handle of FIG. 10a.

FIG. 16c shows the large biasing loops and anchor-wires of FIG. 16a.

FIG. 19b shows a cross-section of the right ventricle taken from line 19B-19B in FIG. 19a.

FIG. 19d shows a section view of the Distal Lead Segment of FIG. 19c with the Expandable Displacement Member collapsed.

FIG. 19e shows a side view of the Distal Lead Segment of FIG. 19c with the Expandable Displacement Member collapsed.

FIG. 19f shows a section view of the Distal Lead Segment of FIG. 19c with the Expandable Displacement Member expanded.

FIG. 19g shows a side view of the Distal Lead Segment of FIG. 19c with the Expandable Displacement Member expanded.

FIG. 19h shows a section view of the Distal Lead Segment of FIG. 19c with the shaped Expandable Displacement Member expanded, showing how varying the wall thickness of the Expandable Displacement Member in specific locations can result in a desired shape when expanded.

FIG. 23a shows a side view of the Distal Lead Segment of an electrical sensing/stimulation device with a Mechanically Expandable Displacement Member in a collapsed configuration, according to many embodiments.

FIG. 23b shows a side view of the Distal Lead Segment of the electrical sensing/stimulation device of FIG. 23a with the Mechanically Expandable Displacement Member in an expanded configuration.

FIG. 23c shows a section view of the Distal Lead Segment of the electrical sensing/stimulation device of FIG. 23a taken through line 23C-23C in FIG. 23b.

FIG. 24b shows an electrical sensing/stimulation device and an external power generator which may be coupled thereto through a magnetic connection hub, according to many embodiments.

FIG. 24c shows the electrical sensing/stimulation device, the external power generator, and the magnetic connection hub of FIG. 24b coupled together.

FIG. 25b shows a top view of the retractable extension cord adapter of FIG. 25a in an axially retracted configuration.

FIG. 25c shows a top view of the retractable extension cord adapter of FIG. 25a in an axially stretched configuration.

FIG. 25d shows a top view of the retractable extension cord adapter of FIG. 25a.

FIG. 25e shows a side view of the retractable extension cord adapter of FIG. 25a.

FIG. 25f shows an exploded, side view of the retractable extension cord adapter of FIG. 25a.

FIG. 27b shows a magnified view of the Torque Control Member of FIG. 27a.

DETAILED DESCRIPTION

The present disclosure describes herein devices and methods for the delivery and affixation of an electrode, or an electrode array within a body cavity. Such an electrode or electrode array may be commonly referred to as a sensing or pacing lead. Such leads are described herein for use in cardiac applications, i.e., placement of the electrode or electrode array within a chamber of the heart. But the devices and methods described herein are not so limited, and may be applied to any cavity or vessel of the body accessible by way of a catheter system. Vascular access sites for introduction of the lead may be from the internal jugular vein, femoral vein, or subclavian vein as examples, but are not so limited. The electrode, or electrode array may be used for sensing intrinsic electrical activity of body tissues, but the electrode or electrode array may also be used to deliver electrical stimulation to the body tissue when the electrode or electrode array is connected to either an implanted electrical pulse generator (for example, via an adapter that may connect to the proximal pin connectors of the leads such as with industry standard IS-1 type connectors or the like) or an external electrical pulse generator.

Figure 1A:
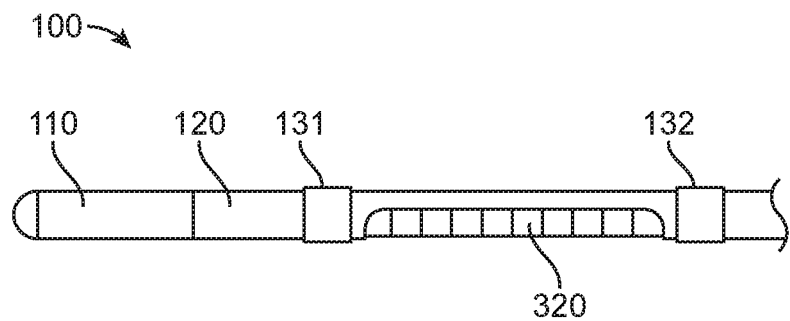
FIG. 1a shows a side view of the Distal Lead Segment of an electrical sensing/stimulation device, with the Tissue Attachment Members retracted and Balloon deflated, according to many embodiments.
Figure 1B:
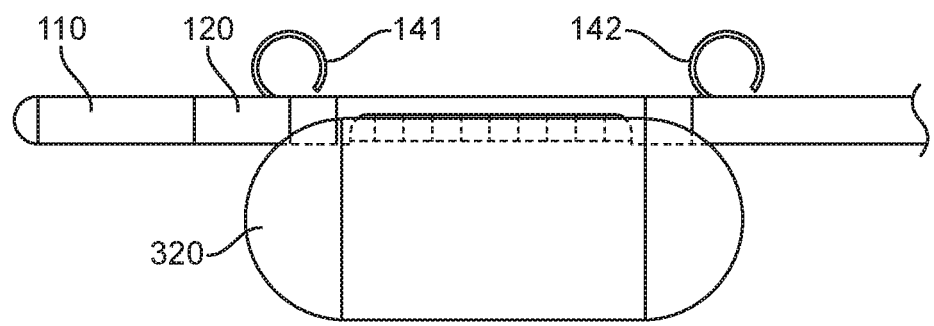
FIG. 1b shows a side view of the Distal Lead Segment of the electrical sensing/stimulation device of FIG. 1a, with the Tissue Attachment Members deployed and Balloon inflated.

FIGS. 1a and 1b show the fundamental elements of the lead distal segment 100, which may include an elongate lead body 120, a displacement mechanism comprising an eccentrically expandable displacement element 320 (that is, the expandable displacement element 320 may expand out laterally from one lateral side of the elongate lead body 120, which may be tubular in shape), sensing/stimulation electrode(s) 131 and 132, tissue attachment member(s) 141 and 142, and an atraumatic tip 110. In some embodiments, the lead body 120 may have a nominal diameter of 0.080", and a working length (as measured along the lead body from the device distal tip to the handle) of 110 cm, but both are not so limited and may be adjusted to suit any specific anatomical configuration. As described herein, each element of the lead may take on various designs and forms, but all operating in a fashion to provide the lead with the same fundamental operational features. In some embodiments, element 142 may exit the elongate body from the same location as 141, or vice a versa. Moreover, in some embodiments, one or more tissue attachment members may exit the elongate body 120 from the same axial location.

Lead Body

Figure 2A:
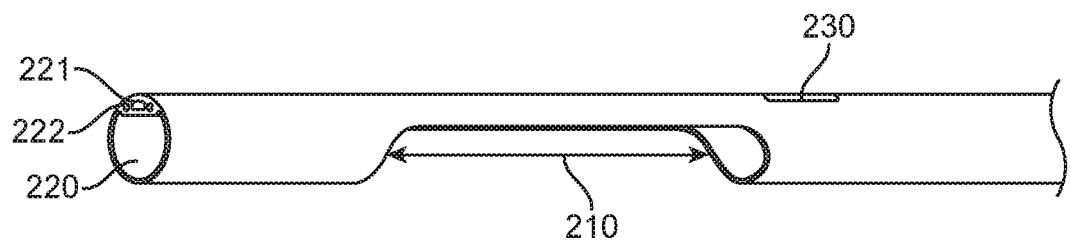
FIG. 2a shows a side view of the Distal Lead Body of the electrical sensing/stimulation device of FIG. 1a—showing longitudinal cut-out through which the Balloon expands when inflated.
Figure 2B:
FIG. 2b shows a top view of the Distal Lead Body of FIG. 2a—showing small cut-outs for passage of the Ring Electrode Wires and the Tissue Attachment Members.
Figure 2C:
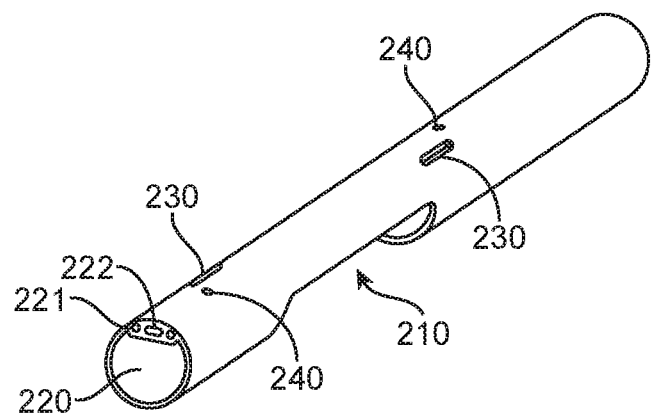
FIG. 2c shows a perspective view of the end of the Distal Lead Body of the FIG. 2a—showing the main central lumen within which is mounted the Balloon; the two small circular lumens, each of which houses a Ring Electrode Conductor Wire; and the small oval lumen, within which translates the Tissue Attachment Members.

The lead body 120 may comprise of an extruded thermoplastic polymer material having one or more lumens. In some embodiments, the material may be Pellethane® having a Shore hardness of 55 D or 63 D, but is not so limited. A thermoset polymer such as silicone may also be used. The polymer may include a radiopaque additive such as barium sulfate or bismuth, such as to provide a fluoroscopic image of the lead body when the device is being imaged during the implantation procedure, using a fluoroscope. FIGS. 2a-2c show the lead body 120 incorporating one or more lumens that are used for communication from the proximal end of the lead body to the distal end of the lead body. In some embodiments, one or more lumens communicate to the displacement member(s) 320, to the electrode(s) 131, 132 and to the tissue attachment member(s) 141, 142. The distal end of the lead body may have a curve which may be manipulable by the user and may terminate with an atraumatic tip 600 or another atraumatic tip, examples of which are shown in FIGS. 8a-8d and 18a-18i.

Torque Control Member

Depending on the durometer and exact cross sectional profile of the lead body, the lead body may or may not have the adequate torque control required to align the distal lead segment 100 to the target tissue during the implantation procedure. To provide increased torque control to the lead body 120, a torque control member 710, 720, 730 may be fabricated into the lead body 120. As depicted in FIGS. 6c, 7a, and 9a-9c, within the length of the main central lumen 220 of the lead body 120 may reside a torque control member 710, 720, 730. The torque control member may comprise a counter-wound coil configuration, wherein a first inner coil 712 which is wound in a first direction is encased by an outer coil 714 that is wound in the opposite direction. These coil configurations can also be referred to as a "bi-plex" type coil assembly. This coil assembly can generally provide somewhat better torque control as the assembly is torqued in a direction that will tighten the outer coil onto the inner coil. Another coil configuration 720, referred to as a "tri-plex" type coil assembly may include a third coil 722, such that the inner and outer coils are wound in the same direction, and the middle coil is wound in the opposite direction. Generally, a tri-plex coil assembly can provide better torque control as the coil is rotated about its axis in either direction. A third type of torque control member 730 is shown in FIG. 9c and may be a braided catheter shaft, a composite structure well known in the medical device industry comprising an inner layer of polymer such as Pellethane or nylon but not so limited, surrounded by a braided tube consisting typically of stainless steel wire, and then encased in an outer layer of polymer such as Pellethane or Nylon. Many suitable polymers may be specified for the inner and outer layers and may also include polyimide, silicones or other thermoplastics or thermoset polymers. The braid wire may be other than stainless steel, for example Nitinol, MP35N or 35NLT (available, for example, from Fort Wayne Metals, Fort Wayne, Ind.) or other appropriate metals or polymers such as Kevlar, but not so limited. The diameter of the braid wire may vary between 0.001" and 0.010", but is not so limited.

The bi-plex coil assembly 710, tri-plex coil assembly 720 or braided catheter shaft 730 may be inserted within and affixed within the main central lumen 220 by thermally melting the lead body material 120 into the torque control member 710, 720 or 730, by adhesives, or co-extruding the lead body with the braid, but the attachment scheme is not so limited. The attachment to the main central lumen 220 may be in a variety of locations, such as along the entire length of the lead body 120, at periodic intervals within the lead body, or at specific predetermined points along the lead body 120. Affixing the torque control member 710, 720 or 730 to the main central lumen 220 of the lead body 120 can unify them to move as one assembly. The proximal end of the lead body 120 and the proximal end of the torque member 710, 720 or 730 both terminate together and can be attached to the distal segment of the handle. Thus, as the handle is rotated the torque member 710, 720 or 730 and the lead body 120 can move in unison. Further torque members and torque control members are described below and herein.

Displacement Member

The main central lumen 220 of the lead body 120 may terminate distally at the displacement member 320. The main central lumen 220 of the lead body 120 may travel within the length of the lead body and terminates proximally at an inflation port 802 to allow connection of a device to pressurize air or other inflation medium within the lumen 220 and the inflatable displacement member 320.

As shown in FIGS. 1b, 3a-3c, and 4a-4d, the displacement member may comprise an expandable member 320 that may be mounted substantially within the main central lumen 220 of the lead body 120. This expandable displacement member 320 may generally comprise a tubular structure (tube) and may be constructed of an elastomeric polymer, a thin-walled non-compliant or semi-compliant polymer. The expandable displacement member 320 may be inflated to expand the displacement member 320 in many embodiments. When inflated with air, $CO_2$, liquid (e.g. water, iodinated contrast/water solution, or other appropriate biocompatible fluid), or other inflation medium, the inflatable displacement member 320 will expand and deploy through the deployment window 210 that is cut into the central main lumen 220 of the lead body 120. Being that the expandable displacement member 320 can deploy through a deployment window 210 on one side of the lead body, the expansion of the expandable displacement member 320 may be eccentric to the lead body 120 itself. The position of the deployment window 210 can be substantially opposite (for example, diametrically opposing or on opposite lateral sides) to that of the tissue attachment member deployment ports 240, but the deployment window 210 may be positioned at any angular position as well as any axial and/or longitudinal position relative to the tissue attachment member deployment ports 240. In some embodiments, two or more tissue attachment members 141, 142 may be deployed from one tissue attachment member deployment port 240. In some embodiments, the displacement member 320 may comprise expandable metal or polymeric scaffoldings, i.e., tubular meshes as an example that when foreshortened along their axis may radially expand. Other examples of expandable members are shown in U.S. patent application Ser. No. 13/219,874 to Garai, et al, the contents of which are fully incorporated herein by reference.

In some embodiments, the expandable displacement member 320 may be an elastomeric polymer material. Other suitable materials may be used that can afford the degree of expansion as required by the size and shape of the anatomical structure within which the lead will be positioned and affixed to the tissue. When inflated, the expandable displacement member 320 can expand and deploy through the deployment window 210, and when deflated the expandable displacement member 320 can contract and resume its mounted position within the main central lumen 220 of the lead body 120. When properly positioned in a body cavity, expansion of the expandable displacement member 320 can initiate contact and exert force on a wall of a body cavity, thus displacing the lead body 120, associated electrode(s) 131, 132, and tissue attachment deployment ports 240 in a different (e.g., the opposite) direction, towards the tissue targeted for contact with the electrode(s) 131, 132, and to orient the tissue attachment deployment ports 240 to also be opposed to the target tissue for deployment of the tissue attachment member(s) 141, 142 into the target tissue for affixation to the tissue. The expandable displacement member 210 may also be constructed of a non-compliant or semi-compliant polymer or other material suitable for inflation. In this configuration, the expandable displacement member 320 may be folded in a fashion to allow its placement substantially within the lead body, and upon deflation the inflatable displacement member may re-fold and retract back to its original un-deployed configuration.

Figure 3A:
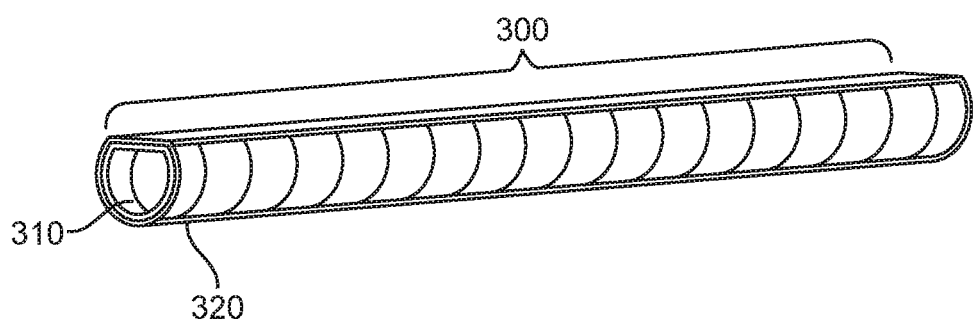
FIGS. 3a-3c show the Balloon of the electrical sensing/stimulation device of FIG. 1a mounted on a D-shaped longitudinal Element to produce an Inflatable Element Cartridge, according to many embodiments. This sub-assembly may be inserted into the main D-shaped lumen of the Distal Lead Body.
Figure 3B:
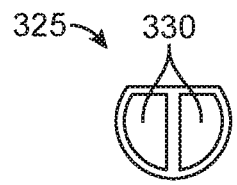
Figure 3B:
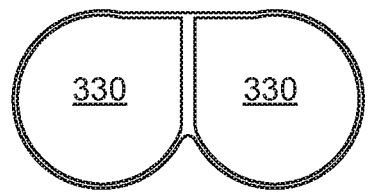
Figure 3B:
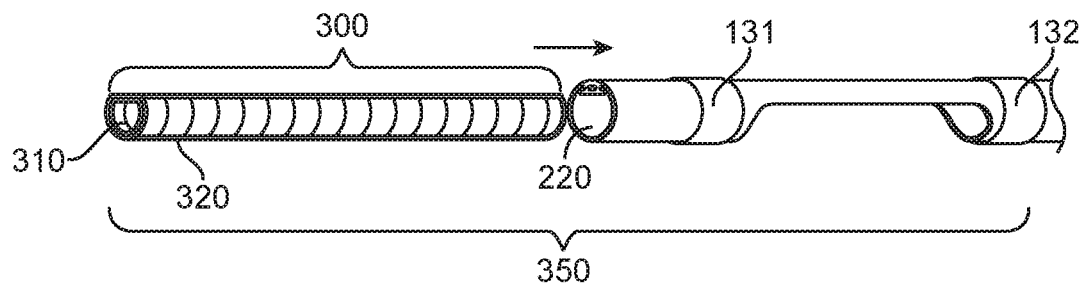
Figure 3C:
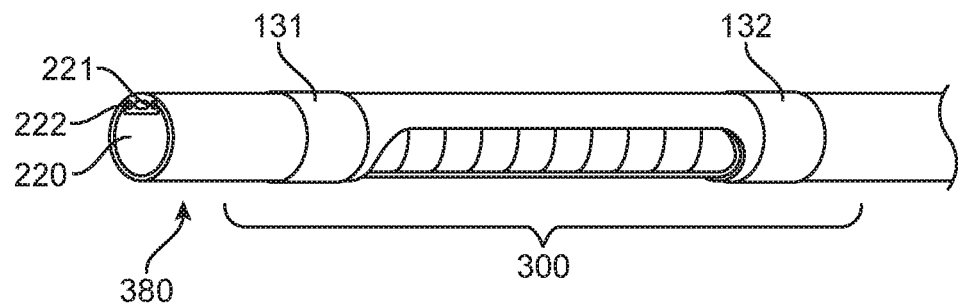

As shown in FIGS. 3a-3c, the expandable displacement member 320 can be mounted over a hollow D-shaped longitudinal element 310, which may be a coil, polymer extrusion or injection molded component, as examples. As shown in FIG. 3a, when mounted in this fashion, the D-shaped longitudinal element and the expandable displacement element 320 form a cartridge 300. In this configuration, the circumference of the outer diameter of the expandable displacement member 320 will be less than the circumference of the inner diameter of the lumen 220 within which the expandable displacement member 320 resides. The expandable member cartridge 300 can be inserted into the distal end of the central main lumen 220, positioned central to the deployment window 210, and affixed in place at the proximal and distal ends within the central main lumen 220 using adhesives or thermal bonding. The proximal end of the cartridge may be open and can be in communication with the main central lumen 220 of the lead body 120, and is thus inflated as described earlier.

Figure 4A:
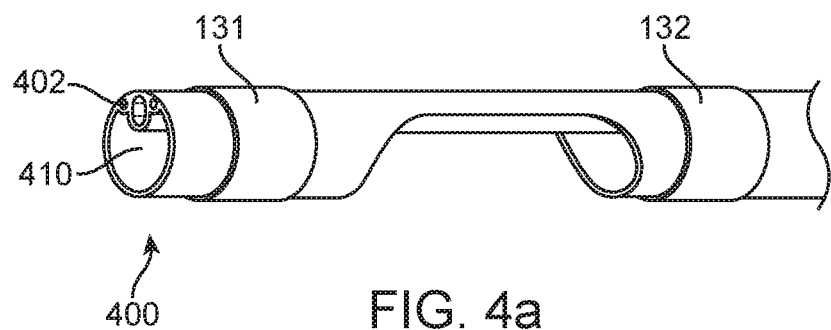
FIGS. 4a-4d show another Inflatable Displacement Member mounted within the Distal Lead Body of an electrical sensing/stimulation device, according to many embodiments.
Figure 4B:
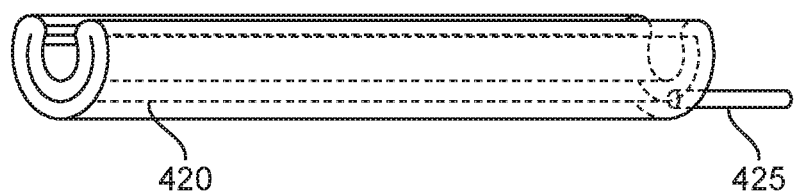
Figure 4C:
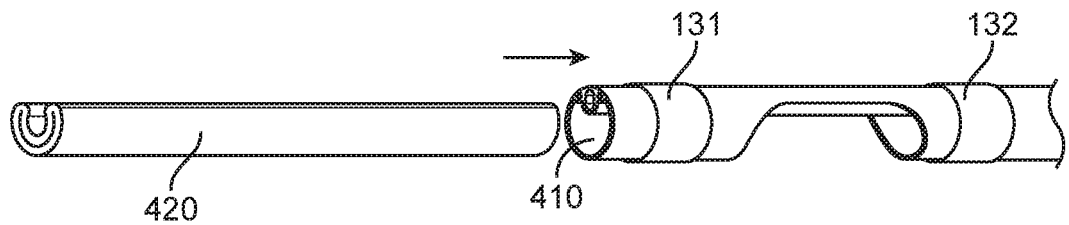
Figure 4D:
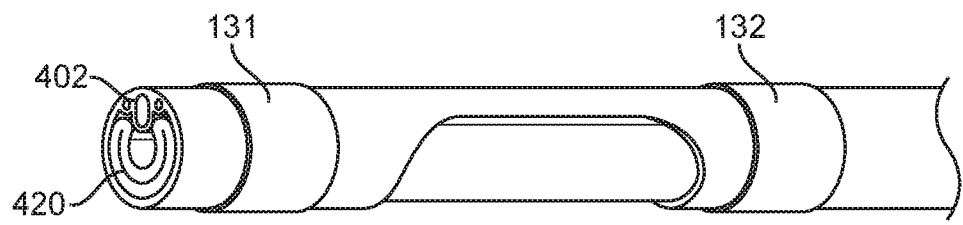

As shown in FIGS. 4a-4c, the expandable displacement member 420 may also comprise a tubular structure (tube) and may be fabricated using similar materials as those in described above with reference to FIG. 3a. However, in the embodiments shown in FIGS. 4a-4c, the expandable displacement member 420 may be folded onto itself and configured in a "C-shaped" nested configuration. An advantage of this configuration is that for a given lumen 410 within which the expandable displacement member 320 resides, the circumference of the tube which is folded to produce the nested configuration can be greater than the inner circumference of the lumen 410. Given the same materials and wall thickness of the tube to make the expandable displacement members 320 and 420, upon expansion the expandable displacement member 420 of FIG. 4 can be capable of expanding more than the expandable displacement member 320 as shown in FIG. 3, due to the fact that the effective circumference of the expandable displacement member 420 is greater than that of the expandable displacement member 320.

The configuration of mounting the expandable displacement member 320 or 420 within a lumen 220 of the lead body 120 can allow the expandable member 320, 420 to deploy through the deployment window 210. The longitudinal and circumferential dimensions of the deployment window 210 may be adjusted as deemed appropriate to control the deployed dimensions of the displacement member, for example by controlling the volume of air or fluid within the expandable displacement member, consistent with the anatomical requirements within which the lead may be designed to operate. Lengthening the deployment window 210 can thus increase the length of the deployed displacement member 320, 420, while increasing or decreasing the circumferential dimension of the deployment window can increase or decrease the amount of expansion, and thus the diameter, of the expandable displacement member 320, 420. Inflation of the C-shaped folded expandable displacement member 420 can be accomplished via a small communication tube 425, the distal end of which lies within the lumen of the expandable displacement member 420 and the proximal end of which is in communication with the main central lumen 220 of the lead body 120. Both ends of the C-shaped balloon may be sealed to provide a hermetically inflatable balloon cartridge. Additionally, the communication tube 425 may be sealed to the distal end of at least one embodiment of the torque member 730 such that the torque member 730 can also serve the purpose of the inflation lumen for the balloon cartridge. In this instance, the torque member 730 may be a polymer laminated shaft of braided stainless steel wire, coil, or similar structure and would have a continuous wall structure capable of holding pressure.

FIGS. 20a to 20e show section views of the distal lead segment 100 or distal lead segment 100a (discussed further below and herein). As shown in FIGS. 20a to 20e, the expandable displacement element 320 may be folded in different ways within the body of the distal lead segment 100 or 100a.

Figure 20A:
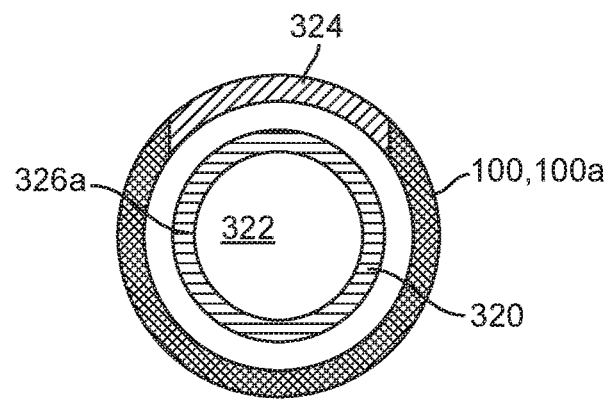
FIG. 20a shows a section view of the Distal Lead Segment of an electrical sensing/stimulation device with the Expandable Displacement Member collapsed into a circle shape within the Lead Body, according to many embodiments.

As shown in FIG. 20a, the expandable displacement element 320 may be circular or elliptical when collapsed within the distal lead segment 100 or 100a. The expandable displacement element 320 may have a circumference 326a which is smaller than that of the distal lead segment 100 or 100a, which may limit the size of the expandable displacement element 320 when expanded at least partially out of the exit port 324 of the distal lead segment 100 or 100a.

FIGS. 20b to 20e show examples of other ways to nest the expandable displacement element 320 within the distal lead segment 100 or 100a, such to increase the circumference of the expandable displacement element 320 such that the expandable displacement element 320 can have a greater size when expanded at least partially out of the exit port 324 of the distal lead segment 100 or 100a.

Figure 20B:
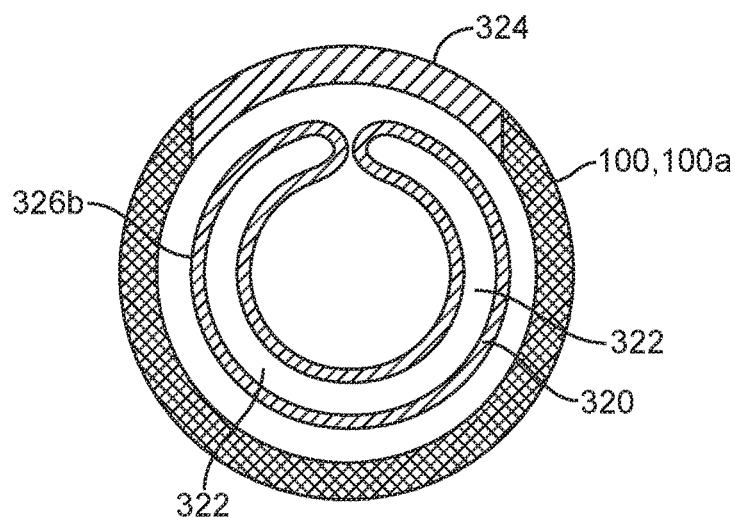
FIG. 20b shows a section view of the Distal Lead Segment of an electrical sensing/stimulation device with the Expandable Displacement Member collapsed into a C-shape within the Lead Body, according to many embodiments.
Figure 20C:
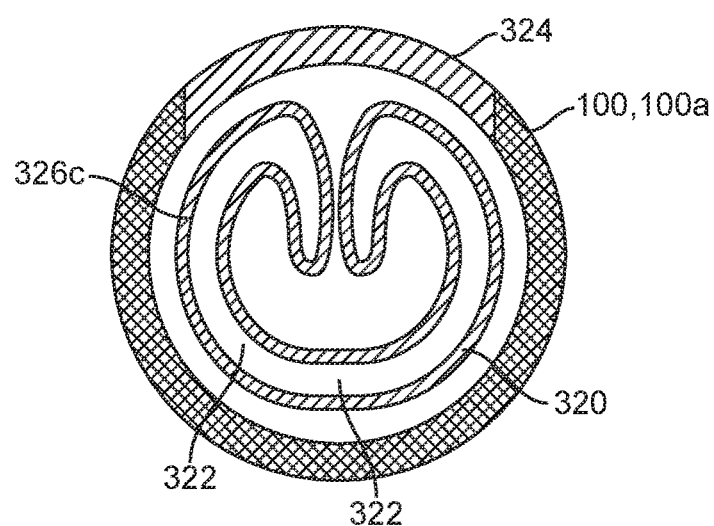
FIG. 20c shows a section view of the Distal Lead Segment of an electrical sensing/stimulation device with the Expandable Displacement Member collapsed into an involuted C-shape, where the ends of the "C" involute within the "C", and with the balloon nested within the Lead Body, according to many embodiments.
Figure 20D:
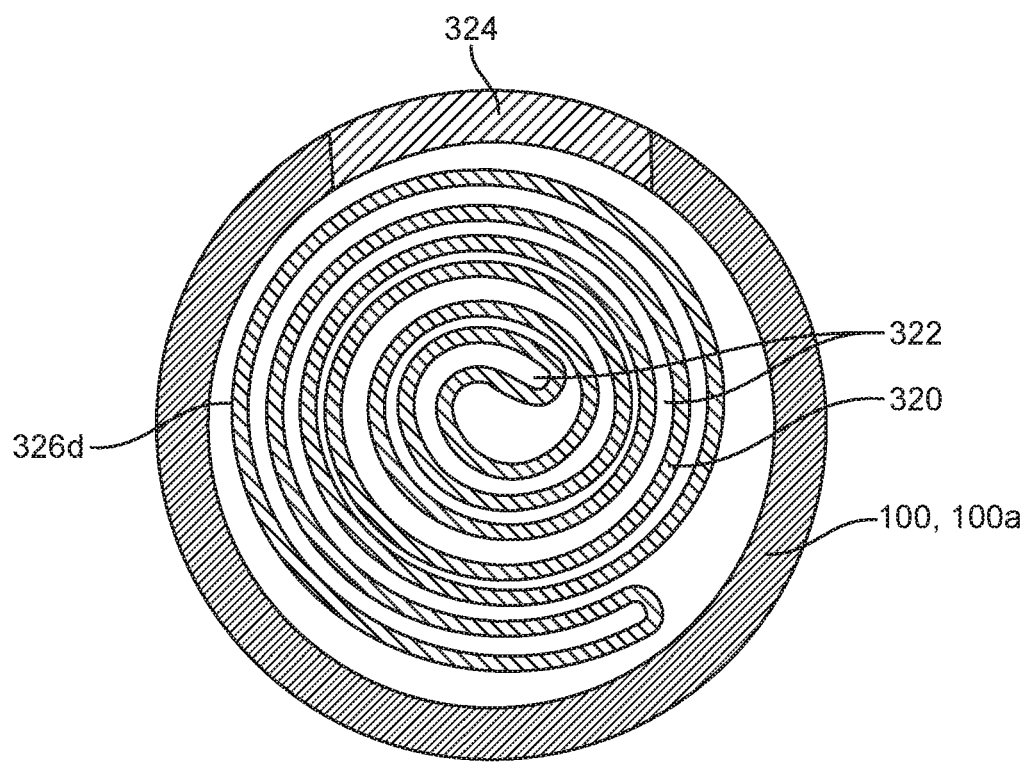
FIG. 20d shows a section view of the Distal Lead Segment of an electrical sensing/stimulation device with the Expandable Displacement Member collapsed into a spiral shape within the Lead Body, according to many embodiments.
Figure 20E:
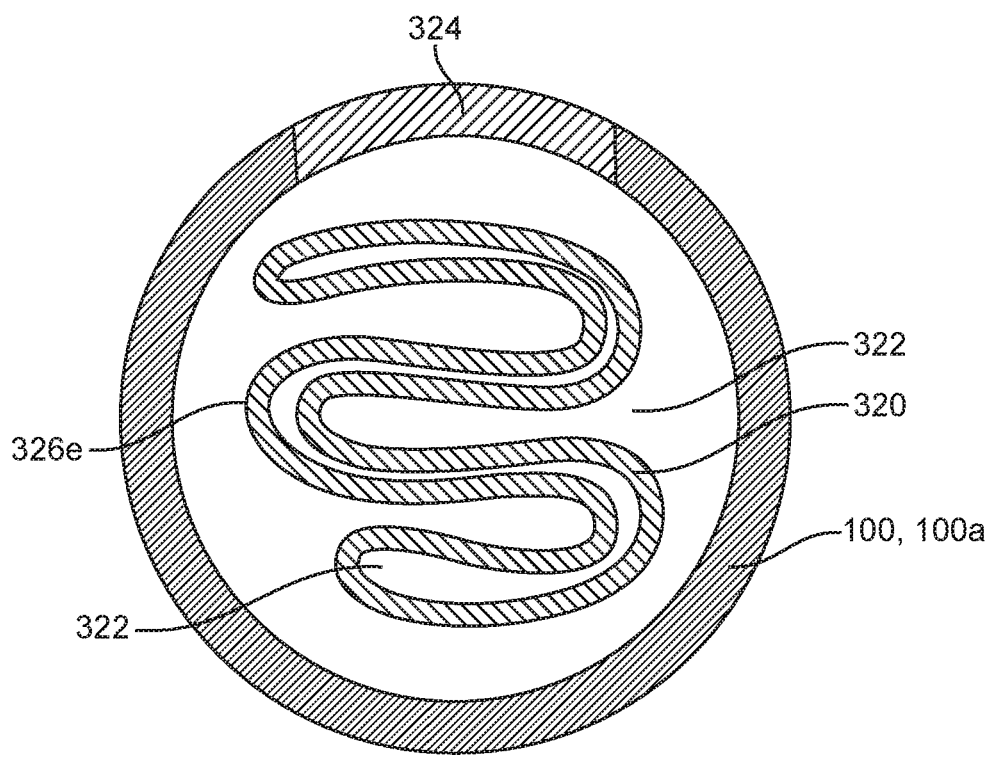
FIG. 20e shows a section view of the Distal Lead Segment of an electrical sensing/stimulation device with the Expandable Displacement Member collapsed into a serpentine shape within the Lead Body, according to many embodiments.

As shown in FIG. 20b, the expandable displacement element 320 may be folded into a C-shape when collapsed within the distal lead segment 100 or 100a and may have a circumference 326b which may be greater than the circumference 326a and/or the circumference of the distal lead segment 100 or 100a. As shown in FIG. 20c, the expandable displacement element 320 may be folded into an involuted C-shape (that is, the ends of the "C" involute) when collapsed within the distal lead segment 100 or 100a and may have a circumference 326c which may be greater than the circumference 326a and/or the circumference of the distal lead segment 100 or 100a. As shown in FIG. 20d, the expandable displacement element 320 may be folded into a spiral shape when collapsed within the distal lead segment 100 or 100a and may have a circumference 326d which may be greater than the circumference 326a and/or the circumference of the distal lead segment 100 or 100a. As shown in FIG. 20e, the expandable displacement element 320 may be folded into a serpentine shape when collapsed within the distal lead segment 100 or 100a and may have a circumference 326e which may be greater than the circumference 326a and/or the circumference of the distal lead segment 100 or 100a. In the embodiments shown by FIGS. 20a to 20e, the inflation medium 322 may be provided inside the expandable displacement element 320 within the distal lead segment 100 or 100a while ambient fluid such as blood may reside outside of the expandable displacement element 320.

Figure 21A:
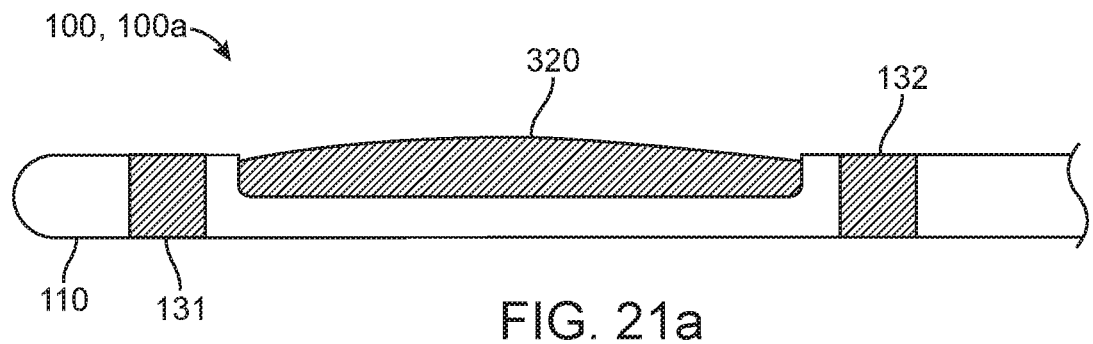
FIG. 21a shows a side view of the Distal Lead Segment of an electrical sensing/stimulation device with the Expandable Displacement Member collapsed in the axial direction within the Lead Body, according to many embodiments.
Figure 21B:
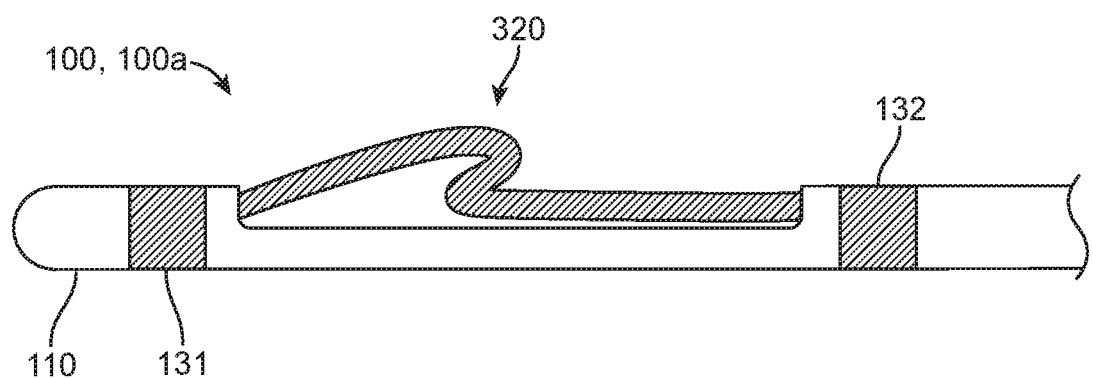
FIGS. 21b and 21c show side views of the Expandable Displacement Member of FIG. 21a partially expanded outward and showing its axial fold.
Figure 21C:
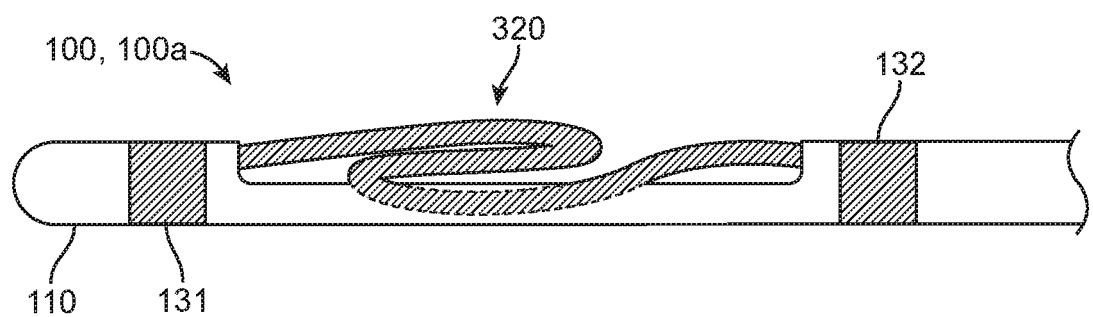

FIGS. 20b to 20e show that the expandable displacement element 320 may be folded about the axial or longitudinal axis of the distal lead segment 100 or 100a. Alternatively or in combination, the expandable displacement element 320 may be folded in a direction transverse to the axial or longitudinal axis of the distal lead segment 100 or 100a as shown in FIGS. 21a to 21c. FIG. 21a shows the expandable displacement element 320 fully collapsed within the distal lead segment 100 or 100a. FIGS. 21b and 21c show the expandable displacement element 320 partially expanded and exposing the folded portion of the expandable displacement element 320.

Figure 5A:
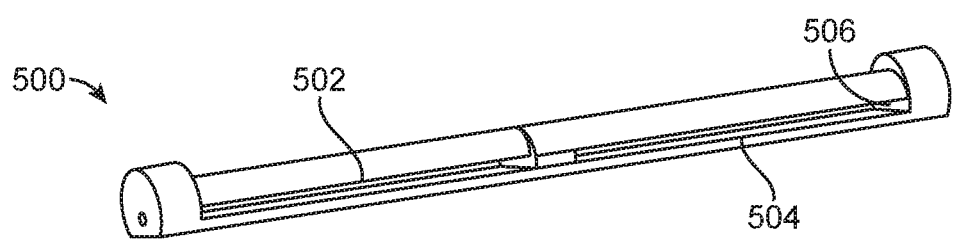
FIGS. 5a-5e depict another Inflatable Displacement Member, which may be mounted on a Cartridge in a helical fashion and mounted within the Distal Lead Body of an electrical sensing/stimulation device, according to many embodiments.
Figure 5B:
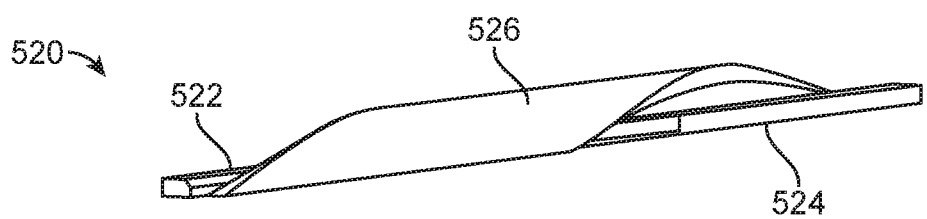
Figure 5C:
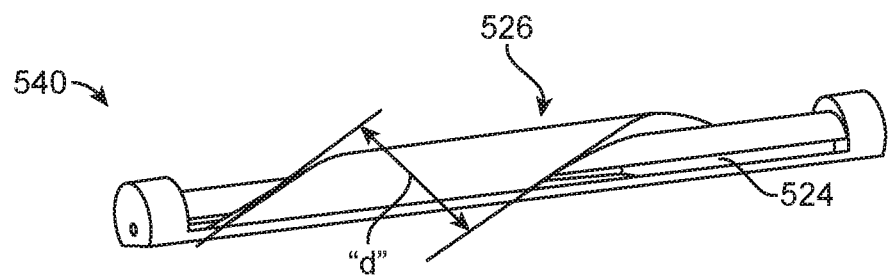
Figure 5D:
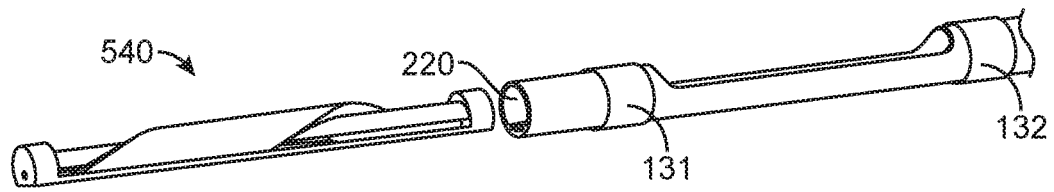
Figure 5E:
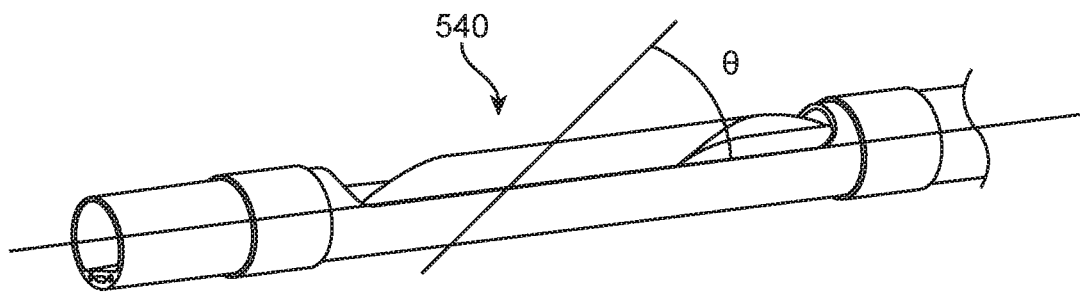

As shown in FIGS. 5a-5e, the expandable displacement member 526 may comprise a generally tubular structure fabricated of similar materials mentioned for the embodiments in FIGS. 3 and 4. FIG. 5 may demonstrate that the tubular expandable displacement member 526 may be mounted in a spiral, or helical fashion on a cartridge 500. The cartridge 500 may have distal and proximal receiving channels 502, 504 for receiving and mounting of the distal and proximal ends of the expandable displacement member 526. Mounting can be performed by use of adhesives, or thermal boding, but is not so limited. The expandable displacement member 526 may be inflated via a small port 506 at the proximal end of the mounting cartridge 500 that communicates between the lead lumen 220 to the interior of the expandable displacement member 526. The length of the expandable displacement member 526 held between the distal and proximal bonding areas 502 and 504 can thus comprise the expandable portion of the member that extends through the deployment window 210 of the lead body 120. An advantage provided by such an expandable displacement member 526 is that for a given size lead body 120 and deployment window 210, the diameter of the expandable displacement member 526 tube can be increased beyond those of FIGS. 3 and 4. FIG. 5e shows that the longitudinal axis of the expandable displacement member 526 tube is at an angle θ to that of the lead body axis. FIG. 5c shows the width "d" of the expandable displacement member 526 tube, when flattened and mounted on the cartridge 500. By adjusting the angle θ and the length of the deployment window 210, the width of the flattened expandable displacement member 526 tube, and accordingly the tube's diameter, can be increased to afford even greater expansion of the expandable displacement member 526.

The aforementioned displacement members 320, 420, and 520 can generally be considered as a single lumen tube. However, it can be appreciated that any of these displacement members may be sub-divided such that as seen in cross-section, there may be multiple parallel lumens. One such example is shown in cross section in FIG. 3a' wherein two or more lumens 330 may be coincident along the length of the displacement member. FIG. 3a' shows the cross section of the displacement member 325 in the un-inflated state, and FIG. 3a" shows the displacement member in the inflated state. In this configuration, the displacement member may or may not be mounted on a cartridge. The inflation member may simply be inserted into the lead body extrusion 220 and affixed in place with this lumen using methods previously described. Under inflation, each lumen may inflate and a specific cross-sectional geometric configuration may be produced as shown in FIG. 3". Thus, a shape that closely matches the anatomical cavity within which the displacement member is inflated may be produced, such that the inflated displacement member may self-align to the anatomical space.

The expandable displacement member 320, 420, or 520 may also incorporate fluoroscopic indicators printed on its surface, as expandable markers, or as local markers. In the case of an expandable marker, as the expandable displacement member 320, 420, or 520 expands, the printed fluoroscopic markers can elongate with the expansion of the displacement member 320, 420, or 520, forming an elongate marker. Alternatively or in combination, the marker may be printed as a serpentine shape, and may transform into a more linear shape as the expandable displacement member 320, 420, or 520 expands. In other embodiments, the fluoroscopic indicators may simply be small local points, such that as the expandable displacement member 320, 420, or 520 expands the local printed points move with the displacement member 320, 420, or 520. Having local points printed on one side of the displacement member 320, 420, or 520, for example, may give a fluoroscopic indicator as to the alignment of the distal lead segment 120 within the body cavity. Pad printing of tungsten markers or other radiopaque materials may be used in fabricating these types of markers.

As shown in FIGS. 22a to 22j, the expandable displacement member 320 may comprise a metallic film or radiopaque marker 328 to help guide the distal lead segment 100 or 100a. The marker 328 may have a shape such that it can expand as the expandable displacement member 320 expands and collapses as the expandable displacement member 320 collapses. For example, the marker 328 may have a serpentine pattern. The marker 328 may comprise fillets on one or more of its corners to allow the serpentine patterned marker 328 to expand and collapse with minimal internal stress or strain such that it does not break or tear as the marker 328 cycles between expansion and collapse.

Figure 22A:
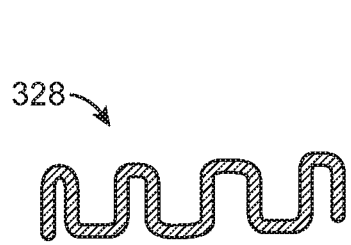
FIG. 22a shows a side view of a serpentine marker for the Expandable Displacement Member of the Distal Lead Segment of an electrical sensing/stimulation device in a collapsed configuration, according to many embodiments.
Figure 22B:
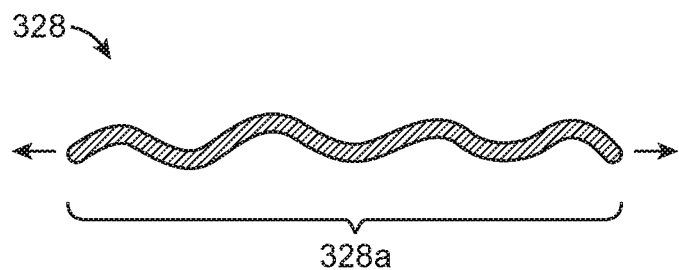
FIG. 22b shows a side view of the serpentine marker of FIG. 22a in an expanded configuration.

FIG. 22a shows an exemplary marker 328 having a serpentine pattern and in the collapsed configuration. When an axially or radially expansive force 328a is applied, the marker 328 can axially and/or radially expand as shown in FIG. 22b.

Figure 22C:
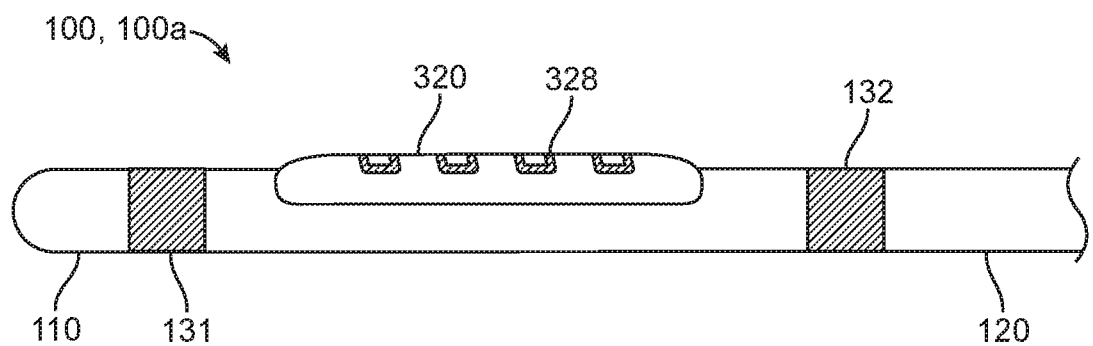
FIG. 22c shows a side view of the serpentine marker of FIG. 22a mounted on the Expandable Displacement Member, both in their collapsed configuration.
Figure 22D:
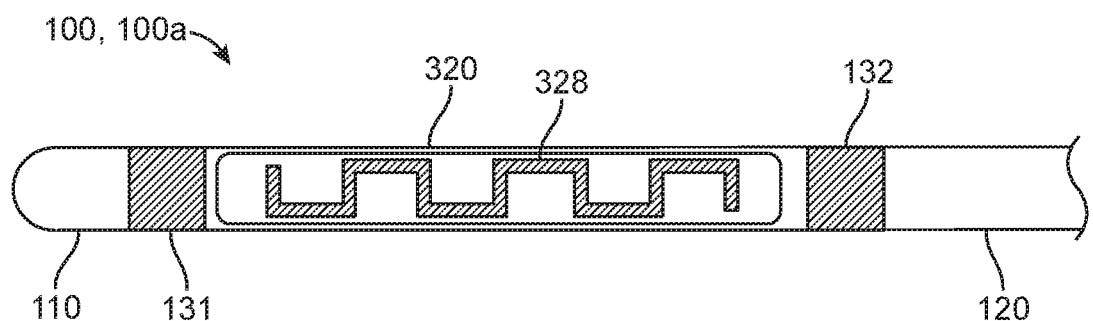
FIG. 22d shows a top view of the serpentine marker of FIG. 22a mounted on the Expandable Displacement Member, both in their collapsed configuration.
Figure 22E:
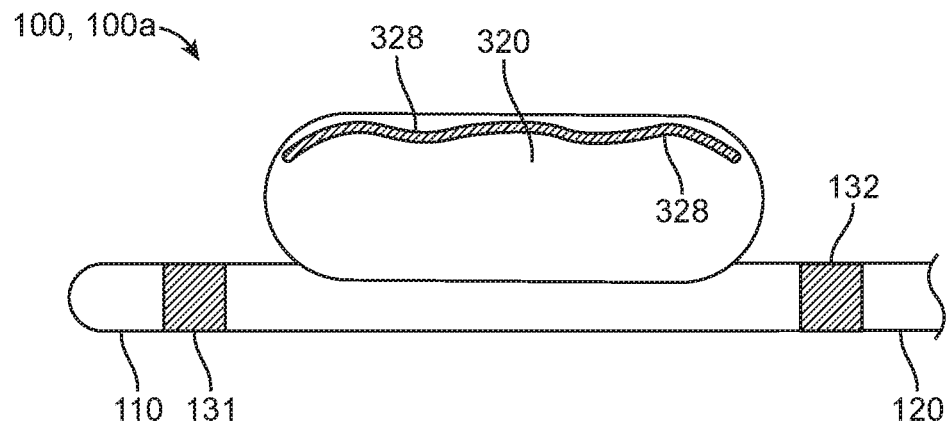
FIG. 22e shows a side view of the serpentine marker of FIG. 22a mounted on the Expandable Displacement Member, both in their expanded configuration.
Figure 22F:
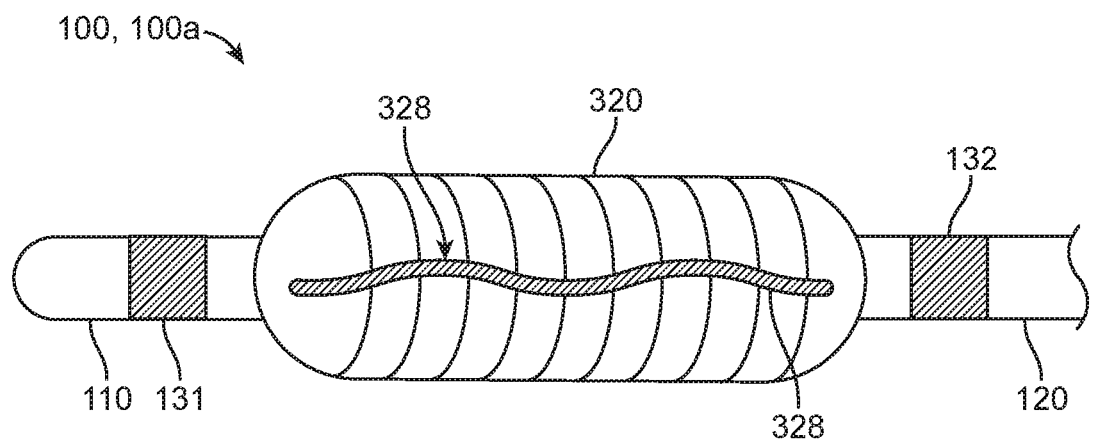
FIG. 22f shows a top view of the serpentine marker of FIG. 22a mounted on the Expandable Displacement Member, both in their expanded configuration.

FIGS. 22c and 22d show the marker 328 placed over the outer surface of the expandable displacement member 320. The expandable displacement member 320 is shown to be in the collapsed configuration with the marker 328 collapsed. FIGS. 22e and 22f show the expandable displacement member 320 in the expanded configuration with the marker 328 expanded.

Figure 22G:
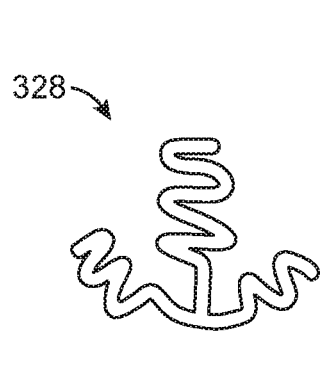
FIG. 22g shows a side view of an arrow-shaped serpentine marker for the Expandable Displacement Member of the Distal Lead Segment of an electrical sensing/stimulation device in a collapsed configuration, according to many embodiments.
Figure 22H:
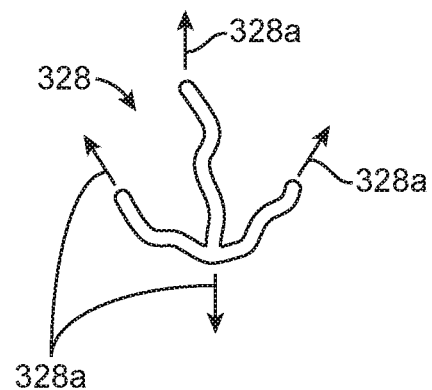
FIG. 22h shows a side view of the arrow-shaped serpentine marker of FIG. 22g in an expanded configuration.
Figure 22I:
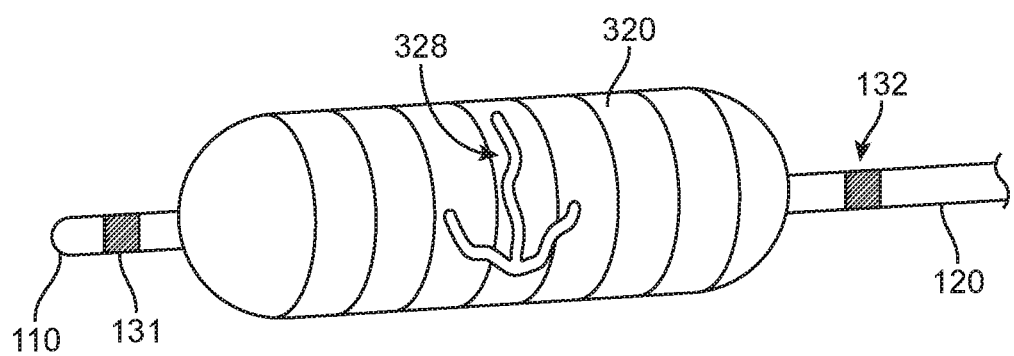
FIG. 22i shows a top view of the arrow-shaped serpentine marker of FIG. 22g mounted on the Expandable Displacement Member, both in their expanded configuration.
Figure 22J:
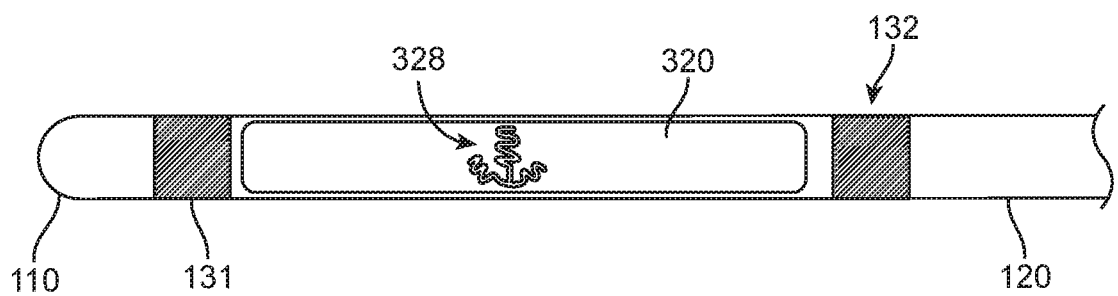
FIG. 22j shows a top view of the arrow-shaped serpentine marker of FIG. 22g mounted on the Expandable Displacement Member, both in their collapsed configuration

In some embodiments, the marker 328 may have a serpentine pattern such that when expanded, the marker 328 can form a specific shape, such as an arrow, to help the user better orient the distal lead segment 100 or 100a under fluoroscopic guidance. FIG. 22g shows an exemplary, arrow-shaped marker 328 in a collapsed configuration and FIG. 22h shows the arrow-shaped marker 328 in the expanded configuration under expansive forces 328a. FIG. 22i shows the arrow-shaped marker 328 mounted on the expandable displacement member 320 which is expanded, thereby expanding the arrow-shaped marker 328. FIG. 22j shows the arrow-shaped marker 328 mounted on the expandable displacement member 320 which is collapsed, thereby collapsing the arrow-shaped marker 328.

The expandable displacement element 320, 420, and 520 may be configured in further various ways for various uses and advantages. As shown in FIGS. 19a to 19h, the expandable displacement element 320 may be shaped to conform to the shape of a target body cavity when expanded. For example, the expandable displacement element 320 when expanded may have a shape conforming to that of the right ventricle RV. The expandable displacement elements 420 and 520 may also be configured to have a shape when expanded to conform to the shape of the target body cavity.

Figure 19A:
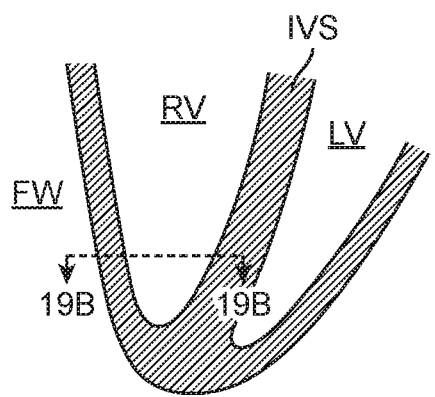
FIG. 19a shows a cross-section of the apex of a patient's heart.
Figure 19B:
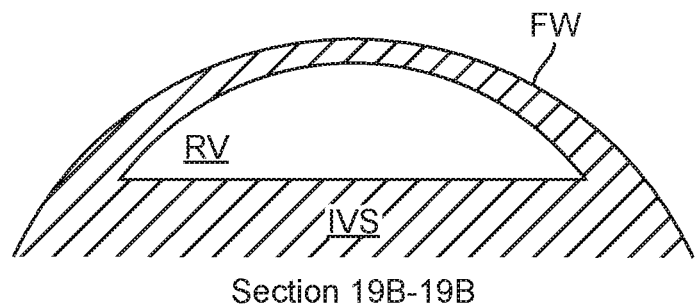

FIGS. 19a and 19b show the anatomy of the apex of the heart, including the right ventricle RV, left ventricle LV, the interventricular septum IVS separating the right ventricle RV with the left ventricle LV, and the free wall FW of the right ventricle RV. FIG. 19b shows a cross-section of the heart taken through line 19B.

Figure 19C:
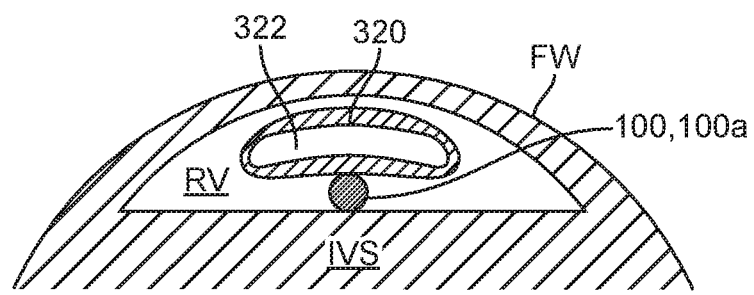
FIG. 19c shows a section view of a Distal Lead Segment of an electrical sensing/stimulation device with a shaped Expandable Displacement Member expanded and conforming to the shape of the cavity of the right ventricle, according to many embodiments.

FIG. 19c shows the sensing/stimulation device distal lead segment 100 or 100a introduced into the right ventricle RV. The expandable displacement element 320 may be expanded with an inflation medium 322 and may have an ovoid or elliptical cross-sectional shape when expanded to match the cross-sectional shape of the cavity of the right ventricle RV. The inflation medium 322 may comprise one or more of saline, water, buffer, air, gaseous $CO_2$, to name a few.

FIGS. 19d and 19e show the device distal lead segment 100 or 100a with the expandable displacement element 320 collapsed. FIGS. 19f and 19g show the device distal lead segment 100 or 100a with the expandable displacement element 320 expanded. FIG. 19e shows a side-view of the device distal lead segment 100 or 100a and FIG. 19d shows a section view of the distal lead segment 100 or 100a taken through line 19D-19D. FIG. 19g shows a side-view of the device distal lead segment 100 or 100a and FIG. 19f shows a section view of the distal lead segment 100 or 100a taken through line 19F-19F.

FIG. 19f shows the sensing/stimulation device distal lead segment 100 or 100a with the expandable displacement element 320 expanded. To achieve the desired shape upon expansion, the expandable displacement element 320 may comprise greater thickness wall areas 320a and lesser thickness wall areas 320b. The greater thickness wall areas 320a may be diametrically opposed (180 degrees) from one another. The lesser thickness wall areas 320b may be diametrically opposed (180 degrees) from one another. The lesser thickness wall areas 320a may have a propensity to expand under lower pressures than the greater thickness wall areas 320a. Accordingly, the expandable displacement element 320 may expand to an ovoid or elliptical shape in cross-section when expanded or inflated. When expanded or inflated, the expandable displacement element 320 having such a shape can provide a backing force to the stabilizers (e.g., stabilizers or deployment members 141/141a, 142/142a, 141b, 142b, 141d, 142d) and can also self-align the distal lead segment 100 or 100a into the right ventricular pocket. The expandable displacement element 320 may be made from an extrusion to have such greater thickness wall areas 320a and lesser thickness wall areas 320b.

As discussed above and herein, the expandable displacement member 320 may be an inflatable element which may be inflated with an inflation medium. Alternatively or in combination, the distal lead segment 100 or 100a may comprise a mechanical expander 320a which may comprise a malecot, an expandable cage, or an expandable scaffold biased to be in an expanded configuration. For example, the mechanical expander 320a may comprise a slotted tube made of a shape memory material such as Nitinol, and the mechanical expander 320a may have an inner lumen through which a shaft can be advanced to push the distal segment 100 out relative to the lead body 120 to contract the mechanical expander 320a. FIG. 23a shows, for example, a force 2301 exerted to place the mechanical expander 320a in the collapsed configuration. FIG. 23b shows, for example, the mechanical expander 320a in the expanded configuration with anchors 2303 expanded radially outward to deploy anchors 2305 through anchor ports 2307 and radially extend electrodes 2309. The mechanical expander 320a may comprise a plurality of conductive tubes 2313 with electrically insulated surface portions 2311 and surface portions which are not electrically insulated and comprise the electrodes 2309. FIG. 23c shows a cross-section of the distal lead segment 100 or 100a with the mechanical expander 320a taken from line 23C-23C in FIG. 23b. As shown in FIG. 23c, the tubes 2313 may extend through the lead body 120 and may have inner lumens through which the anchor wires 2305 may pass through.

Tissue Attachment Members

Figure 6A:
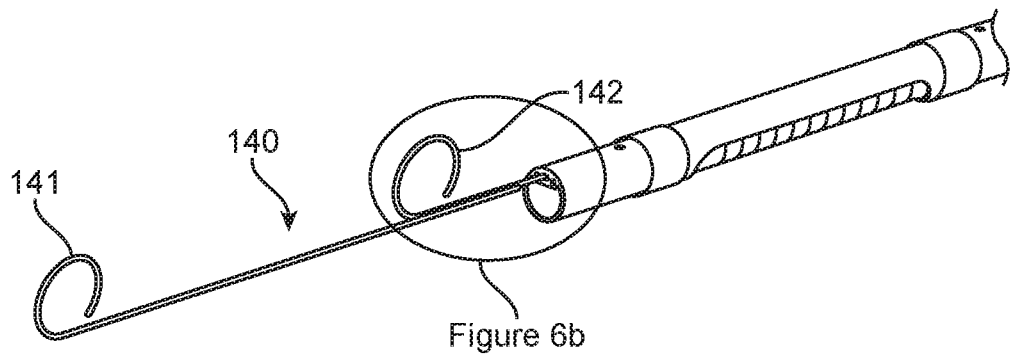
FIG. 6a shows a perspective view of the insertion/keying of the Tissue Attachment Members into the oval channel of the Distal Lead Body of an electrical sensing/stimulation device, according to many embodiments.
Figure 6A:
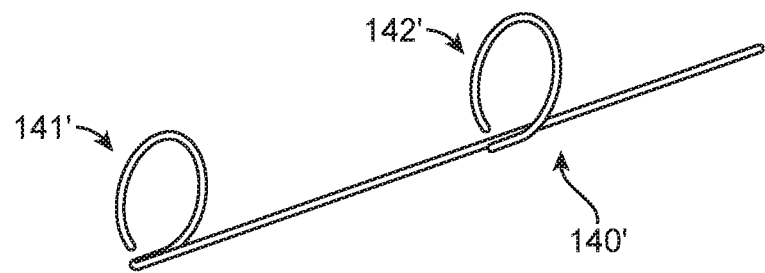
Figure 6B:
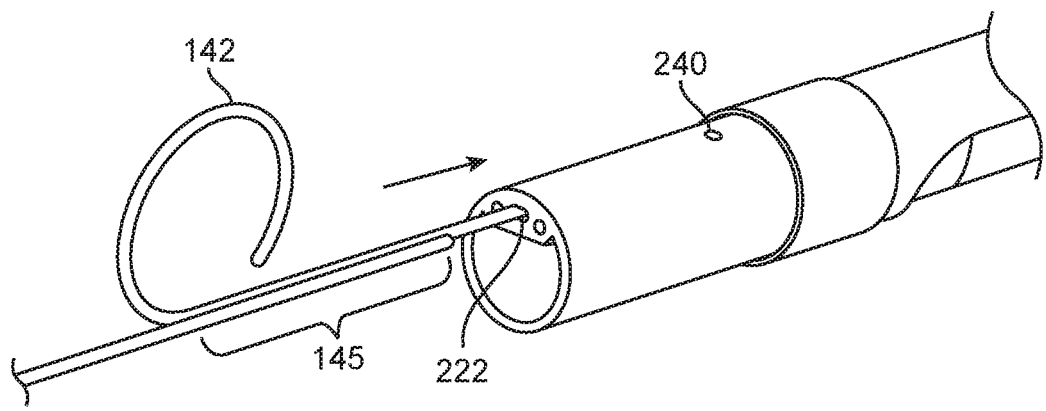
FIG. 6b shows a magnified perspective view of the insertion/keying of the Tissue Attachment Members into the oval channel of the Distal Lead Body.
Figure 6C:
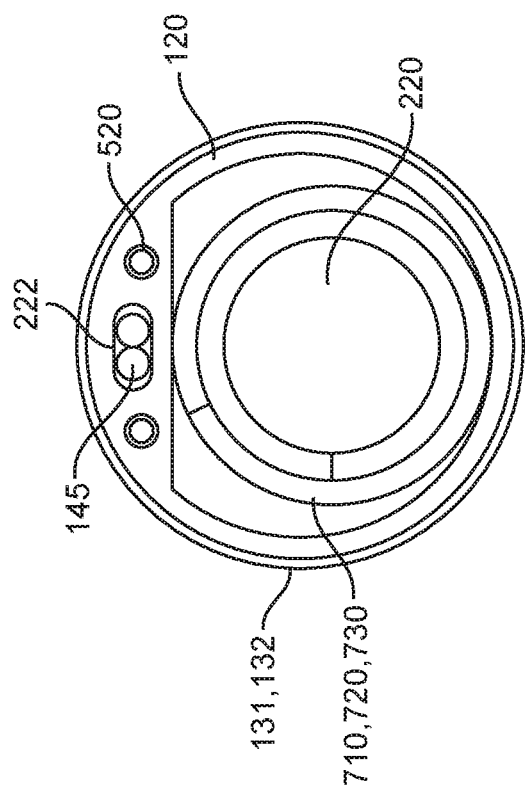
FIG. 6c shows a section view of the positioning of the Tissue Attachment Members into the oval channel of the Distal Lead Body, the mounting position of the Electrodes and associated Electrode Wires, and the position of the internal Torque Control Member.
Figure 7A:
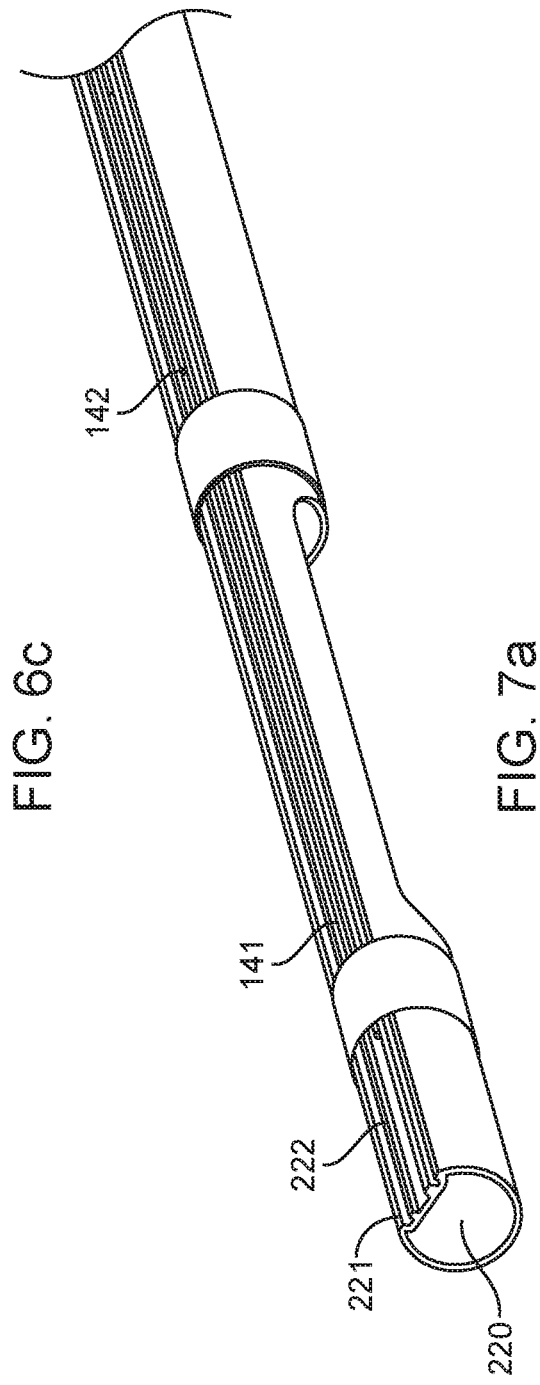
FIG. 7a shows a perspective view of a selective cut-out of the top of the Distal Lead Body of an electrical sensing/stimulation device, showing the Tissue Attachment Members in their retracted, straight configuration within the oval lumen, and the Ring Electrode Wires in their respective lumens, according to many embodiments.
Figure 7B:
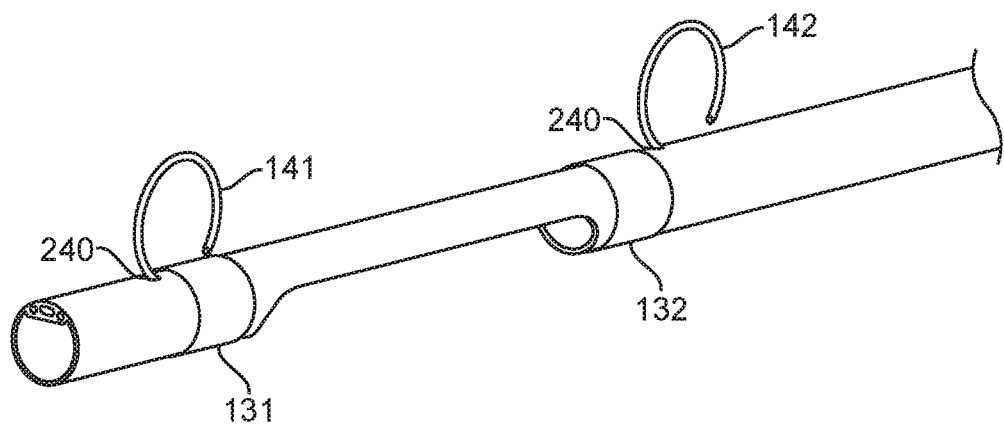
FIG. 7b shows a perspective view of a partial assembly of the Distal Lead Segment of FIG. 7a showing the Tissue Anchors in their deployed configuration.

As shown in FIGS. 6*a*, 6*a*', and 6*b*, each tissue attachment member(s) 141, 142 may comprise metallic, elastic, super-elastic, or shape-memory wire or tube, the distal end of each wire or tube having a formed loop that is capable of being straightened, and then reformed. The diameter of each wire or tube may range from 0.005" to 0.015", but is not so limited. As shown in FIGS. 6*a* and 6*b*, the tissue attachment member(s) 141, 142 may be attached side by side, at the region labeled 145 via laser welding, resistance welding, crimping (using a crimp tube), or by adhesive. In this region 145, the tissue attachment members may be keyed in the oblong-shaped lumen 222 such that they may not rotate in the lumen, and thus this "keying" (providing an interference fit between a driving and a following member) allows forward-backward translation of the tissue attachment member assembly 140. Vias or ports 240 may be cut through the lead body outer wall and into lumen 222 through which the tip and distal segment of the tissue attachment member(s) 141, 142 are deployed. As depicted in FIGS. 7*a* and 7*b*, it can be appreciated that upon proximal retraction of the tissue attachment assembly 140, the distal loop of each wire may assume a linear configuration when fully retracted into the oval lumen 222. In this configuration, with the tissue attachment members retracted into the lead body, the lead can be advanced through the appropriate vasculature or body chamber to the target destination.

As shown in FIG. 6*a*', the orientation of each tissue attachment member(s) 141', 142' may be reversed such that the tissue attachment member(s) 141', 142' are deployed through the deployment port 240 upon proximal retraction of the tissue attachment assembly 140', and retracted into the oval lumen 222 to assume a linear configurations upon distal advancement of the assembly 140'. This configuration may be keyed within the oval lumen 222 in exactly the same manner as for tissue attachment assembly 140.

FIG. 4*a* shows a vertical orientation of the oval lumen 402 within which the tissue attachment member(s) 141, 142 are oriented. In this configuration, it can be appreciated that the tissue attachment member(s) 141, 142 may be attached to each other in a vertical orientation, rather than a horizontal orientation.

Sensing/Stimulation Electrodes

Figure 7B:
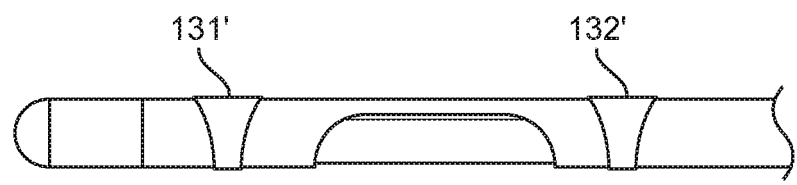
Figure 8A:
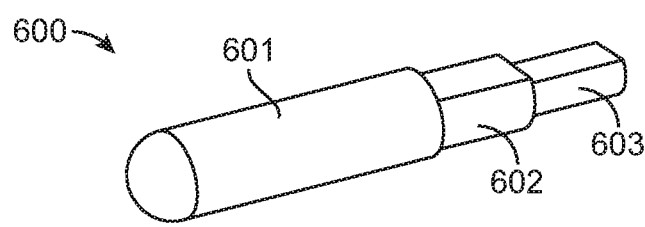
FIGS. 8a-8d depict various Distal Tips of the Distal Lead Segment, according to many embodiments.
Figure 8B:
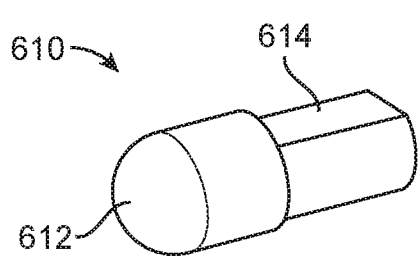
Figure 8C:
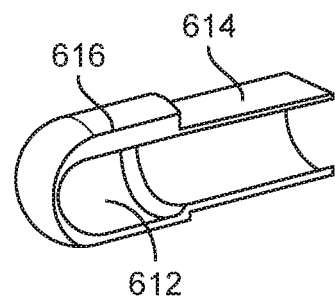
Figure 8D:
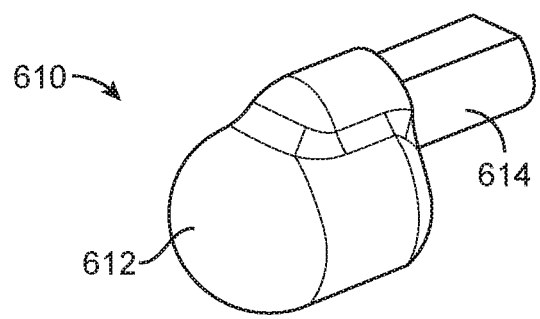

As shown in FIGS. 1 and 7, the electrode(s) 131, 132 may be mounted substantially on the surface of the lead body 120, but may also be embedded within the lead body 120 such that the appropriate surface area of the electrode(s) 131, 132 is exposed. The associated electrode conductor wire(s) 520 may be joined to the electrode(s) 131, 132 via laser welding, resistance welding or conductive adhesives. The conductor wire(s) 520 may pass from the electrode(s) 131, 132 through via(s) or port(s) 230 cut into the lead body 120 and into the electrode conductor wire lumen(s) 221. The electrode conductor wire(s) 520 may then run proximally along the length of the electrode conductor wire lumen(s) 221 to the lead handle 800. Alternatively or in combination, the lumen 221 may hold multiple electrode conductor wires 520. In this case, each electrode conductor wire 520 would require separate electrical insulation.

The electrodes may be generally cylindrically-shaped to fit around the outer surface of the lead body 120. The profile of the electrode(s) may be varied to provide a geometric shape such as a triangle, T-shape or trapezoid, but these examples do not limit the shapes that can be produced. The profile of the electrode can serve as a visual indicator when aligning the distal segment of the lead body 100 to the target tissue. FIG. 7*b*' shows an example of the electrodes 131', 132' configured to appear as a trapezoid when viewed under fluoroscopy. The electrodes 131', 132' can thus be mounted on the lead body 120 such that as the device is torqued into proper position at the target tissue site under fluoroscopy, the electrodes will appear as trapezoids, and indicating that the tissue attachment member ports 240 are properly aligned to the tissue to which the tissue attachment member(s) 141, 142 will be deployed.

The electrodes may also be fabricated in a non-cylindrical shape, such as a pad, disc, patch, linear member or a micro-array of point electrodes, all which may lie substantially on the surface of the lead body. These geometries may provide a more focused interface to the target tissue, providing more accurate ability to sense lower-threshold electrophysiological signals, and to also provide higher current densities when stimulating tissue, by virtue of delivering an equal amount of stimulation current via a smaller surface area than that of a ring electrode.

Atraumatic Tip

Referring to FIGS. 8*a*-8*d*, the lead distal segment 100 may also incorporate a distal atraumatic tip termination 600. The distal end of the main central lumen 220 may receive the proximal mounting inserts 602, 603 of the distal atraumatic tip 600. Feature 602 may be sized and configured to fit precisely within the end of the main central lumen 220, and the feature 603 may be sized and configured to fit within the lumen of the D-shaped element 310. Thus, the atraumatic tip may be joined to the central main lumen 220 and the D-shaped element 310 using adhesives, or by thermal joining, i.e., melting of these contact areas. The distal tip termination can also be configured as a small inflatable balloon 610. In this embodiment, the tip termination is hollow having a thin-walled bulbous tip, with one section of the bulbous tip being thicker 616, such that when the distal tip is inflated the balloon will expand eccentrically. This eccentric expansion can allow the tip to rest against the endocardial tissue in a very atraumatic fashion, but when inflated cannot act to displace the lead body, electrodes, and attachment member exit ports away from the target tissue. The balloon tip 610 may be inflated via the lead's main lumen 220, or may be inflated via a separate, dedicated lumen of the lead body 120.

Figure 18A:
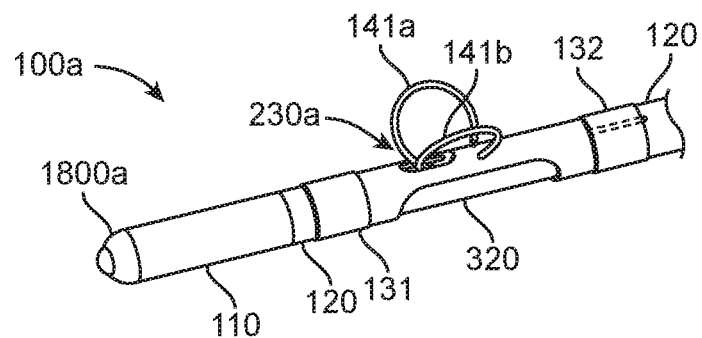
FIGS. 18a, 18b, 18c, 18d, 18e, 18f, 18g, 18h, and 18i show various Distal Tips of the Distal Lead Segment having integrated electrode(s), according to many embodiments.

As shown in FIGS. 18*a* to 18*i*, the lead distal segment 100*a* may include one or more tip electrodes. As shown in FIG. 18*a*, the lead distal segment 100*a* may have a tip that incorporates an integral "ball" or "spot" type electrode 1800*a*, positioned at the very distal end of the lead tip 110, or may be positioned at any radial location along the length of the tip 110. A very small diameter, flexible wire may be attached to the ball or disc electrode 1800*a* by laser welding, crimping, conductive adhesive or other electrical attachment methods known in the art. This electrode 1800*a* may serve the same stimulation function as the distal tip electrodes 131, 132, however since the "ball" or "spot" type electrode 1800*a* resides at a location on the low-durometer polymer atraumatic tip 110 of the lead distal segment 100*a*, and may be connected to a flexible wire, the tip 110 of the lead distal segment 100*a* can remain flexible and atraumatic. Another advantage of the "ball" or spot electrode 1800*a* as an integral part of the tip 110 may be to provide a fluoroscopic marker to indicate the distal tip 110 position during implantation of the device 100*a*. Alternatively, the "ball" 1800*a* may not serve as an active electrode (no wire attached), but only for fluoroscopic imaging.

Figure 18B:
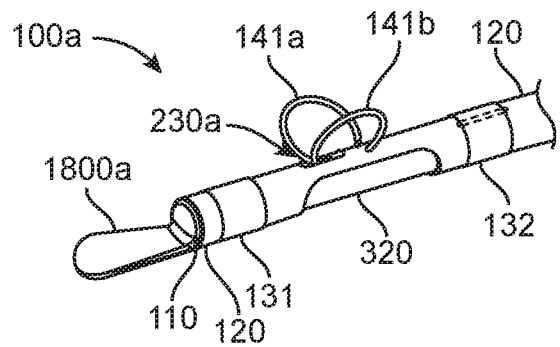
Figure 18C:
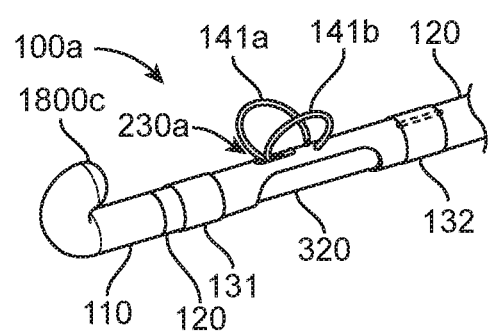
Figure 18D:
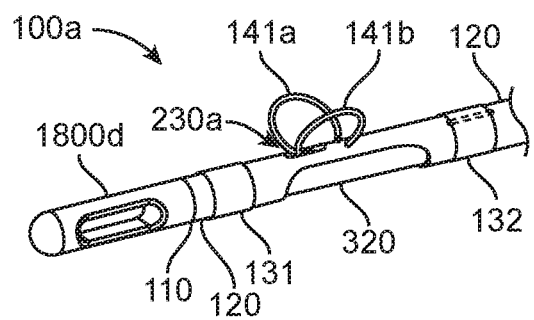
Figure 18E:
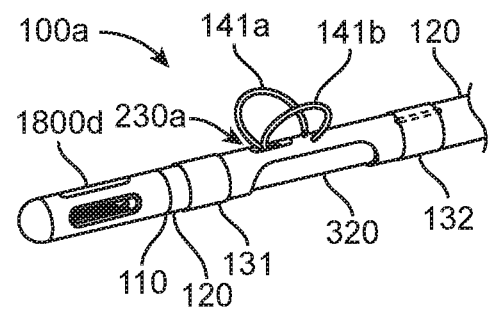
Figure 18F:
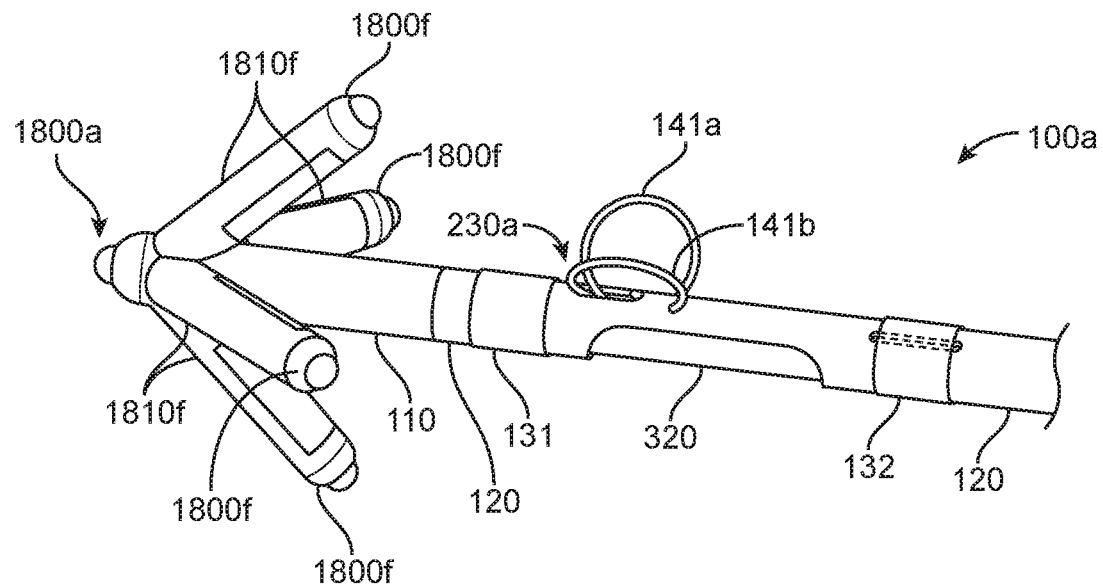

Other shapes for the atraumatic tip 110 are also contemplated. FIG. 18*b* shows a cobra-head atraumatic tip 1800*b*, which may be foldable to allow introduction into a sheath. FIG. 18*c* shows an elbowed tip 1800*c*, which may be foldable to allow introduction into a sheath. FIG. 18*d* shows a bilateral eccentric tip 1800*d*. FIG. 18*e* shows a quad-eccentric tip 1800*e*.

In some embodiments, the lead distal segment 100*a* may have a tip 110 that is configured with rearward-facing angled tines 1800*f*. The inner portion of each tine 1800*f* may be outfitted with an electrode 1810*f*. The tines 1800*f* may engage the trabeculated tissue in the apical region of the right ventricle RV, or other anatomical structures to provide a "passive fixation" of the lead's interface to the anatomy. Passive fixation may generally involve any feature of the device 100*a* that affixes to the tissue without any feature of the device 100*a* actually penetrating the tissue to provide fixation. Passive engagement may generally be achieved by the inner portion of the tine 1800*f* "hooking" around an anatomical feature such as trabecular bands, as are found in the apical region of the ventricles. Thus, the electrode placement at the inner aspect of each tine 1800*f* can directly interface to the anatomical feature that the tine 1800*f* has engaged.

Electrodes may also be placed at the distal end of each tine 1800*f* and/or at the distal tip of the lead body 120 itself. Bipolar sensing and pacing can thus be achieved from a multitude of electrode pairs. Other features of the lead may be similar to those features described above and herein, e.g. the band electrodes, the tissue stabilizers and the eccentric balloon. Any of these features many be used, or none may be used in combination with the tines 1800*f*.

Figure 18G:
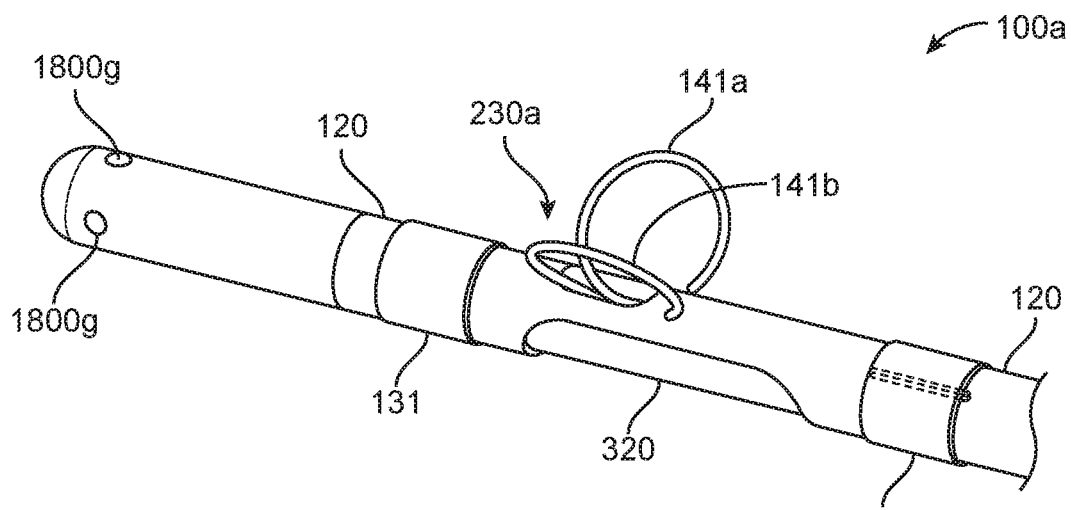
Figure 18H:
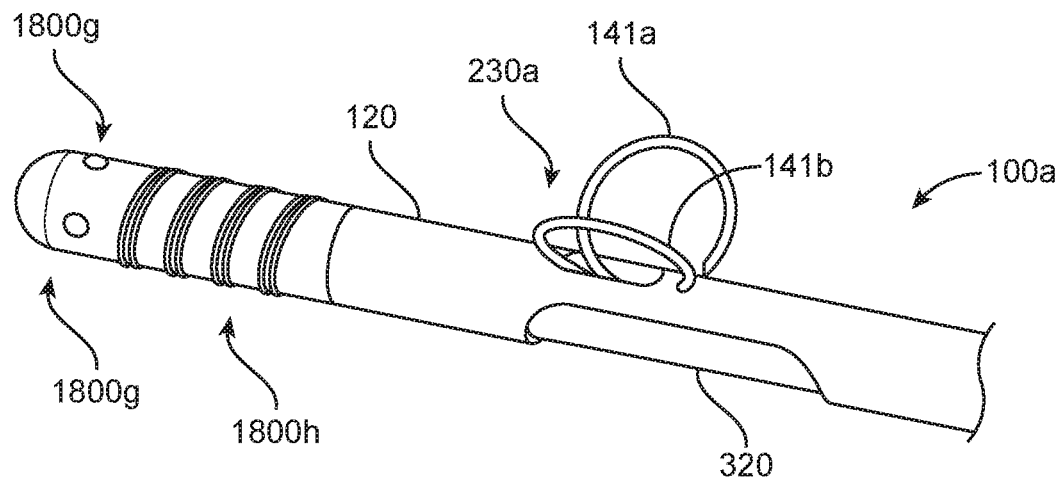
Figure 18I:
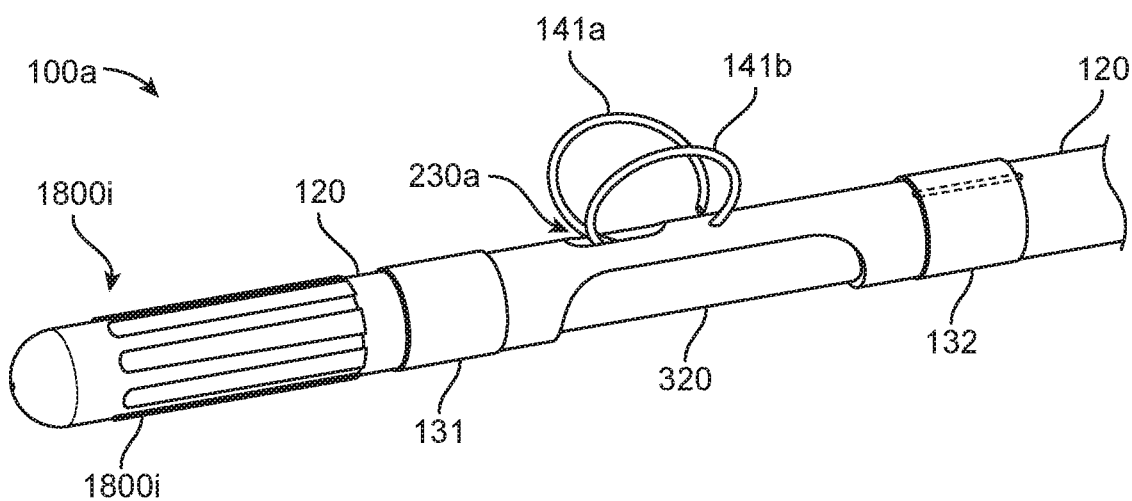

"Satellite" type electrodes 1800*g* may also be placed at various radial or circumferential locations about the lead tip 100*a* or the lead body 120, as shown in the FIGS. 18*g* and 18*h*. Single or double "helix" type electrode configurations 1800*h* may also be employed as shown in FIG. 18*i*. A double-helix configuration may allow a bi-pole electrode to be established between the two helices; however, one or both helix electrodes could also be used in conjunction with a ring-electrode to establish various configurations of bi-poles. One helix of the double helix may comprise a positive electrode and the other helix may comprise a negative electrode.

Laser-cut hypotubes can also be micro-machined to provide a multitude of electrode shapes and numbers. An example is shown in FIG. 18*i* wherein longitudinal electrodes 1800*i* have been fabricated from the laser-cut machining process.

Handle Assembly

Figure 10:
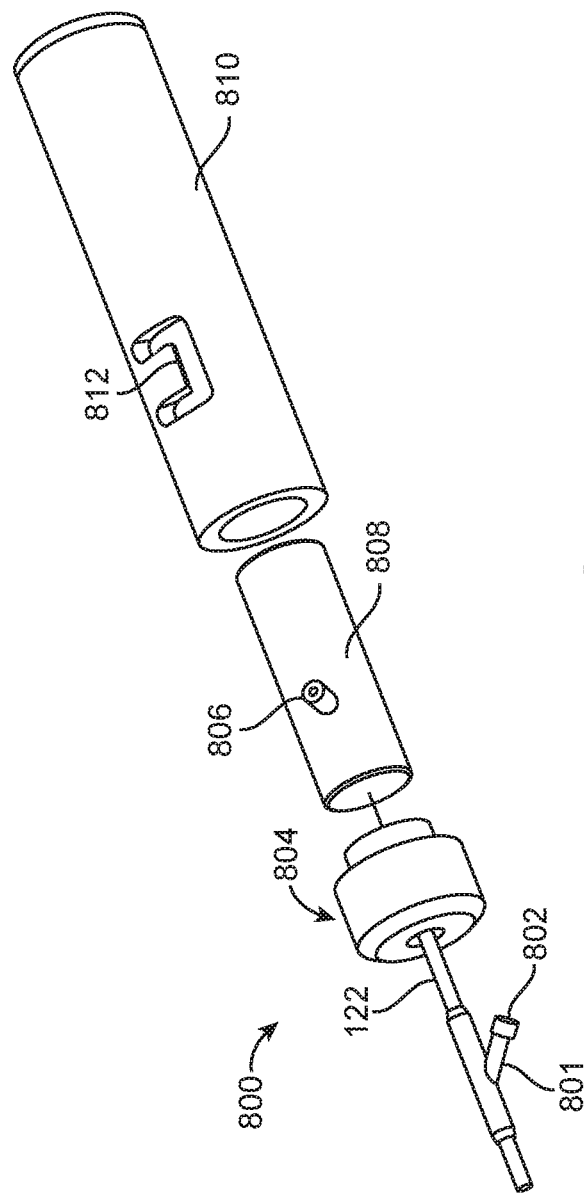
FIG. 10 shows a side view of a Lead Handle and actuation/locking mechanism, according to many embodiments.

The handle assembly 800 is shown in FIG. 10. The main components may comprise an outer handle body 810, an inner sliding actuator 808, and a handle faceplate 804. The proximal end of the lead body 122 may be attached to the handle faceplate using conventional joining methods such as epoxy or UV-cure adhesive. The handle faceplate 804 may be in turn attached to the outer handle body 810 using similar joining techniques. Turning the handle assembly 800 about its axis can thus transmit rotational movement and torque to the lead body 120 via the torque control member 710, 720 or 730. Alternatively or in combination, the lead body 120 may be rotated using a control member on the handle assembly 800 while the handle assembly remains stationary relative to the lead body 120. Within the outer handle body 810 may be an inner sliding actuator 808. The proximal end of the tissue attachment assembly 140 may emerge from the proximal end of the lead body 122 and may be attached to the inner sliding actuator 808 using conventional joining methods such as epoxy or UV-cure adhesive. A finger or thumb-operated knob 806, or other actuation mechanism, such as a switch, button, slider, or the like, can be mounted into the inner sliding actuator 808. The knob 806 may pass through a C-shaped channel 812 in the outer handle body 810. When moved to its furthest proximal position in the channel, the tissue attachment members 141, 142 may be completely retracted into the lead body, as shown in FIG. 7*a*. The knob 806 may then be moved, for example, laterally, within the C-shaped channel 812 to lock the position of the inner sliding actuator 808. To advance/deploy the tissue attachment members, the knob 806 may be moved laterally to the longitudinal portion of the C-channel, and then advanced forward. This action may deploy the tissue attachment members 141, 142. The knob 806 may then be moved laterally within the C-shaped channel 812 to lock the position of the inner sliding actuator 808 in the deployed configuration. The "C-shaped" channel 812 is but one template to guide the movement of the knob 806 for the deployment, locking and retraction of the tissue attachment members 141,142. Other such templates may be contemplated. One such channel may comprise a be a "Z-shaped" channel wherein the top and bottom horizontal segments of the Z-shape are oriented perpendicular to the axis of the handle body, and the terminal ends of the top and bottom horizontal segments of the Z-shape may be used as lock positions for the knob 806. The knob 806 may translate along the diagonal portion of the Z-channel (connecting the top and bottom horizontal segments) to deploy and retract the tissue stabilizers.

At the proximal segment of the lead body 122, a Y-adapter 801 may be mounted onto the lead body. The Y-adapter may be attached and sealed to the lead body 122 at both proximal and distal ends. A small cutout in the lead body and into the main lumen 220 allows communication of air or fluid from the Y-adapter port 802. This port may be configured as a standard type luer connector known commonly in the industry. Similar Y-adapters may be used as a directional conduit for the electrode wire to exit at the proximal region of the lead and terminate in a plug that is used to connect the lead to the external pacemaker.

Figure 10A:
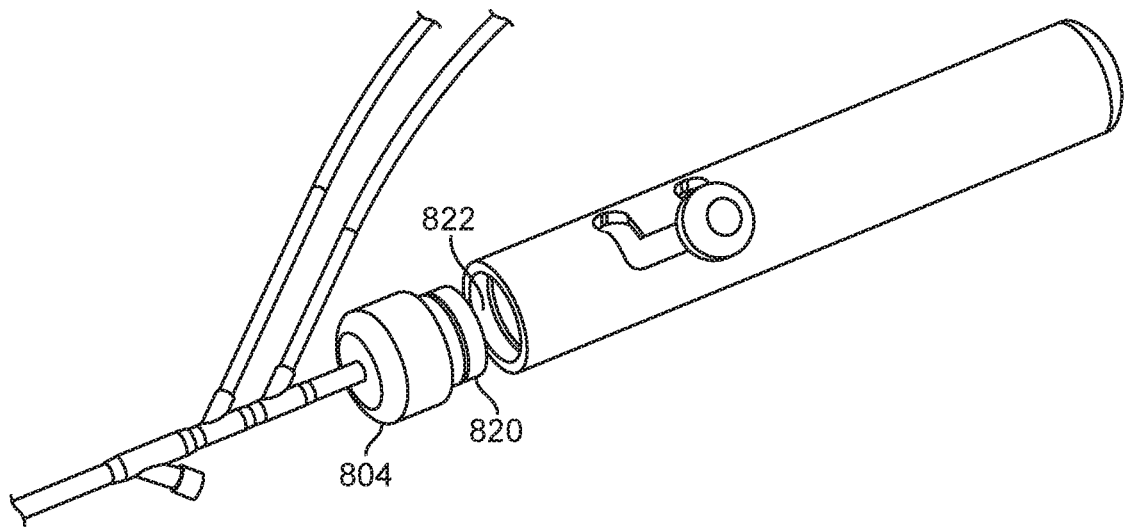
FIG. 10a shows a side view of a Lead Handle and rotation mechanism, according to many embodiments.
Figure 10B:
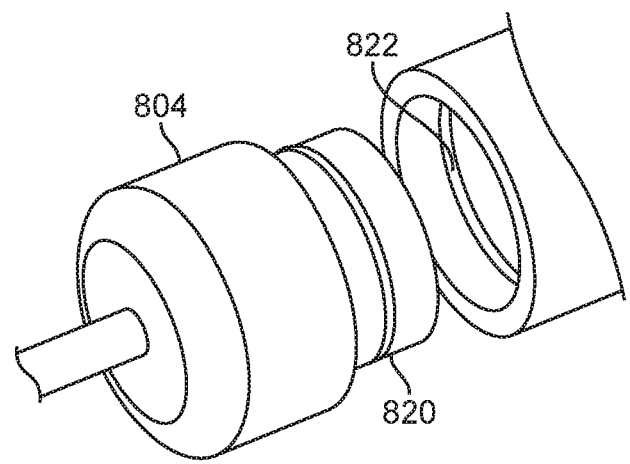

Referring now to FIGS. 10A to 10B, the handle faceplate 804 may be free to rotate about the distal end of the handle. The handle faceplate 804 may have a circumferentially raised ring 820 that locks into place with a mating circumferential groove or detent 822 in the distal inner diameter of the handle body 810. To assemble, the handle faceplate 804 may simply be pushed onto the handle body, thus "snapping" the two parts together. A sufficient gap may be allocated in the mating of the raised ring 820 and the circumferential groove or detent 822 such that the handle faceplate may rotate freely about the handle body.

Rotation of the handle faceplate 804 may rotate the lead body 120 due to the connection between the faceplate 804 and lead body 120. As the handle faceplate 804 and lead body are rotated, it may be desirable for the proximal end of the tissue attachment assembly 140 to also freely rotate within the internal handle shuttle 808, yet maintain capability to translate the tissue attachment assembly 140 distal and proximal to deploy and retract the tissue attachment members. This can prevent wind-up of the proximal wire of the tissue attachment assembly 140.

Figure 10C:
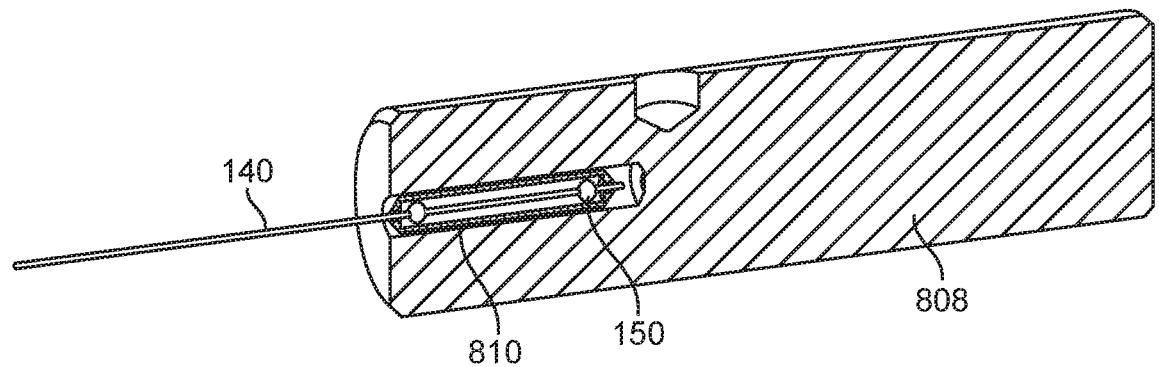
FIG. 10c shows a section view of a Lead Handle and rotation mechanism, according to many embodiments.
Figure 10D:
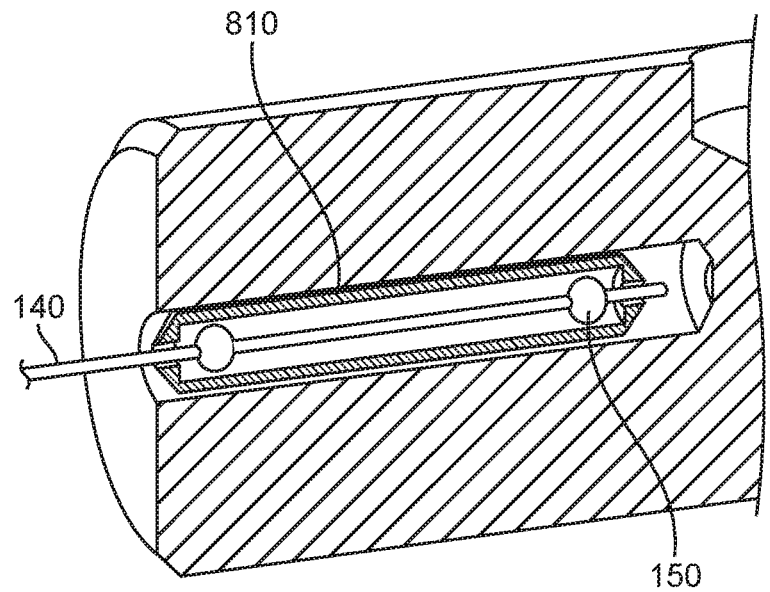
FIG. 10d shows a magnified view of the rotation mechanism of FIG. 10c.

Referring to FIGS. 10C and 10D, one way to provide this functionality is to capture the proximal end of the tissue attachment assembly 140 (wire) within a hypotube sleeve 810 that is affixed within the internal handle shuttle 808. The proximal end of the wire of the tissue attachment assembly 140 may have circumferential raised features 150 that can be free to rotate within the hypotube sleeve 810, and the ends of the hypotube sleeve 810 may be crimped to a lesser diameter such that upon distal/proximal translation of the hypotube sleeve 810 and handle shuttle the circumferential features of the wire 150 will abut against the end-crimps of the hypotube sleeve, thus moving the wire 140 distal/proximal, yet the proximal end of the tissue attachment assembly 140 (wire) is free to rotate within the hypotube sleeve 810.

Orientation of Lead Body Towards Target Tissue

Figure 9A:
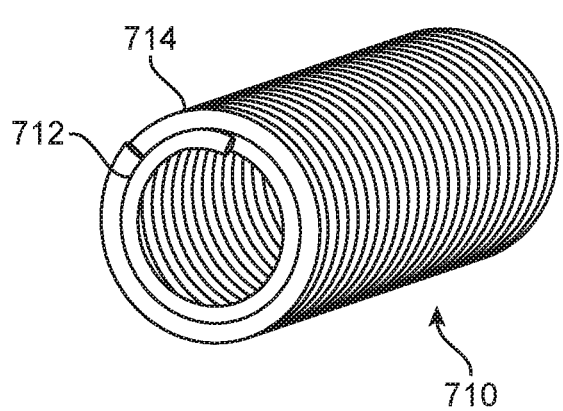
FIGS. 9a, 9b, and 9c show side views of Torque Control Members, according to many embodiments.
Figure 9B:
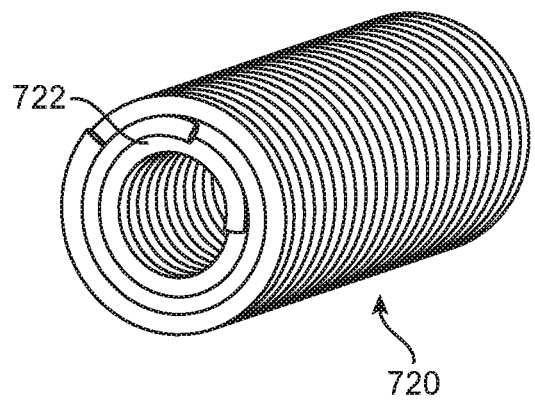
Figure 9C:
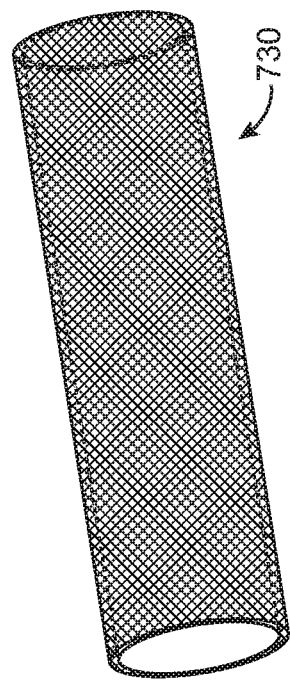

It is generally appreciated that the procedural alignment of the distal segment of the lead body towards the target tissue may be greatly facilitated by the use of the torque control members in FIGS. 9a-9c. Other methods may also be employed such as using a preformed two-dimensional or three dimensional internal stylet positioned within the lead body, or shaping of the lead body itself. The stylet may be permanently mounted within the lead body, or may be configured to be advanced distally and retracted proximally as required during the delivery and implantation of the lead. The stylet may also be configured to be completely removable from the lead body once its use is completed in the implant procedure. In either case, the pre-shapes of the stylet, or the pre-shape of the lead body itself may be formed to follow and naturally align to the anatomical pathway to the target tissue. As an example, for delivery of the lead to the right ventricle of the heart, and via access through the internal jugular vein, a specific shape can be set into either the stylet or lead body that conforms to the entrance into the internal jugular vein, through the innominate vein, through the superior vena cava, through the right atrium, and into the right ventricle. This fundamental two-dimensional or three-dimensional pathway may be formed into the lead such that when the distal lead has been delivered to the right ventricle the lead will be urged to "self-align" to this pathway. Further, the displacement member 320 can be oriented such that when the lead is "self-aligned" the displacement member 320 will be substantially in the correct orientation within the right ventricle, also positioning the tissue attachment members 141, 142 towards the target implantation site. These alignment techniques and embodiments may be used in conjunction with directional radiopaque marker band(s). Marker band(s) may also be used as a rotational indicator as described earlier in the trapezoid shapes of the electrodes. The trapezoid is an example of an eccentric shape that when viewed under fluoroscopy may face in a unique direction. Incorporating the eccentric shape into an electrode is an example of how to embody the eccentric rotational marker, but the marker may be a separate full or partial band fashioned with eccentric features.

The distal lead segment 100 may also be configured such that it is rotatable about the elongate lead body 120. In this configuration, the proximal end of the distal lead distal segment 100 may be rotatably attached to the distal end of the elongate body 120, and the proximal end of the elongate body is connected to a rotatable face, or dial on the handle, via an elongate rotatable member lying within the elongate body 120. Thus, turning the dial or faceplate on the handle couples the rotational movement to the distal lead segment 100, while the elongate lead body remains stationary and does not rotate.

Tissue Stabilizer Embodiments

Figure 11A:
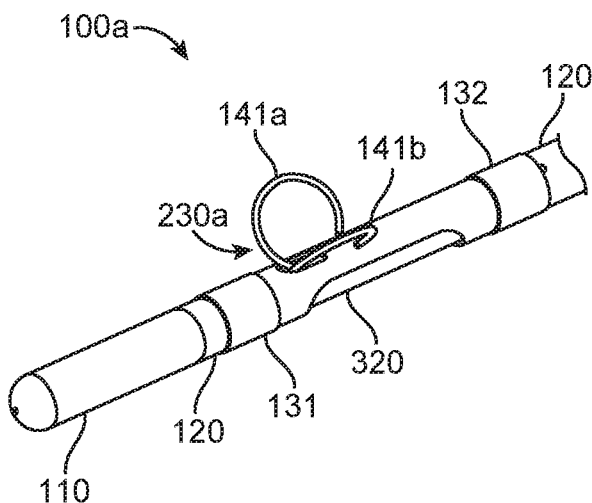
FIG. 11a shows a perspective view of the Distal Lead Segment of an electrical sensing/stimulation device, with the Tissue Attachment Members deployed from a common port to be separated from one another by about 90°, according to many embodiments.
Figure 11B:
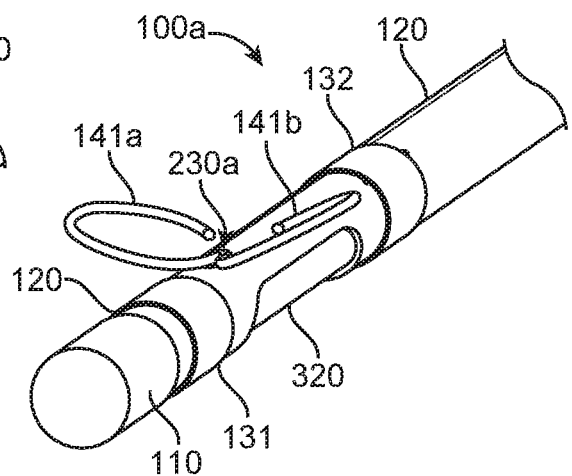
FIG. 11b shows a perspective view of the Distal Lead Segment of an electrical sensing/stimulation device, with the Tissue Attachment Members deployed from a common port to be separated from one another by greater than 90°, according to many embodiments.
Figure 11C:
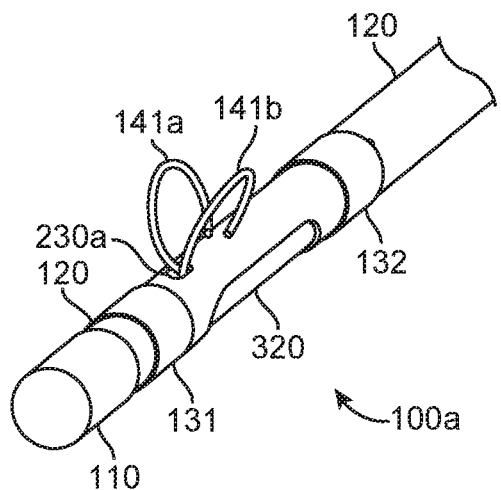
FIG. 11c shows a perspective view of the Distal Lead Segment of an electrical sensing/stimulation device, with the Tissue Attachment Members deployed from a common port to be separated from one another by less than 90°, according to many embodiments.
Figure 11D:
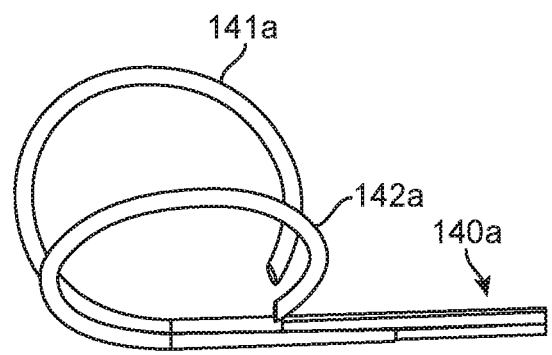
FIG. 11d shows the Tissue Attachment Member Assembly of FIGS. 11a to 11c.
Figure 11E:
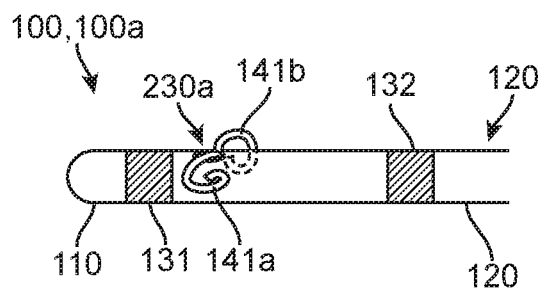
FIG. 11e shows a side view of the Distal Lead Segment of an electrical sensing/stimulation device with Tissue Attachment Members oriented toward the Lead Body, according to many embodiments.
Figure 11F:
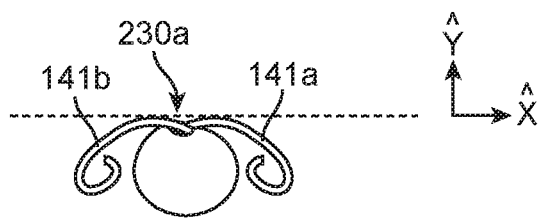
FIG. 11f shows a front view of the Distal Lead Segment of FIG. 11e.

As discussed above and herein, the tissue stabilizers or attachment members 141 and 142 may be longitudinally separated and within the same deployment "plane". Alternatively or in combination, a plurality of tissue stabilizers or attachment members 141a and 142a may deploy from a common deployment port 230a of the lead distal segment 100a of the lead body 120. The tissue stabilizers or attachment member loops 141a and 142a may be separated by an angle from 0° to more than 180°. FIGS. 11a-11d show tissue stabilizers or attachment member loops 141a and 142a that are separated by 20° to 90°, although such ranges are not limiting. FIGS. 11a to 11c show the tissue stabilizers or attachment member loops 141a and 142a extending from the common deployment port 230a. In FIG. 11a, the tissue stabilizers or attachment member loops 141a and 142b are separated by about 90°. In FIG. 11b, the tissue stabilizers or attachment member loops 141a and 142b are separated by greater than 90°. In FIG. 11c, the tissue stabilizers or attachment member loops 141a and 142b are separated by less than 90°. FIG. 11d shows the tissue attachment assembly 140a comprising the tissue stabilizer or attachment member loops 141a and 142b alone. In some embodiments, each stabilizer 141a or 142a forms a loop of a constant radius. Alternatively or in combination, the tissue attachment members 141 and 142 may face toward the surface of the distal lead body 100 or 100a as shown in FIGS. 11e and 11f. The tissue attachment members 141 and 142 may initially face away from the surface of the distal lead body 100 or 100a before curving back toward the surface of the distal lead body 100 or 100a. In FIGS. 11e and 11f, the tissue stabilizers or attachment member loops 141a and 142b are separated by more than 180°, such as about 270°.

Figure 12A:
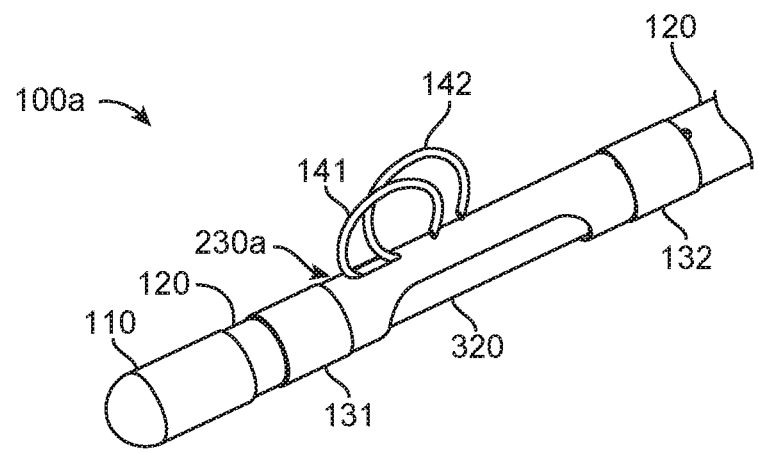
FIG. 12a shows a perspective view of the Distal Lead Segment of an electrical sensing/stimulation device, with the Tissue Attachment Members deployed from a common port to be axially/longitudinally separated but coplanar, according to many embodiments

The attachment members or tissue stabilizers 141 and 142 may also be co-planar and exit from a common deployment port 230a as shown in FIG. 12a. The axial or longitudinal separation between the attachment members or tissue stabilizers 141 and 142 may vary from 0.050" to 0.100", but is not so limited. A point of separation may be reached wherein the stabilizers no longer overlap and are actually "separated" from each other. In such cases, a common deployment port 230a (as in FIG. 12a) or separate deployment ports 230 may be utilized.

As discussed above and herein, two tissue stabilizers or attachment members 141/141a and 142/142a are deployed. However, the number of tissue stabilizers or attachment members may be increased to 3, 4, or other numbers, or reduced to one tissue attachment member. The locations of the additional tissue stabilizers may also vary radially and longitudinally along the lead body.

Figure 12B:
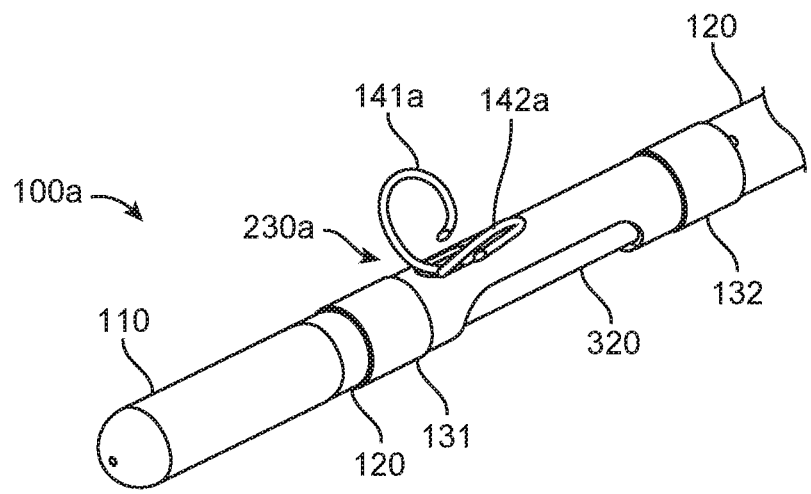
FIG. 12b shows a perspective view of the Distal Lead Segment of an electrical sensing/stimulation device, with the Tissue Attachment Members deployed from a common port and having a decreasing end loop radius, according to many embodiments.

As discussed above and herein, and as shown in FIG. 12b, for example, the tissue stabilizers or attachment members (wire loops) 141/141a and 142/142a may have a looped end with a constant radius when in the deployed configuration. This radius may practically range from 1 mm to 5 mm, but is not so limited.

Figure 12C:
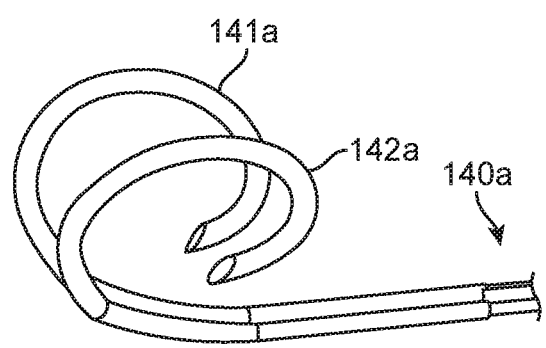
FIG. 12c shows a perspective view of the Tissue Attachment Member Assembly of an electrical sensing/stimulation device, with the Tissue Attachment Members having end loops which decrease in radius along their length, according to many embodiments.

As shown in FIG. 12c, for example, the radius of the deployed tissue stabilizers 141/141a and 142/142a may decrease along the length of the wire loop end, from the proximal section of the loop to the distal section of the loop. Alternatively or in combination, the radius of the deployed tissue stabilizers 141/141a and 142/142a may increase along the length of the wire loop end, from the proximal section of the loop to the distal section of the loop.

Figure 13A:
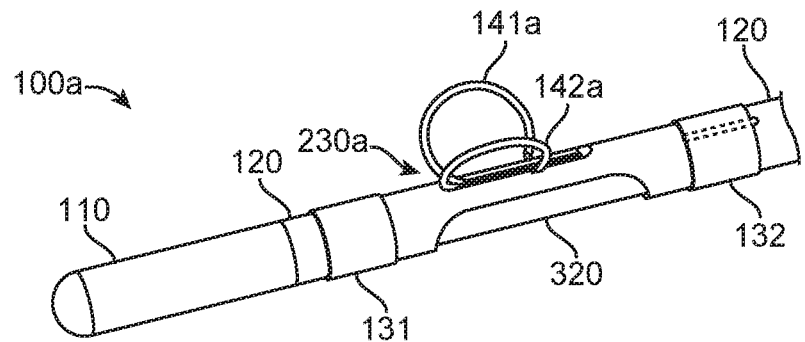
FIG. 13a shows a perspective view of the Distal Lead Segment of an electrical sensing/stimulation device, with the Tissue Attachment Members deployed from an elongated common port and translated to the distal end of the port, according to many embodiments.
Figure 13B:
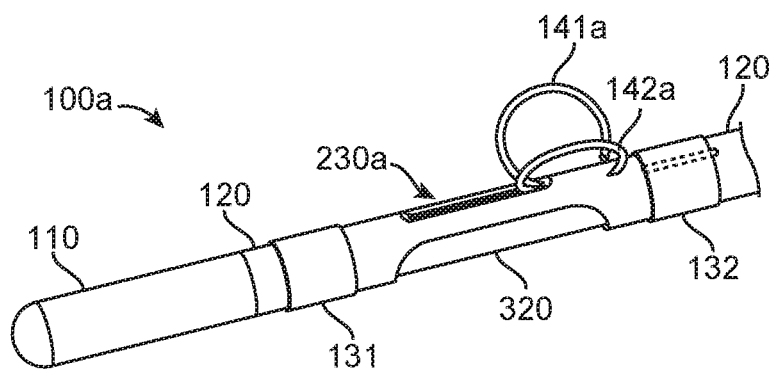
FIG. 13b show a perspective view of the Distal Lead Segment of FIG. 13a, with the Tissue Attachment Members translated to the proximal end of the port.

As shown in FIGS. 13a and 13b, the length of the deployment port 230a for the attachment members or tissue stabilizers 141a and 142a may be lengthened to allow the lead body 120 to translate over the linear portion of the tissue stabilizer wire 140a (within the lead body 120). This allowance of movement of the lead body 120 over the stabilizer wire(s) 140a can permit the lead 100a to move freely in response to intra-cardiac forces during contraction, while the tissue stabilizer loops 141a, 142a remain securely implanted in the myocardium. FIGS. 13a and 13b show the position of the stabilizers 141a, 142a when translated to the distal end of the deployment port 230a (FIG. 13a) and the proximal end of the deployment port 230b (FIG. 13b).

Figure 14:
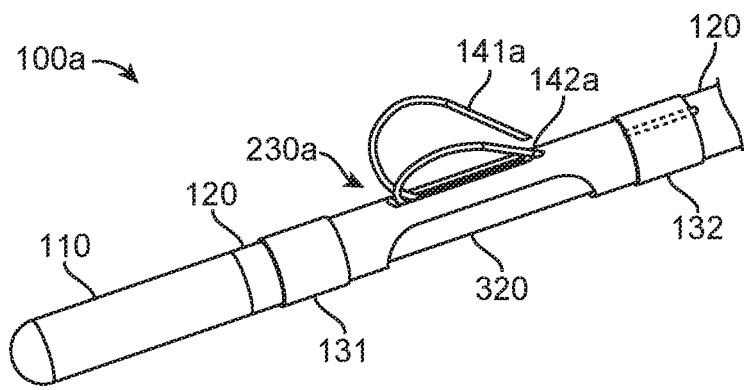
FIG. 14 shows a perspective view of the Distal Lead Segment of an electrical sensing/stimulation device, with the Tissue Attachment Members deployed from an elongated common port and having straightened ends, according to many embodiments.

As shown in FIG. 14, the attachment members or tissue stabilizers 141a, 142a may have distal segments of the end wire loop that are somewhat straightened, such that upon the initial deployment of the end wire loop, the straight distal segment may extend and "reach" further radially away from the lead body 120, before the "loop" segment of the wire emerges from the lead's deployment port 230a. This can allow the tissue stabilizers 141a, 142a to purchase as much tissue as possible to afford a secure attachment to the myocardium. As shown, the straightened segment is at the distal tip of the attachment member or tissue stabilizer 141a, 142a; however, the straightened segment can be located anywhere along attachment member or tissue stabilizer.

Figure 15A:
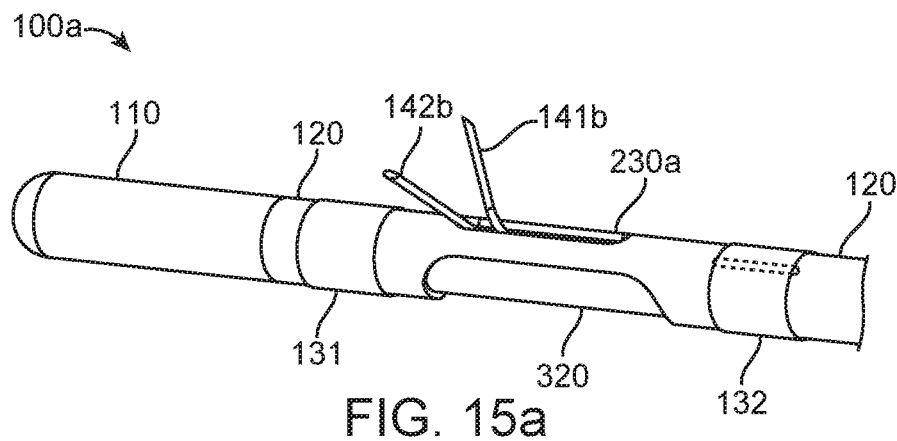
FIG. 15a shows a perspective view of the Distal Lead Segment of an electrical sensing/stimulation device, with the Tissue Attachment Members deployed from an elongated common port and comprising a hollow tube, according to many embodiments.
Figure 15B:
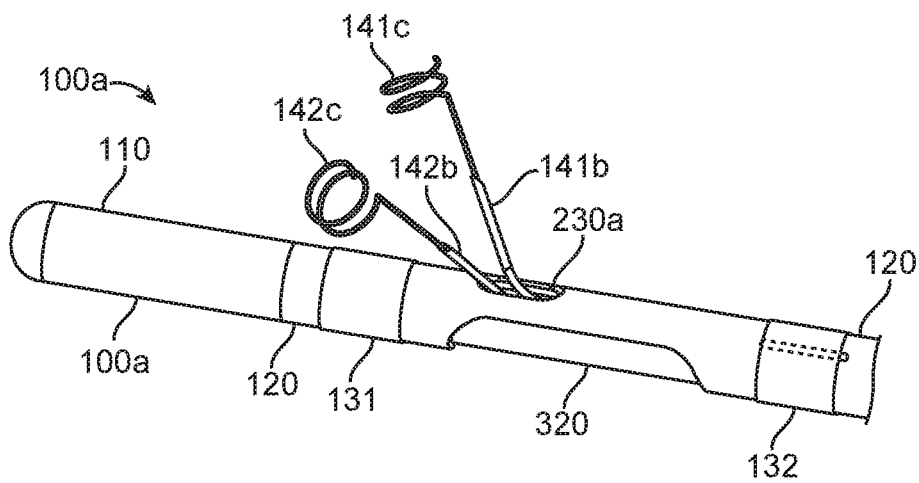
FIG. 15b shows a perspective view of the Distal Lead Segment of FIG. 15a where helical anchor wires are deployed from the deployed Tissue Attachment Members.
Figure 15C:
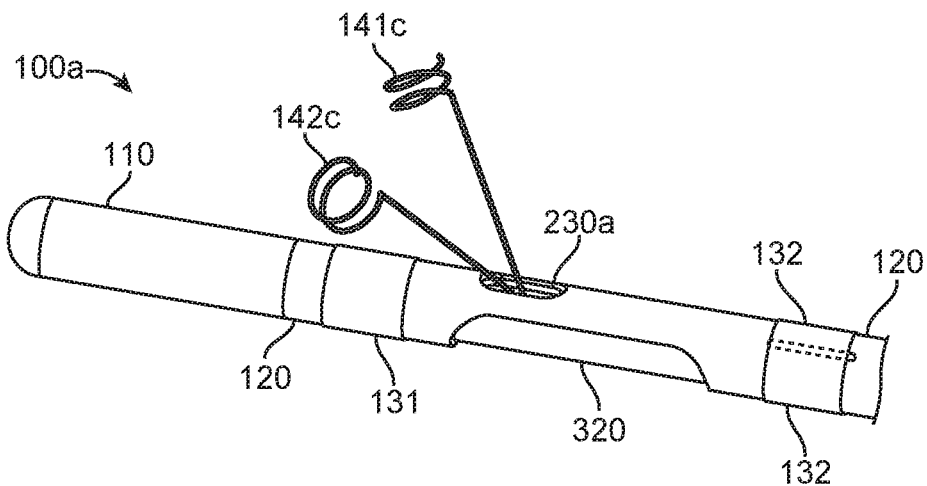
FIG. 15c shows a perspective view of the Distal Lead Segment of FIG. 15a where the helical anchor wires are deployed and the Tissue Attachment Members are retracted.

As shown in FIGS. 15a to 15c, tissue stabilizer members 141b, 142b may be tubular in construction, e.g. a hypotube or hypodermic type needle. As shown in FIG. 15a, the tissue stabilizer members or needles 141b, 142b may deploy from the common deployment port 230a similar to the manner described above and herein. It can be appreciated that the stabilizer needle(s) may also deploy from separate ports 240 of FIG. 7b. Within the tissue stabilizer members or needles 141b, 142b may reside one or more translatable anchor-wires 141c, 142c, respectively, the distal end of the wires 141c, 142c being pre-shaped into a small helix, spiral, or pigtail, as an example, but not so limited. The material chosen for the anchor-wires 141c, 142c may be of a shape-memory material to allow the pre-formed helix to straighten as the distal ends of the anchor-wires 141c, 142c is translated within the needles 141b, 142b, respectively, and then reform the helix, such as when penetrating tissue, as the distal ends of the anchor-wires 141c, 142c are advanced beyond the ends of the needles 141b, 142c as shown in FIG. 15b. The needles 141b, 142b may penetrate into the target tissue, upon which the distal ends of the translatable anchor-wire 141c, 142c may be advanced into the target tissue to reform the helix. The needles 141b, 142b may then be retracted back into the lead body 120 as in FIG. 15c, leaving the anchor-wire and reformed helix implanted within the target tissue. The anchor-wires 141c, 142c may be constructed from 0.002"-0.008" diameter Nitinol wire, other shape-memory alloy, or other shape-memory monofilament, braided or stranded material, though the wire or monofilament is not so limited to the diameters given.

As shown in FIG. 15c, the needle stabilizers 141b, 142b may be retracted back within the lead body 120. The anchor-wires 141c, 142c may now also be slightly retracted back into the lead body to remove any "slack" in the straight section of the anchor wire 141c, 142c and to pulling the lead body 120 and electrodes 131, 132 against the tissue site where the distal end of the anchor-wires 141c, 142c are implanted.

Figure 16A:
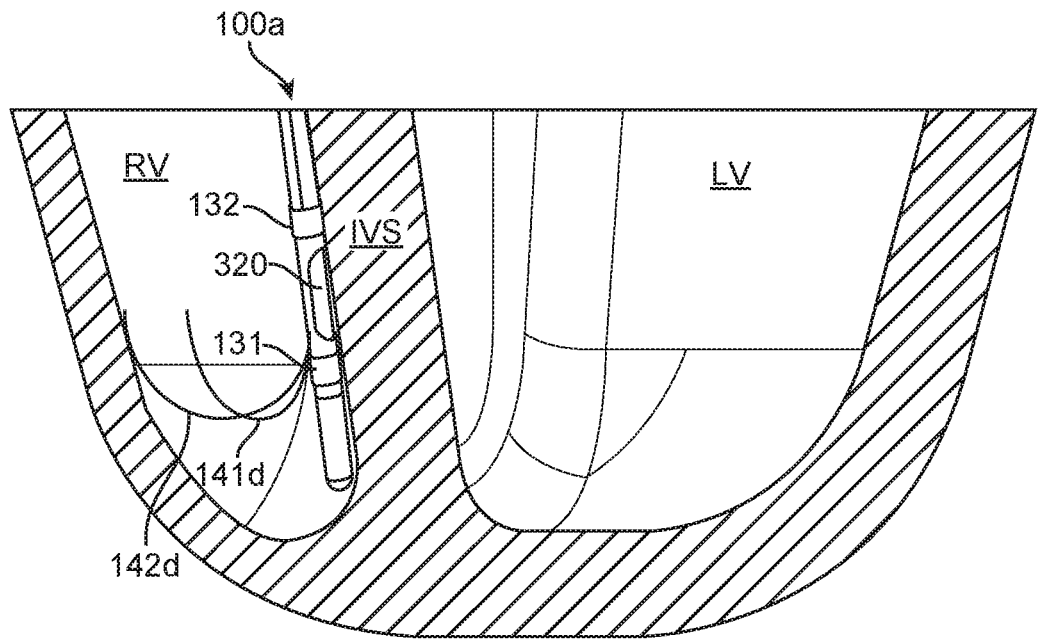
FIG. 16a shows a section view of the Distal Lead Segment of an electrical sensing/stimulation device introduced into a heart ventricle, with large-diameter biasing loops deployed, according to many embodiments.
Figure 16B:
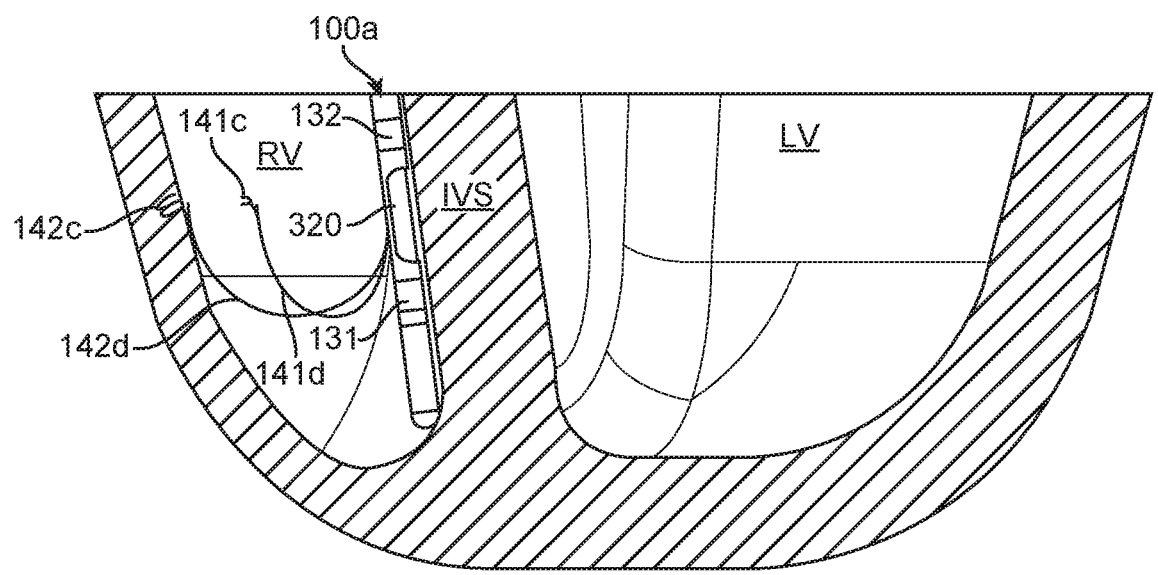
FIG. 16b shows a section view of the Distal Lead Segment of FIG. 16a, with large-diameter biasing loops deployed and anchor-wires extending from the loops.

As shown in FIGS. 16a and 16b, the lead distal segment 100a (placed into the right ventricle RV) may have one or more large-diameter curved biasing-loops 141d, 142d for deploying and securing an attachment of the lead distal segment 120 to a cardiac structure (such as the interventricular septum IVS separating the right ventricle RV with the left ventricle LV). These biasing-loops 141d, 142d may be deployable and retractable similarly to the tissue stabilizers described above and herein. As the biasing-loops 141d, 142d are deployed, they may have sufficient "reach" to engage the tissue opposite the lead body 120 as shown in FIG. 16a. In some embodiments, no balloon inflation is necessary to wedge the lead body 120 against the interventricular septum (that is, the deployment of the biasing-loops 141d, 142d may be sufficient to push and position the lead body 120 as desired). Thus, as the distal ends of the biasing-loops 141d, 142d engage the tissue opposite the lead body 120 (free wall tissue in FIGS. 16a, 16b) the lead body 120 can be moved in the opposite direction and against the interventricular septum IVS, i.e. the lead 120 and deployed biasing-loops 141d, 142d may now be wedged between the ventricular free wall and interventricular septum IVS, as an example. In some embodiments, the biasing-loops 141d, 142d may comprise electrodes such that the biasing-loops 141d, 142d may serve as pacing leads.

Further, each biasing-loop 141d, 142d may also have a sharpened distal end to penetrate tissue and/or include translatable anchor-wires 141c, 142c, as described above and herein. FIG. 16b shows the translatable anchor-wires 141c, 142c being deployed from the distal end of the biasing-loops 141d, 142d. The lead distal segment 120 of FIG. 16b is shown in FIG. 16c without the heart to provide a better image of the biasing-loops 141d, 142d and the anchor-wires 141c, 142c.

Figure 16C:
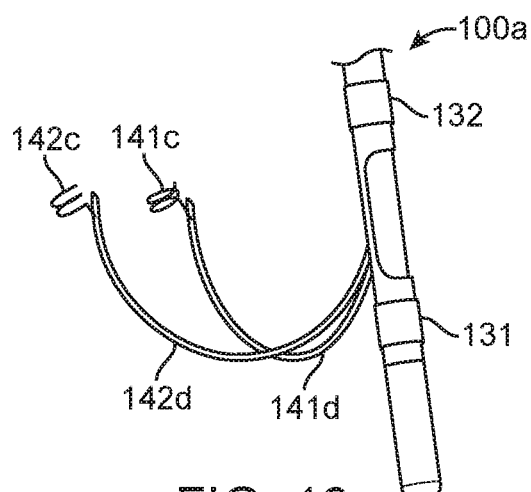

In the FIG. 16c, the anchor-wires 141c, 142c are shown to emerge from a port located on the side of the biasing-loops 141d, 142d, however, the anchor-wires 141c, 142c may alternatively emerge from the distal ends of the biasing loops 141d, 142d. The distal ends of the biasing loops 141d, 142d may penetrate the tissue, or the distal segments of the biasing-loops 141d, 142d may simply rest against the tissue. In either case, the distal lead segment 100a may be biased away from the biasing-loops 141d, 142d and against the target tissue (tissue to be paced by the electrodes 131, 132). FIG. 16c shows a single anchor-wire 141c, 142c extending from biasing-loops 141d, 142d, respectively, but in some embodiments, multiple anchor-wires may extend from a single biasing loop 141d or 142d.

With respect to the deployment of the stabilizers 141/141a, 142/142a, the stabilizer-needles 141b, 142b, or the biasing-loops 141d, 142d ("deployable members"), proper radial deployment of these members 141/141a, 142/142a, 141b, 142b, 141d, 142d may require precise control. If these member 141/141a, 142/142a, 141b, 142b, 141d, 142d are allowed to simply rest within the deployment lumen 222 of the lead body 120, upon torqueing of the device the lead body 120 and the deployable members 141/141a, 142/142a, 141b, 142b, 141d, 142d may experience different amounts of torsion and thus the deployment members 141/141a, 142/142a, 141b, 142b, 141d, 142d may lose their deployment alignment with the deployment port 230, 230a of the lead body 120. Thus, "keying" of the deployable members 141/141a, 142/142a, 141b, 142b, 141d, 142d within the deployment lumen may be critical to maintain the deployment member's deployment alignment to the deployment port.

Figure 17A:
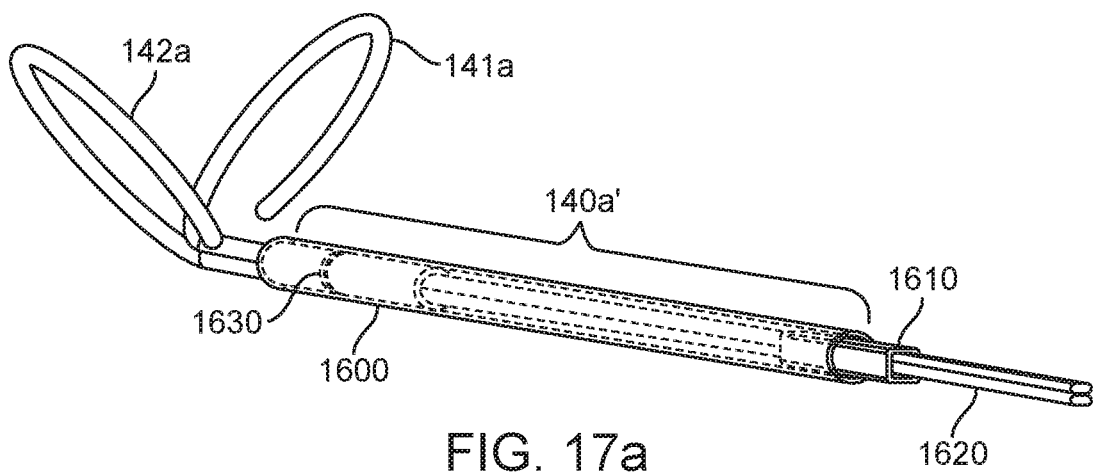
FIG. 17a shows a "keyed" Tissue Attachment Member Assembly, according to many embodiments.
Figure 17B:
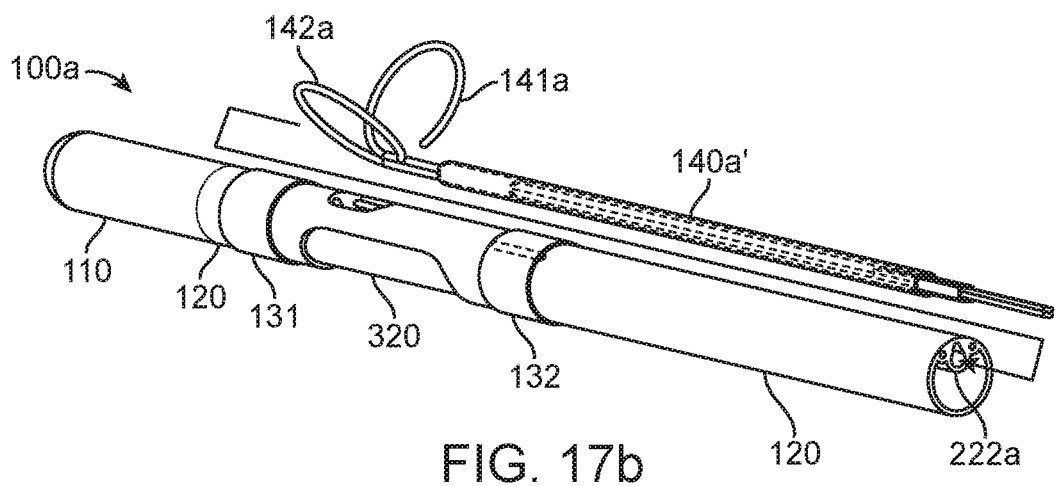
FIG. 17b shows the "keyed" Tissue Attachment Member Assembly of FIG. 17a and the Distal Lead Segment of an electrical sensing/stimulation device.

Techniques for such "keying" are shown, for example, in FIGS. 17a and 17b. The straight segment of each stabilizer wire 141a, 142a may be flattened, and when mated they form a square cross-section that can translate in a stainless steel hypotube 1610, the inner diameter of which can be precision shaped into a square cross-section (the "key"). Thus, as the stabilizers 141a, 142b are translated back and forth (deployment and retraction) the stabilizer wires 141a, 142b may remain aligned within the stainless steel hypotube 1610 shaped with a mating square cross-sectional profile. While the "key" may have a square cross-section, other shapes such as a rectangle, triangle, trapezoid, pentagon, to name a few, may also be used.

Further, the "key" should not move or rotate within the deployment lumen 222a of the lead body 120. Thus the key must be secured (glued, bonded) within the deployment lumen of the lead body 120. Thus, to secure the "key," another component, a "guide tube" 1600, may be provided. The key-guide tube assembly 140a' may be inserted into the deployment lumen 222 of the lead body 120 and affixed in place using adhesives. The "guide tube" 1600 may serve many purposes: (1) it can securely hold the "key" in place within the deployment lumen 222a, and (2) it can also serve as a secure containment "garage" as the tips of the stabilizers 141a, 142a are fully retracted within the lead body 120. With respect to the latter function—if the stabilizers tips are retracted to within the deployment lumen 222a of the lead body 120 (lead body 120 may be of a lower durometer polymer), the tips can dig into the polymer, thus halting their deployment. However, the "guide tube" 1600 may be fabricated from a material with a hard surface finish (e.g. Nitinol, high durometer Hytrel polymer, Nylon, to name a few) such that the stabilizer tips may glide along the inner surface of the guide tube 1600, allowing free retraction and deployment of the stabilizers 141a, 142a. As shown in FIG. 17b, the guide tube 1600 can be mounted within the deployment lumen 222a of the lead body 120. In many embodiments, a fluid tight seal 1630, such as an O-ring, may be provided between the inner surface of the guide-tube 1600 and the tissue attachment mechanism to prevent fluid leakage in the proximal direction through the guide-tube 1600.

In some embodiments, the "key" need not be mounted within the "guide tube" 1600 to form an assembly 140a' that is mounted within the lead's deployment lumen 222a. The "key" may be mounted separate from the "guide tube" 1600 either proximal to the guide tube 1600 or distal to the guide tube 1600. Note that if the "key" is mounted distal to the guide tube 1600 the stabilizers 141a, 142a may also be flattened along the loops—such that when the stabilizers 141a, 142a are retracted, their mated cross-sectional shape (a square) can be retracted into the square cross-sectional shape of the guide tube's inner diameter.

In other embodiments, the guide tube 1600 may be designed and extruded from a high durometer polymer, such as Hytrel or nylon, with a square inner lumen. Thus, a separate "key" may not be necessary.

Lead and External Generator Connection

Figure 24A:
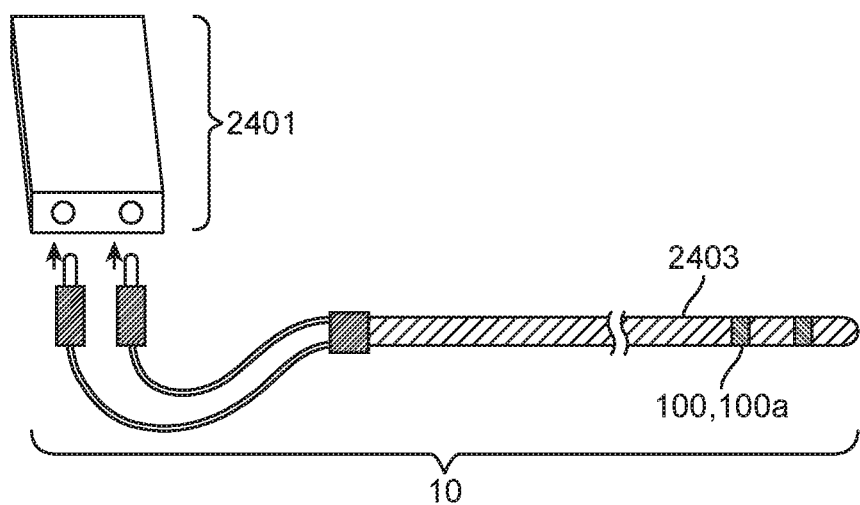
FIG. 24a shows an electrical sensing/stimulation device and an external power generator which may be coupled thereto, according to many embodiments.

Referring now to FIGS. 24a-24c, in some embodiments, the electrical sensing/stimulation device or temporary pacing lead 10 may comprise lead connector plugs 2403 coupled to the proximal portion of the distal lead body 100 or 100a to power the electrodes 131 and 132. The connector plugs 2503 may connect or plug into an external generator 2501. The connector plugs 2503 may fit tightly into the external generator 2401.

In at least some cases, it may be desirable to have the connector plugs 2403 easily disconnect from the external generator 2401, particularly if pulled or tugged relative to the external generator 2401. For example, the connection between the connector plugs 2403 and the external generator 2401 may be at least in part magnetic. The strength of the magnetic connection may be tuned, such as by selecting an appropriately sized magnet, such that the connector plugs 2403 can disconnect from the external generator 2401 under a given force or displacement. To provide the magnetic connection, a magnetic connection hub 2405 may be provided as shown in FIGS. 24b and 24c. FIG. 24b shows the external generator 2401, the connector plugs 2403, and the magnetic connection hub 2405 as disconnected and FIG. 24c shows these elements as connected together. The proximal ends of the connector plugs 2403 may comprise magnets 2407 with a first polarity complementary to magnets 2409 with a second opposite polarity of the magnetic connection hub 2405. The magnetic connection hub 2405 may comprise conductors 2411 which may electrically couple the electrode wires of the connector plugs 2403 with the electrical outlets of the external generator 2401. The magnetic connection hub 2405 may form a tightly fitted connection with the external generator 2401.

In at least some cases, the distal lead segment 100 or 100a may tend to move away from the apex of the heart when the patient moves away from the external generator 2401 while an introducer sheath used to introduce the electrical sensing/stimulation device remains stationary relative to the patient. It may be desired that this movement of the distal lead segment 100 or 100a be reduced or eliminated. In some embodiments, a retractable extension cord may be provided. A retractable extension cord 2501 may be provided between the temporary pacing lead 10 as shown in FIGS. 25a to 25f. Alternatively, a retractable extension cord 2651 may be integrated into the temporary pacing lead 10 itself as shown in FIG. 26g.

Figure 25A:
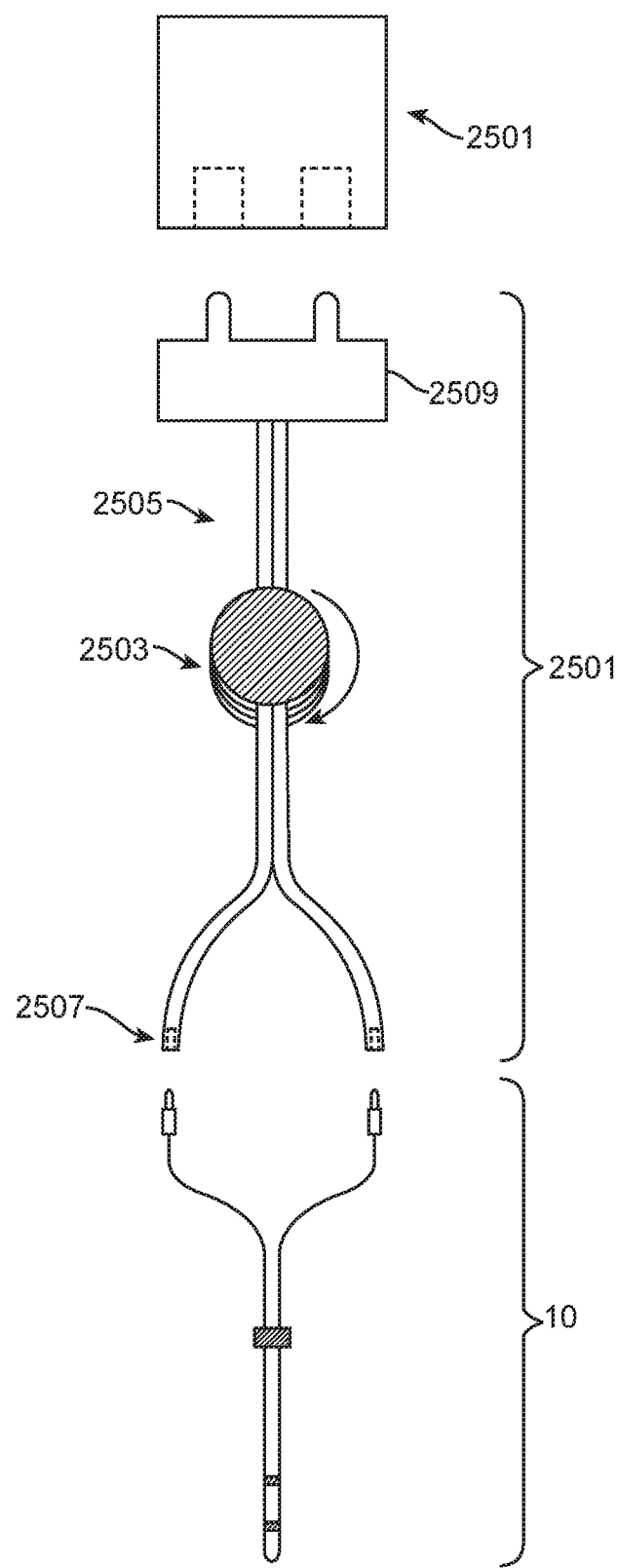
FIG. 25a shows a top view of an electrical sensing/stimulation device, an external power generator, and a retractable extension cord adapter, according to many embodiments.
Figure 25D:
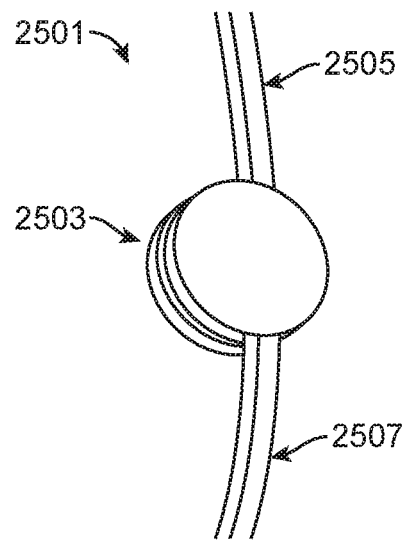
Figure 25E:
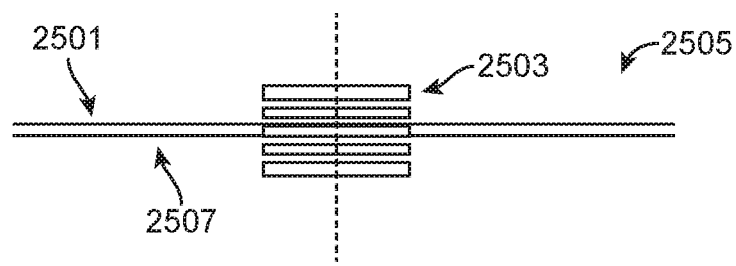
Figure 25F:
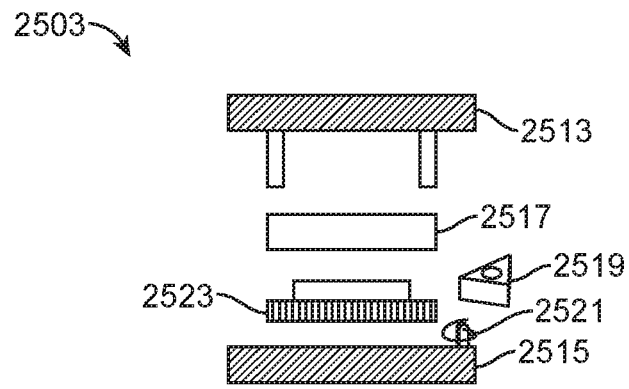
Figure 25G:
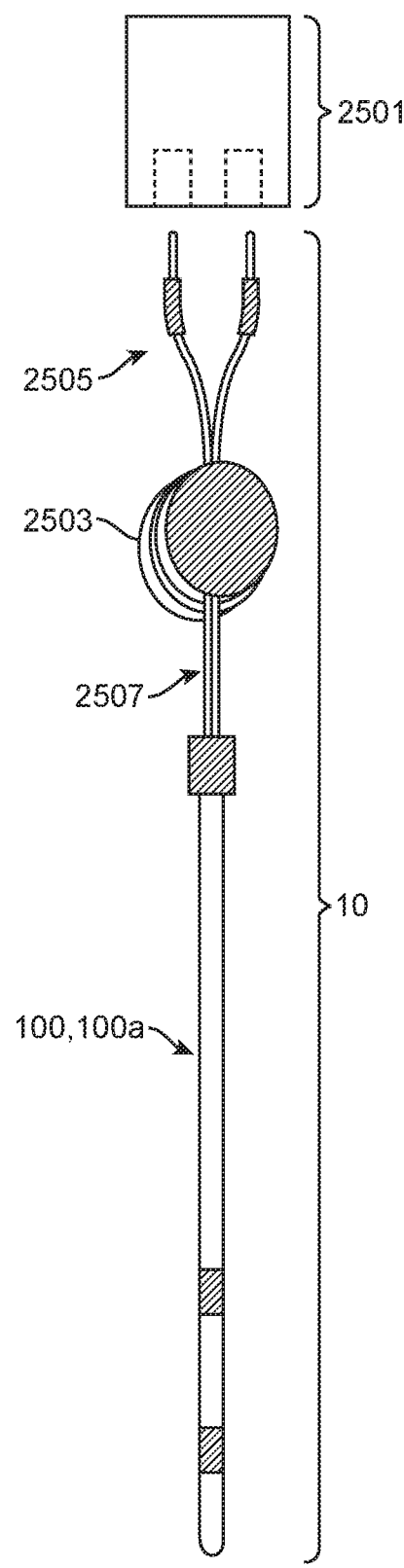
FIG. 25g shows a top view of an electrical sensing/stimulation device with an integrated retractable extension cord and an external power generator, according to many embodiments.

As shown in FIGS. 25a to 25f, the retractable extension cord adaptor 2501 may be an interface between the temporary pacing lead 10 and the external generator 2401. The retractable extension cord adapter 2501 may comprise a torsional device 2503, a proximal cord 2505, distal cords 2507, and a connector 2509 which connects to the external generator 2401. At least a portion of the cords 2505, 2507 may wind about the torsional device 2503 as shown in FIGS. 25d, 25e, and 25f. The torsional device 2503 may provide a bias for the retractable extension cord adapter 2501 to be in an axially retracted configuration as shown in FIGS. 25a and 25b. In the axially retracted configuration shown in FIG. 25b, the distance between the external generator 2401 and the torsional device 2503 may be a first length 2505a spanned by the proximal cord 2505 and the distance between the torsional device 2503 and the ends of the distal cord 2507 may be a second length 2507a spanned by the distal cords 2507. An axial force 2511 may be applied to pull the retractable extension cord adapter 2501 into an axially stretched or extended configuration. The magnitude (or strength) of the axial force 2511 can be tuned, such as by selecting an appropriately size torsional spring with the desired torsional spring constant. In the axially stretched or extended configuration shown in FIG. 25c, the distance between the external generator 2401 and the torsional device 2503 may be a third length 2505b greater than the first length 2505a and spanned by the proximal cord 2505, and the distance between the torsional device 2503 and the ends of the distal cord 2507 may be a fourth length 2507b greater than second length 2507a and spanned by the distal cords 2507. FIG. 25f shows an exploded view of the torsional device 2503, which may comprise a top fixture 2513, a bottom fixture 2515, a torsional spring 2517, geared teeth 2623, a latch 2519, and a torsional spring 2521 between the latch 2519 and the bottom fixture 2515. When the axial force 2511 is applied, the torsional device 2503 may unravel and when the force is removed, the latch 2519 may prevent the cords 2505 and 2507 from retracting. The latch 2519 may be opened so the cords 2505 and 2507 may be wound back into the torsional device 2503. In combination with the torsional device 2503, a magnetic connection or coupling as described above may also be used.

Tissue Stabilizer Movement Detection

In at least some cases, it may be desirable to detect or measure the movement of the tissue attachment members 141 or 142 (or any of the attachment member(s) described above and herein) when engaging tissue.

Figure 26A:
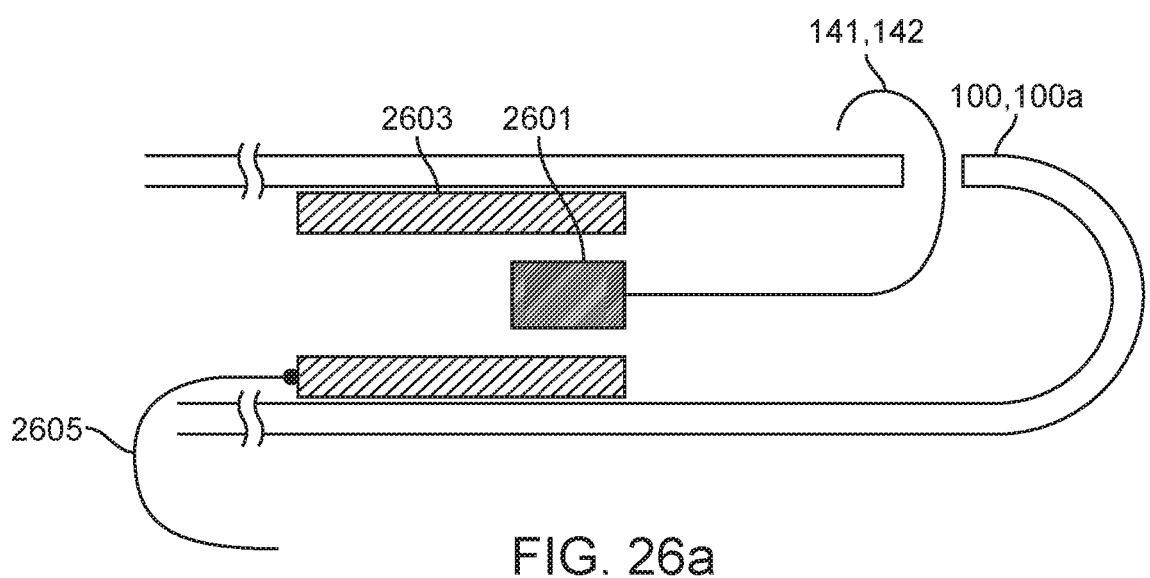
FIG. 26a shows a schematic, based on the detection of electrical current changes, for detecting movement of the Tissue Attachment Members of an electrical sensing/stimulation device, according to many embodiments.

An arrangement to detect or measure the movement of tissue attachment members 141, 142 is shown in FIG. 26a. The attachment members 141, 142 may be coupled to a magnet 2601 within the distal lead segment 100 or 100a. The magnet 2601 may translate within an inner lumen of the distal lead segment 100 or 100a when the attachment members 141, 142 are moved. Such movement may be relative to and within a conductive tube 2603 within the distal lead segment 100 or 100a and may generate a current measurable through wire 2605 which is connected to the conductive tube 2603. The current may pass through a resistor attached to ground so that a voltage measurement may be obtained. The measured voltage can be amplified and variations in voltage readings will therefore correlated to displacement of the attachment members.

Figure 26B:
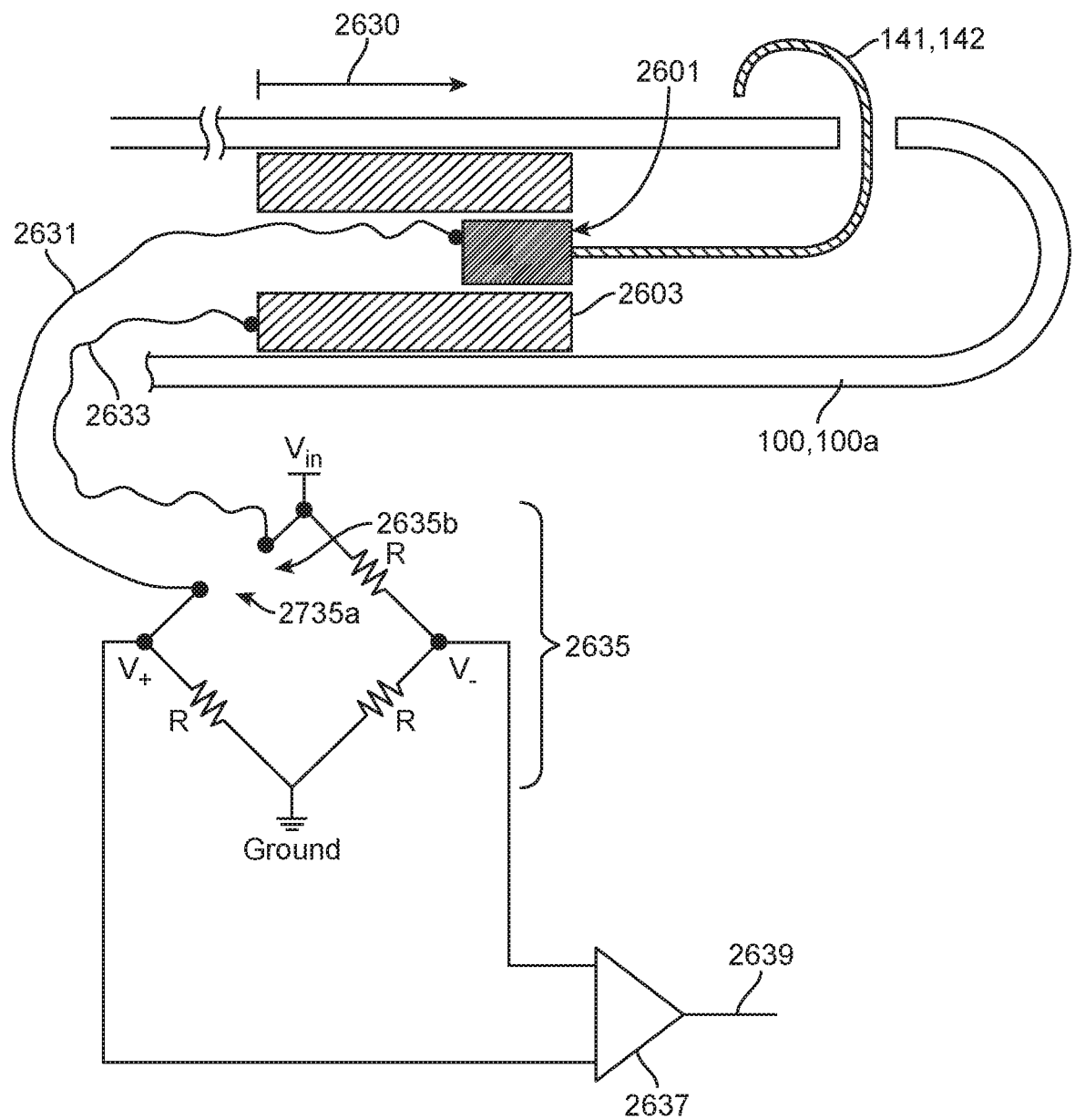
FIG. 26b shows another schematic, based on electrical current changes, for detecting movement of the Tissue Attachment Members of an electrical sensing/stimulation device, according to many embodiments.

Another arrangement to detect or measure the movement of tissue attachment members 141, 142 is shown in FIG. 26b. The attachment members 141, 142 may be coupled to a magnet 2601 within the distal lead segment 100 or 100a. The magnet 2701 may translate within the lumen of the distal lead segment 100 or 100a when the attachment members 141, 142 are moved. Such movement may be relative to and within a conductive tube 2603 within the distal lead segment 100 or 100a. A first wire 2631 may be connected to the magnet 2601, a second wire 2633 may be connected to the conductive tube 2603, and the first and second wires 2631, 2633 may be connected to a Wheatstone-bridge 2635. The movement of the anchor 141, 142 may increase or decrease the distance 2630 and change the resistance from node 2635A to node 2635B in the Wheatstone-bridge 2635. The output of the Wheatstone-bridge 2635 may be input to an amplifier 2637, and changes to the output voltage 2639 may be detected and may be indicative of movement of the anchor 141, 142.

Figure 26C:
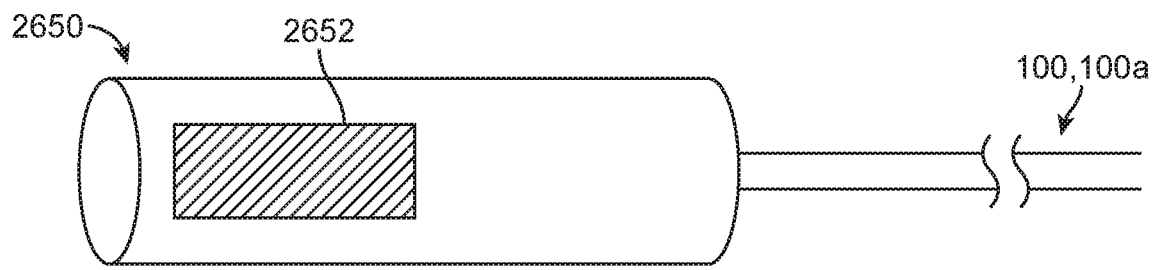
FIG. 26c shows a side view of the LCD display of a Handle of an electrical sensing/stimulation device capable of detecting movement of the Tissue Attachment Members, according to many embodiments.
Figure 26D:
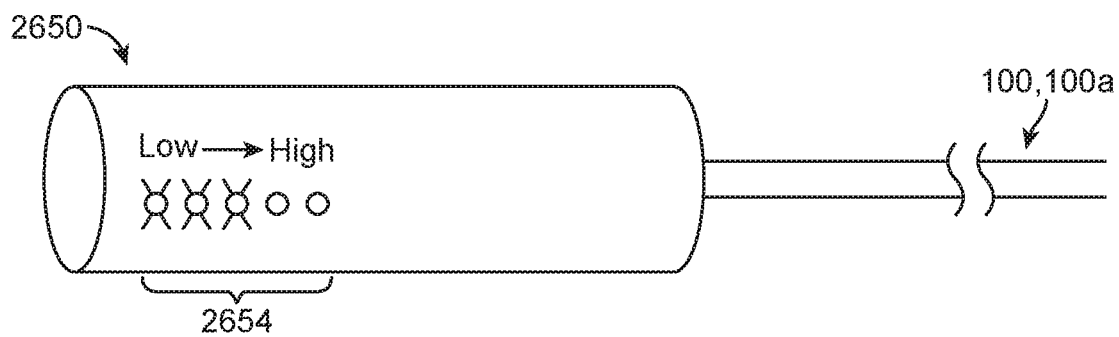
FIG. 26d shows a side view of the LED display of a Handle of an electrical sensing/stimulation device capable of detecting movement of the Tissue Attachment Members, according to many embodiments.
Figure 26E:
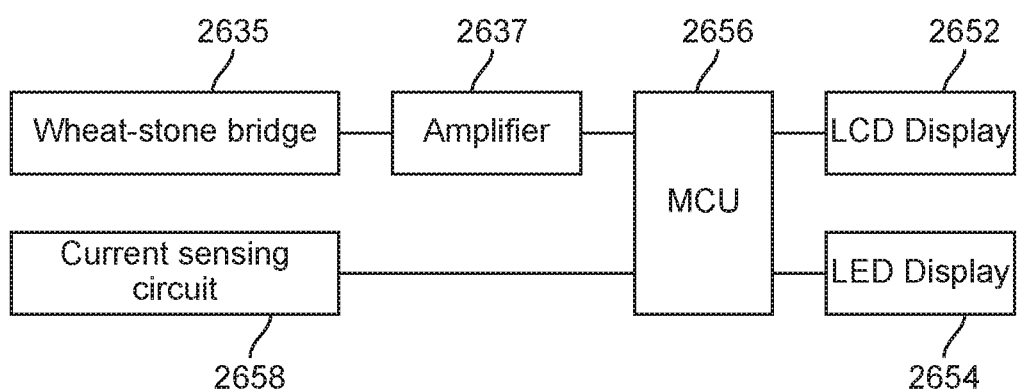
FIG. 26e shows a schematic of the circuitry of the handle of FIG. 26d, and from the electrical current sensing elements of FIGS. 27a and 27b.

Movement of the anchors 141, 142 may be detected and indicated to the user, such as through the LCD (liquid crystal display) display 2652 of a handle 2650 coupled to the distal lead segment 100 or 100a as in FIG. 26c or through LEDs or LED (light emitting diode) display 2654 of the handle 2650 as in FIG. 26d. FIG. 26e shows a schematic of the circuitry of the handle 2650. The handle 2650 may comprise a microcontroller or MCU 2656 which may be coupled to one or more of the Wheatstone-bridge 2635, the amplifier 2637, or a current sensing circuit 2658. The LED display 2652 and/or the LED display 2654 may be coupled to the microcontroller 2656.

The handle 2650 may comprise other control and/or display mechanisms for the distal lead segment 100 or 100a. For example, the handle 2650 may comprise one or more knobs, switches, buttons, sliders, or the like for one or more of deploying the tissue attachment members, activating the electrodes, or expanding the expandable displacement member. The LCD display 2652 or LED display 2654 may additionally indicate capacitive changes, resistance changes, pressure changes, or the like that may occur as the distal lead segment 100, 100a is used in interacting with tissue.

Lead Torque Control and Lead Shaping

Figure 27A:
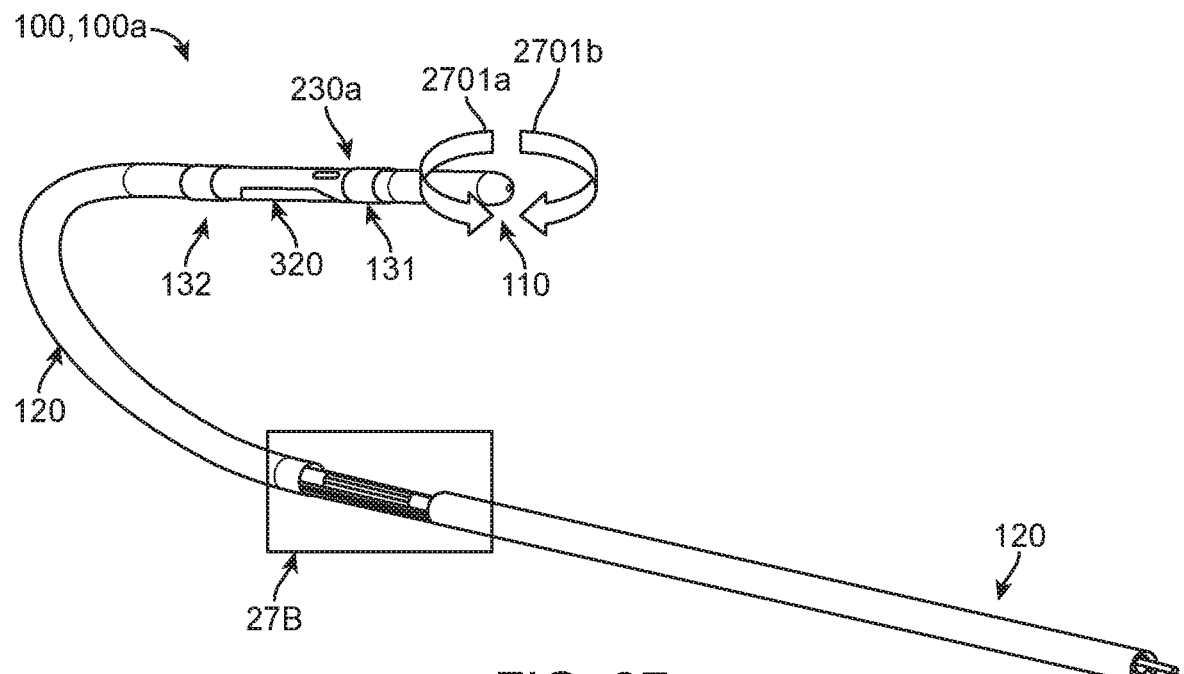
FIG. 27a shows a perspective view of the Distal Lead Segment of an electrical sensing/stimulation device with a Torque Control Member, and decoupled shapeable member, according to many embodiments.
Figure 27B:
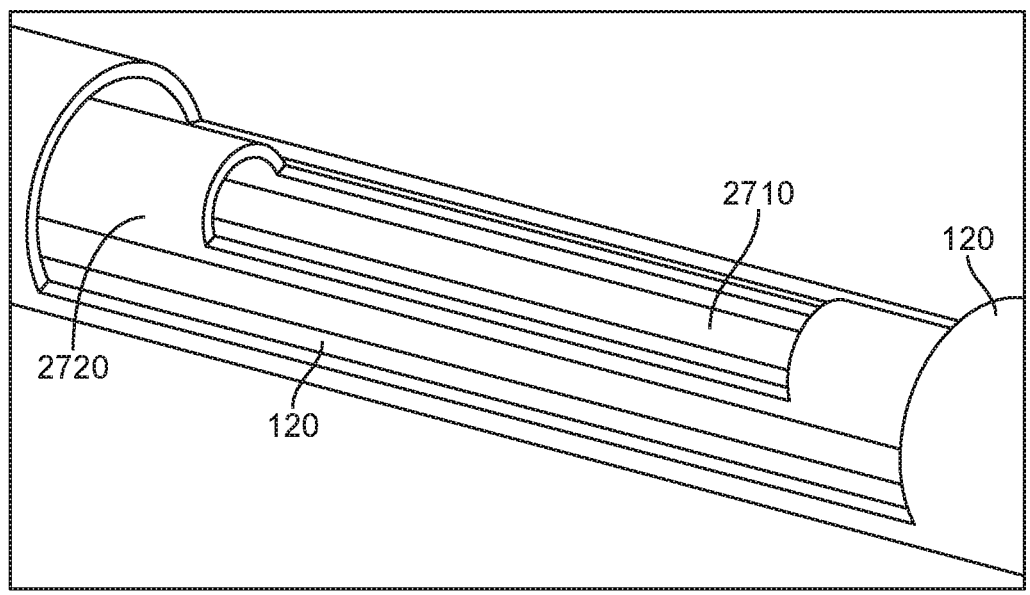

Referring now to FIGS. 27a and 27b, many embodiments may include features for torque control and/or shaping of the distal lead segment 100 or 100a. The lead body 120 may have an inner lumen through which an internal shaping wire 2710 may be translated. The internal shaping wire 2710 may allow a user to bend and shape the distal lead segment 100 or 100a and facilitate its passage through the vasculature. The internal shaping wire 2710 may be biased to have a curved end such that it imparts the same curved shape to the distal lead segment 100 or 100a as shown in FIG. 27a. When the distal lead segment 100 or 100a is advanced through the vasculature, the curve placed on the distal lead segment 100 or 100a can naturally "align" the distal lead segment 100 or 100a to the vascular path. As an example, if the distal lead segment 100 or 100a is navigated to the right ventricle from the femoral vein, the pre-shaped curve (a large U-shape as shown in FIG. 27a) may align itself along the path from the inferior vena cava, into the right atrium, through the tricuspid valve, and into the right ventricle. The pre-shaped curve may straighten as needed to traverse straighter segments of the insertion path but may retain its curvilinear shape to navigate turns in the path toward the target tissue.

In some embodiments, multiple shaping wires may be applied. For example, a first internal shaping wire may be used to help advance the distal lead segment 100 or 100a through a first portion of the vasculature and a second internal shaping wire with a different shape may be used to help advance the distal lead segment 100 or 100a through a second portion of the vasculature.

The internal shaping wire 2710 may be used alone or in conjunction with a torque control member 2720. The torque control member 2720 may comprise a tube or hypotube translatable or bonded within the inner lumen of the lead body 120. The internal shaping wire 2710 may reside in the torque control member 2720 as shown in FIG. 27b. Alternatively, the internal shaping wire 2710 may reside in in the lead body 120 adjacent the torque control member 2720. The torque control member 2720 may reside within the lead body 120 and in some embodiments, may be bonded to the lead body 120 such that the two may act as a single component. Thus, as the proximal portion of the lead body 120 is turned or torqued, the distal lead segment 100 or 100a can follow as shown by the arrows 2701a, 2701b in FIG. 27a.

In some embodiments, the internal shaping wire 2710 is unattached to the lead body 120 and/or torque member 2720 such that the torque member 2720 and the lead body may rotate about the curved axis of the shaping wire as shown by the arrows 2701a, 2701b in FIG. 27a.

While preferred embodiments have been shown and described herein, it will be apparent to those skilled in the art that such embodiments are provided by way of example only. Numerous variations, changes, and substitutions will now occur to those skilled in the art without departing from the scope of the present disclosure. It should be understood that various alternatives to the embodiments described herein may be employed in practicing the inventions of the present disclosure. By way of non-limiting examples, it will be appreciated by those skilled in the art that particular features or characteristics described in reference to one FIG. or embodiment may be combined as suitable with features or characteristics described in another FIG. or embodiment. It is intended that the following claims define the scope of the invention and that methods and structures within the scope of these claims and their equivalents be covered thereby.

What is claimed is:

1. An apparatus for stabilizing or attaching an implantable device to tissue, said apparatus comprising:
   a guide tube having a guide tube lumen with a cross-sectional shape;
   a plurality of elongate members at least partially disposed within the guide tube lumen and translatable relative to the guide tube, each elongate member having a tissue contacting end and an elongate segment, wherein the elongate members have cross-sectional shapes complimentary to one another to form an assembly, the assembly having a perimeter fitting within the guide tube lumen so that the cross-sectional shape of the guide tube maintains rotational alignment of the assembly of the elongate elements as one or more of the elongate elements are translated relative to the guide tube; and an elongate body having a deployment lumen, wherein the guide tube is positioned and secured within the deployment lumen.

2. The apparatus of claim 1, wherein one or more of the elongate members are straight.

3. The apparatus of claim 1, wherein the tissue contacting ends of one or more of the elongate elements comprise a stabilizing element.

4. The apparatus of claim 3, wherein the stabilizing element comprises a tissue contacting distal loop.

5. The apparatus of claim 3, wherein the stabilizing element comprises a tissue penetrating tip.

6. The apparatus of claim 1, wherein the plurality of elongate members comprise a first elongate member having a first elongate segment and a second elongate member having a second elongate segment, and wherein the cross-sectional shapes of the first and second elongate members are complimentary to one another to form the assembly having the perimeter fitting within the guide-tube lumen.

7. The apparatus of claim 6, wherein the cross-sectional shape of one or more of the first or second elongate members is rectangular.

8. The apparatus of claim 7, wherein the cross-sectional shape of the guide tube lumen is square, wherein the cross-sectional shapes of the first and second elongate members are both rectangular, and wherein the rectangular cross-sectional shapes of the first and second elongate members are adapted to mate with each other to form a square sized to fit within the square cross-sectional shape of the guide tube lumen.

9. The apparatus of claim 1, wherein the cross-sectional shape of the guide tube lumen is polygonal.

10. The apparatus of claim 9, wherein the cross-sectional shape of the guide tube lumen is square or rectangular.

11. The apparatus of claim 1, wherein the implantable device comprises one or more deployment ports, and wherein the guide tube is housed within the deployment lumen of the elongate body of the implantable device such that the tissue contacting ends of the elongate members are one or more of advanceable from or retractable through the one or more deployment ports.

12. The apparatus of claim 1, wherein at least a portion of the guide tube has a non-circular outer perimeter.

13. The apparatus of claim 1, further comprising a fluid tight seal between an inner surface of the guide tube and at least a portion of the elongate members.

14. The apparatus of claim 1, wherein at least a portion of the guide tube is made of a high durometer polymer.

15. The apparatus of claim 1, wherein at least a portion of the guide tube is made of one or more of steel, stainless steel, Nitinol, pellathane, Hytrel, Nylon, polyimide, a silicone, or a thermoplastic.

16. The apparatus of claim 1, wherein the guide tube comprises a tubed section and a keyed section mounted at least partially within the tubed section and having the cross-sectional shape of the guide tube to maintain rotational alignment of the assembly of elongate elements.

17. The apparatus of claim 16, wherein the tubed section and the keyed section are made of different materials.

18. The apparatus of claim 17, wherein the keyed section is made of a metal and the tubed section is made of a polymer.

19. The apparatus of claim 1, wherein the guide tube has one or more slits or spiral cuts.

20. The apparatus of claim 1, wherein the guide tube has a predefined curve or radius of curvature.

21. The apparatus of claim 1, wherein the deployment lumen has a cross-sectional shape.

22. The apparatus of claim 21, the guide tube has a perimeter fitting within the deployment lumen so that the cross-sectional shape of the deployment lumen maintains rotational alignment of the guide tube relative to the elongate body.

23. The apparatus of claim 21, wherein the cross-sectional shape of the deployment lumen is polygonal.

24. The apparatus of claim 21, wherein the elongate body comprises one or more deployment ports, and wherein the tissue contacting ends of the elongate members are one or more of advanceable from or retractable through the one or more deployment ports.

25. The apparatus of claim 21, wherein at least a portion of the elongate body is made of a polymer material.

26. An apparatus for stabilizing or attaching an implantable device to tissue, said apparatus comprising:

a guide tube having a guide tube lumen with a cross-sectional shape; and a plurality of elongate members at least partially disposed within the guide tube lumen and translatable relative to the guide tube, each elongate member having a tissue contacting end and an elongate segment, wherein the elongate members have cross-sectional shapes complimentary to one another to form an assembly, the assembly having a perimeter fitting within the guide tube lumen so that the cross-sectional shape of the guide tube maintains rotational alignment of the assembly of the elongate elements as one or more of the elongate elements are translated relative to the guide tube, and wherein the guide tube comprises a tubed section and a keyed section mounted at least partially within the tubed section and having the cross-sectional shape to maintain rotational alignment of the assembly of elongate elements.

27. The apparatus of claim 26, wherein one or more of the elongate members are straight.

28. The apparatus of claim 26, wherein the tissue contacting ends of one or more of the elongate elements comprise a stabilizing element.

29. The apparatus of claim 28, wherein the stabilizing element comprises a tissue contacting distal loop.

30. The apparatus of claim 28, wherein the stabilizing element comprises a tissue penetrating tip.

31. The apparatus of claim 26, wherein the plurality of elongate members comprise a first elongate member having a first elongate segment and a second elongate member having a second elongate segment, and wherein the cross-sectional shapes of the first and second elongate members are complimentary to one another to form the assembly having the perimeter fitting within the guide-tube lumen.

32. The apparatus of claim 31, wherein the cross-sectional shape of one or more of the first or second elongate members is rectangular.

33. The apparatus of claim 32, wherein the cross-sectional shape of the guide tube lumen is square, wherein the cross-sectional shapes of the first and second elongate members are both rectangular, and wherein the rectangular cross-sectional shapes of the first and second elongate members are adapted to mate with each other to form a square sized to fit within the square cross-sectional shape of the guide tube lumen.

34. The apparatus of claim 26, wherein the cross-sectional shape of the guide tube lumen is polygonal.

35. The apparatus of claim 34, wherein the cross-sectional shape of the guide tube lumen is square or rectangular.

36. The apparatus of claim 26, wherein the guide tube is adapted to be housed within a deployment lumen of the implantable device.

37. The apparatus of claim 36, wherein the guide tube is secured within the deployment lumen of the implantable device.

38. The apparatus of claim 36, wherein the implantable device comprises one or more deployment ports, and wherein the guide tube is housed within the deployment lumen of the implantable device such that the tissue contacting ends of the elongate members are one or more of advanceable from or retractable through the one or more deployment ports.

39. The apparatus of claim 26, wherein at least a portion of the guide tube has a non-circular outer perimeter.

40. The apparatus of claim 26, further comprising a fluid tight seal between an inner surface of the guide tube and at least a portion of the elongate members.

41. The apparatus of claim 26, wherein at least a portion of the guide tube is made of a high durometer polymer.

42. The apparatus of claim 26, wherein at least a portion of the guide tube is made of one or more of steel, stainless steel, Nitinol, pellathane, Hytrel, Nylon, polyimide, a silicone, or a thermoplastic.

43. The apparatus of claim 26, wherein the tubed section and the keyed section are made of different materials.

44. The apparatus of claim 26, wherein the keyed section is made of a metal and the tubed section is made of a polymer.

45. The apparatus of claim 26, wherein the guide tube has one or more slits or spiral cuts.

46. The apparatus of claim 26, wherein the guide tube has a predefined curve or radius of curvature.

47. The apparatus of claim 26, further comprising an elongate body having a deployment lumen with a cross-sectional shape, wherein the guide tube is positioned within the deployment lumen.

48. The apparatus of claim 47, the guide tube has a perimeter fitting within the deployment lumen so that the cross-sectional shape of the deployment lumen maintains rotational alignment of the guide tube relative to the elongate body.

49. The apparatus of claim 47, wherein the cross-sectional shape of the deployment lumen is polygonal.

50. The apparatus of claim 47, wherein the guide tube is secured within the deployment lumen of the elongate body.

51. The apparatus of claim 47, wherein the elongate body comprises one or more deployment ports, and wherein the tissue contacting ends of the elongate members are one or more of advanceable from or retractable through the one or more deployment ports.

52. The apparatus of claim 47, wherein at least a portion of the elongate body is made of a polymer material.

* * * * *